(12) United States Patent
Lopez-Mejias et al.

(10) Patent No.: US 10,479,808 B1
(45) Date of Patent: Nov. 19, 2019

(54) BISPHOSPHONATE-BASED COORDINATION COMPLEXES AS ENHANCED PHARMACEUTICAL FORMULATIONS AND METHOD OF PREPARING THE SAME

(71) Applicants: Vilmali Lopez-Mejias, San Juan, PR (US); Gabriel Quinonez-Velez, Carolina, PR (US); Waldemar Amaury Rodriguez-Silva, Carolina, PR (US)

(72) Inventors: Vilmali Lopez-Mejias, San Juan, PR (US); Gabriel Quinonez-Velez, Carolina, PR (US); Waldemar Amaury Rodriguez-Silva, Carolina, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 16/271,754

(22) Filed: Feb. 8, 2019

Related U.S. Application Data

(60) Provisional application No. 62/627,793, filed on Feb. 8, 2018.

(51) Int. Cl.
*C07F 9/38* (2006.01)
*C07F 3/02* (2006.01)

(52) U.S. Cl.
CPC ............. *C07F 9/3847* (2013.01); *C07F 3/02* (2013.01)

(58) Field of Classification Search
None
See application file for complete search history.

(56) References Cited

U.S. PATENT DOCUMENTS

2009/0198038 A1\* 8/2009 Arnold .................. C07F 9/5304
528/283

\* cited by examiner

*Primary Examiner* — Ana Z Muresan
(74) *Attorney, Agent, or Firm* — Hoglund & Pamias, PSC; Roberto J. Rios

(57) ABSTRACT

The hydrothermal reaction between bioactive metals ($Ca^{2+}$, $Zn^{2+}$, and $Mg^{2+}$) salts and clinically utilized bisphosphonate (BP) alendronic acid (ALEN) were performed to prepare several bisphosphonate-based biocompatible coordination complexes (pBioCCs). The invention describes the effect of three variables $M^{2+}$/BP molar ratio, reaction temperature, and pH on the reaction outcomes yields an unprecedented number of crystalline materials of enough crystal quality for structural elucidation. The crystal structure was unveiled by single crystal X-ray diffraction at 100 K and their solid-state properties revealed in tandem with other characterization techniques: thermogravimetry, vibrational spectroscopy, and elemental analysis. The invention provides materials with high structural stability and dissolution properties paving the way for better formulation strategies for alendronic acid (ALEN) through the design of pBioCCs for the treatment of bone-related diseases.

7 Claims, 49 Drawing Sheets

ALEN (Fosamax®)

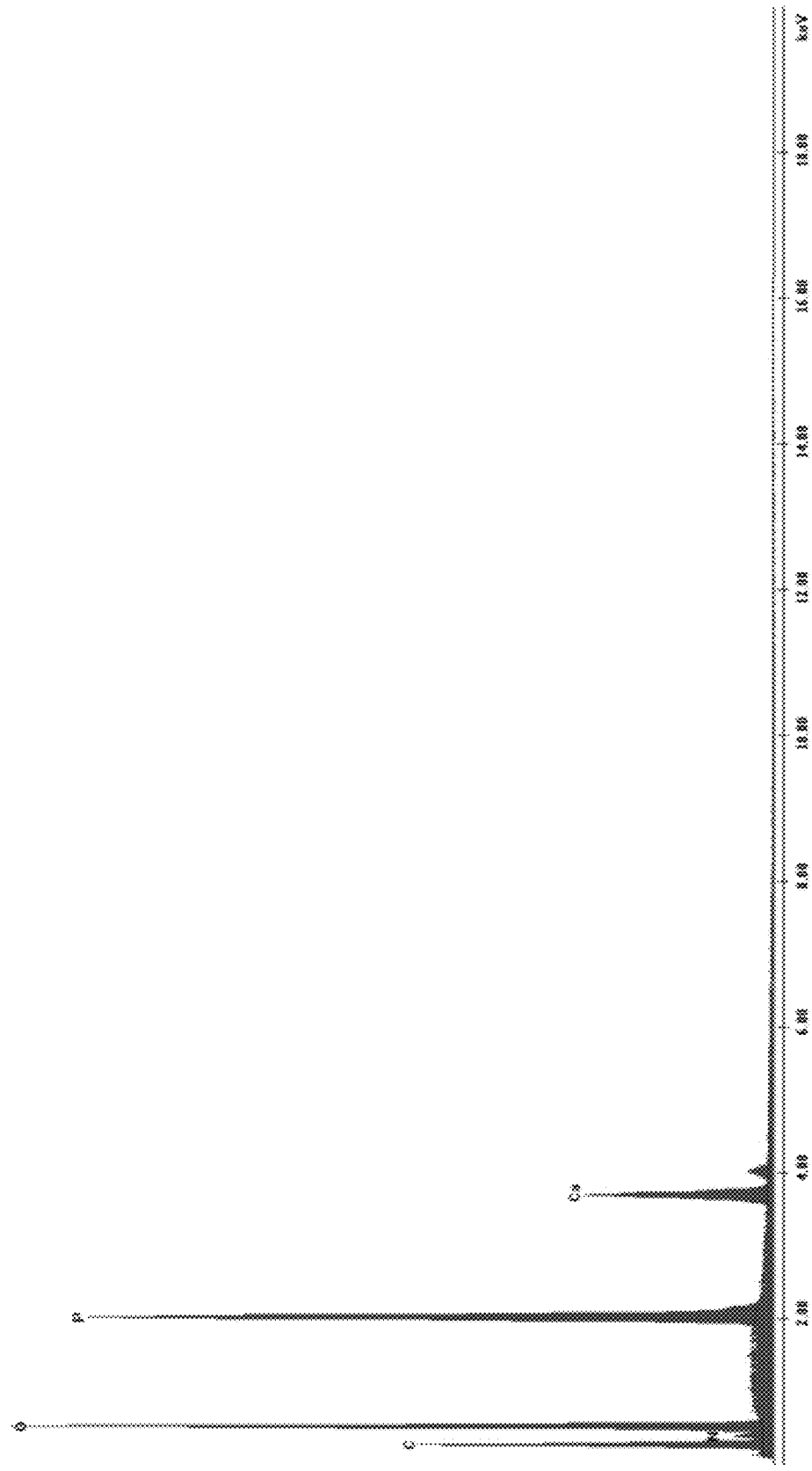

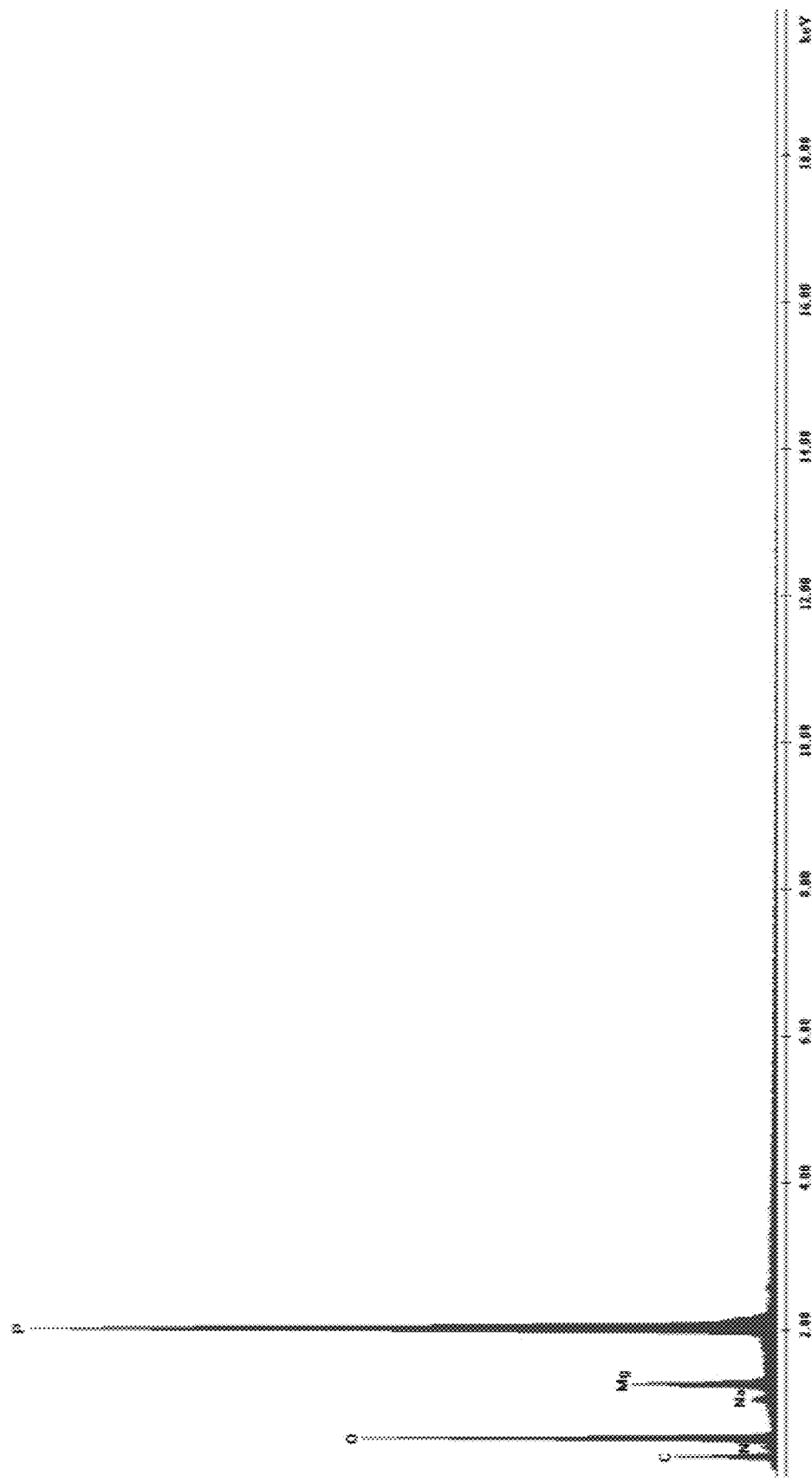

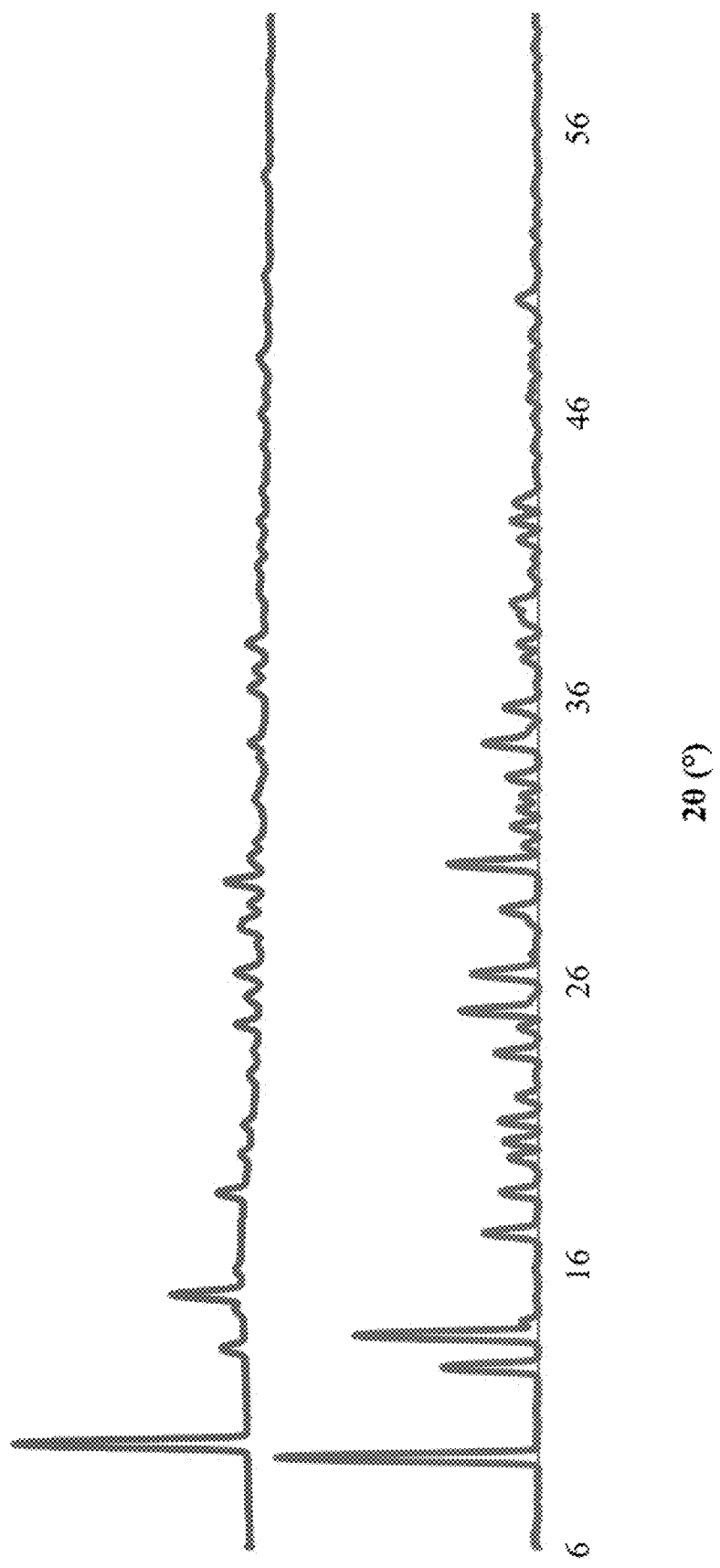

US 10,479,808 B1

BISPHOSPHONATE-BASED COORDINATION COMPLEXES AS ENHANCED PHARMACEUTICAL FORMULATIONS AND METHOD OF PREPARING THE SAME

GOVERNMENT INTEREST

This invention was made with government support under grants DMR1420074 and GM061151 awarded by the National Science Foundation (NSF) and the National Institutes of Health (NIH), respectively. The Government has certain rights in this invention.

BACKGROUND OF THE INVENTION

Coordination polymers (CPs) better known as metal-organic frameworks (MOFs) have attracted considerable attention in the last decade as an important class of organic-inorganic hybrid materials able to absorb and release active pharmaceutical ingredients (APIs). Several MOFs have been demonstrated to absorb therapeutic molecules with unprecedented high loading capacities (i.e. MIL-100 and MIL-101), and their ability for controlled-release has been also explored. Yet, the biocompatibility of the polyfunctional organic molecules and/or metal cations ($Ba^{2+}$, $Sr^{2+}$, $Cr^{2+}$, $Cu^{2+}$, $Cd^{2+}$, and $Co^{2+}$) used to construct the existing extended arrays remains largely a concern, hindering their success in biomedical applications. Recently, the use of biologically relevant or bioactive metal cations has been investigated to introduce additional properties such as imaging and antibacterial activity. The application of MOFs for drug delivery can be accomplished by (1) the entrapment of API within the pores and/or (2) the incorporation of the API as a constituent of the framework. However, the biomedical applications for MOFs, including those in the nanometer size, remain a largely unexplored research arena.

SUMMARY OF THE INVENTION

According to an aspect of the invention, a commercially available BP, which is currently utilized therapeutically to treat osteoporosis and other bone-related diseases was employed as ligand to synthesize bisphosphonate-based biocompatible coordination complexes (pBioCCs) through hydrothermal methods. BPs are ideal ligands for constructing pBioCCs because they (1) present low cytotoxicity, (2) do not significantly metabolize, and (3) possess multiple possible metal binding modes, which paves the way for a variety of open framework structures. In terms of the metal, bioactive metals ($Ca^{2+}$, $Zn^{2+}$, and $Mg^{2+}$) were chosen to minimize cytotoxic effects and, in the case of calcium, promote bone reabsorption. FIG. 1 shows the molecular structure of the selected BP, alendronic acid (ALEN), employed in the treatment of several bone-related diseases and selected for this investigation.

In previous accounts, metal complexes of ALEN with nickel, copper, cobalt, zinc, calcium and manganese have been developed. However, this present invention addresses the shortcomings of currently available ALEN complexes in terms of biocompatibility by employing bioactive metals ($Ca^{2+}$, $Zn^{2+}$, and $Mg^{2+}$) and a clinically utilized BP, such as alendronic acid (ALEN), which in coordination to bioactive metals ($Ca^{2+}$, $Zn^{2+}$, and $Mg^{2+}$) form novel pBioCPs. The systematic exploration of the effect of three variables $M^{2+}$/BP molar ratio, temperature, and pH on the reaction outcomes yielded an unprecedented number of crystalline materials of enough crystal quality for structural elucidation. For five of these materials (ALEN-Ca forms I and II, ALEN-Zn forms I and II, and ALEN-Mg), the crystal structure was unveiled by single crystal X-ray diffraction at 100 K and their solid-state properties revealed in tandem with other characterization techniques, namely, thermogravimetry, vibrational spectroscopy, and elemental analysis.

BRIEF DESCRIPTION OF THE DRAWINGS

Further features and advantages of the invention will become apparent from the following detailed description taken in conjunction with the accompanying figures showing illustrative embodiments of the invention, in which:

FIG. 6A shows energy dispersive spectra of ALEN-Ca form I complex displaying the presence of atoms (carbon, nitrogen, oxygen and phosphorous) present in the ligand and the metal (calcium).

FIG. 6C shows energy dispersive spectra of ALEN-Zn form I complex displaying the presence of atoms (carbon, nitrogen, oxygen and phosphorous) present in the ligand and the metal (zinc).

FIG. 6E shows energy dispersive spectra of ALEN-Mg complex displaying the presence of atoms (carbon, nitrogen, oxygen and phosphorous) present in the ligand and the metal (magnesium).

FIG. 7A shows powder X-ray diffractogram overlay of "as received" ALEN (bottom) and synthetized ALEN-Ca form I complex (top).

DETAILED DESCRIPTION OF THE INVENTION

Experimental

Figure 1:
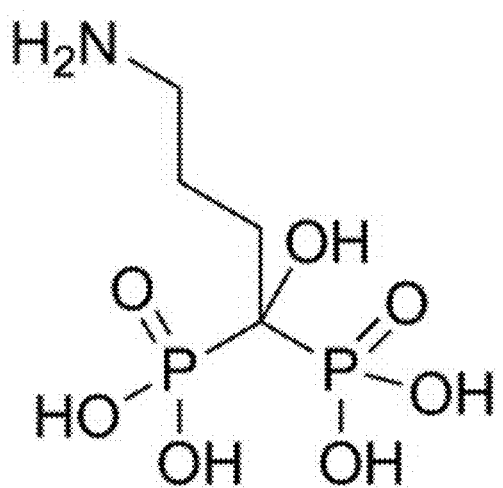
FIG. 1 shows the molecular structure of alendronic acid (ALEN).

Materials
Synthesis of pBioCCs:

Calcium nitrate tetrahydrate [$Ca(NO_3)_2.4H_2O$, 99% pure], calcium chloride hexahydrate [$CaCl_2.6H_2O$, USP grade], zinc nitrate hexahydrate [$Zn(NO_3)_2.6H_2O$, 98% pure], zinc chloride anhydrous [$ZnCl_2$, >98%], magnesium nitrate hexahydrate [$Mg(NO_3)_2.6H_2O$, 99% pure] and etidronic acid 60% aqueous solution (HEDP) were purchased from Sigma-Aldrich (St. Louis, Mo.). Alendronate sodium trihydrate (ALEN), 97% pure was purchased from TCI America (St. Portland, Oreg.). A stock solution of sodium hydroxide (USP grade, 1.5 M) was used for pH adjustments. Distilled water was used as solvent in all syntheses.

Buffers:

Sodium chloride (NaCl, ACS reagent >99.0% pure) and sodium phosphate dibasic ($Na_2HPO_4$, BioXtra, >99.0% pure) from Sigma-Aldrich (St. Louis, Mo.), potassium chloride (KCl, 100.1%) from J.T. Baker (Phillipsburg, N.J.), and potassium phosphate monobasic ($KHPO_4$, HPLC grade, >99.5% pure) from Fluka (Japan), were used as the components to make phosphonate-buffered saline (PBS) solutions (pH=7.40). Hydrochloric acid (HCl, 37%) from Sigma-Aldrich (St. Louis, Mo.) was used to prepare fasted-state simulated gastric fluid (FaSSGF) solution (pH=1.60). Nanopure water from an ARIES Filter Works Gemini High purity water system (18.23 M-Ohm/cm) was used to prepare buffers, calibration curve and phase inversion temperature microemulsion.

Calibration Curves and Dissolution Profiles:

Copper sulfate pentahydrate ($CuSO_4.5H_2O$, ACS reagent >98% pure) were purchased from Sigma-Aldrich (St. Louis, Mo.). PTFE, Non-Sterile, 0.2 μm, 25 mm syringe filters from Fisher brand, Fisher Scientific (Ireland), were used for filtration during dissolution measurements. Alendronate Sodium Tablets-USP (70 mg free equivalent acid) NDC 69097-224-16 and LOT GC70728 supplied from Cipla USA, Inc. (Miami, Fla.).

General Hydrothermal Synthesis for Alendronate-Based Metal Complexes

The hydrothermal synthesis of the pBioCCs was performed by preparing ALEN solutions and the metal salt separately in distilled water at room temperature. The ligand solution was heated until completely dissolved. If required, the pH of the ligand solution was adjusted with 1.5 M NaOH above several of the $pK_a$'s of the ligand (pH=1.61-4.42), where a partially deprotonated phosphonate is the main species present in solution. Using a syringe, the metal solution was added drop wise to the ligand solution and mixed thoroughly. The pH of the resulting solution when both (metal and ligand) solutions are mixed was adjusted below the pH leading to the formation of the metal hydroxide. The resulting mixture was heated until crystals appeared, here, the nucleation induction times varied between minutes to hours. After nucleation was visually detected the vials were removed from heat and left undisturbed to aid the growth of the crystals. The product was collected by vacuum filtration and air-dried.

BPs Complexes Syntheses
ALEN-Ca Form I

A mixture of ALEN and $CaCl_2.6H_2O$ with a molar ratio (1:1) was prepared in distilled water at room temperature as follows. The ligand solution was prepared in a 20 mL vial dissolving 1 mmol (0.2711 g) of solid ALEN in 10 mL of distilled water, heating at 85° C. for 15 min. The metal salt solution was prepared dissolving 1 mmol (0.2191 g) of $CaCl_2.6H_2O$ in 2.5 mL of distilled water. Using a syringe, the metal solution was added to the ligand solution and mixed thoroughly. The resulting mixture was heated at 85° C. until crystals appeared (~30 min.). After the induction time was visually detected, the vials containing the mixture is removed from heating plate and left undisturbed to allow the crystals can grow. The crystals were collected by vacuum filtration and air-dried.

ALEN-Ca Form II

A mixture of ALEN, HEDP and $Ca(NO_3)_2.4H_2O$ with a molar ratio (1:1:1) was prepared in distilled water at room temperature as follows. The ligand solution was prepared in a 20 mL vial dissolving 1 mmol (0.2711 g) of solid ALEN and adding 1 mmol (0.23 mL) of aqueous HEDP in 10 mL of distilled water, heating at 85° C. for 15 min. The metal salt solution was prepared dissolving 1 mmol (0.2362 g) of $Ca(NO_3)_2.4H_2O$ in 2.5 mL of distilled water. Using a syringe, the metal solution was added to the ligand solution and mixed thoroughly. The resulting mixture was heated at 85° C. until crystals appeared (~1 h). After the induction time was visually detected, the vials containing the mixture is removed from heating plate and left undisturbed to allow the crystals can grow. The crystals were collected by vacuum filtration and air-dried.

ALEN-Zn Form I

A mixture of ALEN and $ZnCl_2$ with a molar ratio (1:1) was prepared in distilled water at room temperature as follows. The ligand solution was prepared in a 20 mL vial dissolving 1 mmol (0.2711 g) of solid ALEN in 10 mL of distilled water, heating at 85° C. for 30 min. The metal solution was prepared dissolving 1 mmol (0.1363 g) of $ZnCl_2$ in 2.5 mL of distilled water. Using a syringe, the metal solution was added to the ligand solution and mixed thoroughly. The resulting mixture was heated at 85° C. until crystals appeared (~1 h). After the induction time was visually detected, the vials containing the mixture is removed from heating plate and left undisturbed to allow the crystals can grow. The crystals were collected by vacuum filtration and air-dried.

ALEN-Zn form II

A mixture of ALEN, HEDP and $ZnCl_2$ with a molar ratio (1:1:1) was prepared in distilled water at room temperature as follows. The ligand solution was prepared in a 20 mL vial dissolving 1 mmol (0.2711 g) of solid ALEN and adding 1 mmol (0.23 mL) of aqueous HEDP in 10 mL of distilled water, heating at 85° C. for 15 min. The metal salt solution was prepared dissolving 1 mmol (0.1363 g) of $ZnCl_2$ in 2.5 mL of distilled water. Using a syringe, the metal solution was added to the ligand solution and mixed thoroughly. The resulting mixture was heated at 85° C. until crystals appeared (20 min.). After the induction time was visually detected, the vials containing the mixture is removed from heating plate and left undisturbed to allow the crystals can grow. The crystals were collected by vacuum filtration and air-dried.

ALEN-Mg

A mixture of ALEN, HEDP and $Mg(NO_3)_2 \cdot 6H_2O$ with a molar ratio (1:1:1) was prepared in distilled water at room temperature as follows. The ligand solution was prepared in a 20 mL vial dissolving 1 mmol (0.2711 g) of solid ALEN and adding 1 mmol (0.23 mL) of aqueous HEDP in 10 mL of distilled water, heating at 85° C. for 15 min. The metal solution was prepared dissolving 1 mmol (0.2564 g) of $Mg(NO_3)_2 \cdot 6H_2O$ in 2.5 mL of distilled water. Using a syringe, the metal solution was added to the ligand solution and mixed thoroughly. The resulting mixture was heated at 85° C. until crystals appeared (~1 h). After the induction time was visually detected, the vial was removed from heating plate and left undisturbed to allow the crystals can grow. The crystals were collected by vacuum filtration and air-dried.

Polarized Optical Microscopy

Optical micrographs were recorded with a Nikon Eclipse Microscope LV100NPOL, equipped with a Nikon DS-Fi2 camera and NIS Elements BR software version 4.30.01.

Raman Microscopy

Raman spectra were recorded at room temperature in a Thermo Scientific DXR Raman microscope, equipped with a 532 nm laser, 400 lines/nm grating, and 50 µm slit. The spectra were collected over the range of 3,600 and 100 $cm^{-1}$ by averaging 32 scans with 5 sec exposures in the OMNIC for Dispersive Raman software version 9.2.0.

Morphological Characterization

Micrographs and X-ray microanalysis (SEM-EDS) were recorded with a JEOL JSM-6480LV scanning electron microscope with an Evenhart Thomley secondary electron imagining (SEI) detector. Images were taken with an acceleration voltage of 20 kV, an electron beam of 11 mm width, with a spot size value of 36, SEI signal and HV vacuum mode.

Micro-Powder X-Ray Diffraction (PXRD)

Powder diffractograms were collected for all polycrystalline samples using a Rigaku XtaLAB SuperNova single micro-focus Cu—Kα radiation (λ=1.5417 Å) source equipped with a HyPix3000 X-ray detector in transmission mode operating at 50 kV and 1 mA. Powder samples were mounted in MiTeGen micro loops. Powder diffractograms were collected at 100 K over an angular 2θ range between 6-60° with a step of 0.01° using the Gandalfi move experiment for powders. Data was analyzed within the CrystAllis$^{PRO}$ software v. 1.171.3920a.

Single Crystal X-Ray Diffraction

The crystalline products of the hydrothermal reactions were observed under the microscope using polarized light to assess their crystal quality. Suitable single crystals were mounted in MiTeGen micro loops for structure elucidation. Structural elucidation was performed in either of two instruments; crystal structure for ALEN-Zn form I was collected in a Bruker AXS SMART APEX-II single crystal diffractometer equipped with a Monocap collimator and APEX-II CCD detector with a Mo—Kα (λ=0.71073 Å) radiation source operating at 50 kV and 40 mA. The data collection was carried out at 100 K using an Oxford Cryosystems Cryostream 700 cooler. Alternatively, other crystal structures (ALEN-Ca forms I and II, ALEN-Zn form II and ALEN-Mg) were collected with a Rigaku XtaLAB SuperNova single micro-focus Cu—Kα radiation (λ=1.5417 Å) source equipped with a HyPix3000 X-ray detector in transmission mode operating at 50 kV and 1 mA within the CrystAllis$^{PRO}$ software v. 1.171.3920a. The data collection was carried out at 100 K using an Oxford Cryosystems Cryostream 800 cooler. All crystal structures were solved by direct methods. The refinement was performed using full-matrix least squares on $F^2$ within the Olex2 software v1.2. All non-hydrogen atoms were anisotropically refined.

Thermal Characterization

Thermographs were recorded in a TGA Q500 (TA Instruments Inc.). Thermograph of the BP and pBioCCs were collected using a temperature range of 30-700° C. at 5° C./min under a $N_2$ gas purge. In all cases, ~10 mg of powder sample was thermally treated. Data was analyzed with TA Universal Analysis software version 4.3A.

Dissolution Rate Measurements

Dissolution profiles were performed via Copper (II) complexation with ALEN and quantified by measuring absorbance through UV-Vis spectroscopy. Dissolution profiles were recorded for ALEN sodium reagent, ALEN Sodium Tablets-USP (generic form of Fosamax®), ALEN-Ca forms I and II, and ALEN-Zn forms I and II, and ALEN-Mg. Dissolution tests were performed in 100 mL of PBS buffer (pH=7.40) and FaSSGF (pH=1.60), at 37° C. under constant stirring at 150 rpm. The absorbance of the soluble ALEN-Cu complex was measured at 231 nm in PBS and 225 nm in FaSSGF, against a reagent blank. Absorbance measurements were performed on an Agilent Technologies Cary Series UV-Vis Spectrophotometer, Cary 100 UV-Vis model; using the UV Cary Scan software version v.20.0.470. All measurements were performed with a 400-200 nm scan.

Dissolution in PBS

Stock Solution:

Standard stock solution of ALEN was prepared by dissolving 100 mg of the drug in a 100-mL volumetric flask with PBS. More dilute solutions were obtained by appropriate dilution from this stock solution, as explained in the Calibration Curve section below.

Calibration Curve:

Accurately measured aliquots of the ALEN stock solution were transferred into a series of 25-mL volumetric flasks to achieve a concentration range of 0.05-0.7 mg/mL. Each solution was completed to the 25-mL mark with PBS.

To generate the ALEN-Cu complex, 4 mL of the diluted ALEN solutions were transferred into a series of 25-mL volumetric flasks to achieve an ALEN-Cu concentration range of 0.008-0.11 mg/mL. To each flask, 20 mL of 2.5 mM $CuSO_4$ solution was added, homogenized and completed to volume with nanopure water. The absorbance of the formed ALEN-Cu complex was measured at 231 nm against a reagent blank prepared by the addition of 4 mL PBS buffer and 20 mL of the $CuSO_4$ solution in a 25-mL volumetric flask and completed to volume with nanopore water.

Dissolution Profile:

Dissolution profiles were recorded for alendronate sodium reagent (ALEN), Alendronate Sodium Tablets-USP (generic form of Fosamax®), ALEN-Ca form I, ALEN-Ca form II, ALEN-Zn form I, ALEN-Zn form II and ALEN-Mg. Dissolution tests were performed in 100 mL of PBS buffer (pH=7.40), controlling temperature at 37° C. and stirring at 150 rpm. For the alendronate-based coordination complexes, reagent and tablets, 70 mg of the solid were grinded using a mortar and pestle. The powder was added to the PBS solution at the beginning of the dissolution under stirring. Samples of 1.6 mL were collected after 0, 5, 10, 15, 20 and 25 s to record the dissolution for the deglutition profile. For the complete dissolution profile, samples of the exact volume amount were collected from 1-6 min, in one-minute intervals. After the six-minute period, samples for 10, 15 and 20 min were collected. After collection, the samples were filtrated using a PTFE filter. The filtered solutions were placed in 10 mL volumetric flasks. To produce the ALEN-Cu complex, 7.4 mL of the 2.5 mM $CuSO_4$ solution was added and completed to volume with nanopure water. The absorbance of the formed ALEN-Cu complex was measured at 231 nm against a reagent blank prepared by the addition of filtered 1.6 mL PBS buffer in a 10-mL volumetric flask, with 7.4 mL of the 2.5 mM copper (II) sulfate solution and completed to volume with nanopure water. Absorbance measurements were performed on an Agilent Technologies Cary Series UV-Vis Spectrophotometer, Cary 100 UV-Vis model; using the UV Cary Scan software version v.20.0.470. All measurements were performed with a 400-200 nm scan.

Dissolution in FaSSGF

Stock Solution:

Standard stock solution of ALEN was prepared by dissolving 100 mg of the drug in a 100-mL volumetric flask with FaSSGF. More dilute solutions were obtained by appropriate dilution from this stock solution, as explained in the Calibration Curve section below.

Calibration Curve:

Accurately measured aliquots of the ALEN stock solution were transferred into a series of 25-mL volumetric flasks to achieve a concentration range of 0.05-0.7 mg/mL. Each solution was completed to the 25-mL mark with FaSSGF.

To generate the ALEN-Cu complex, 3 mL of the diluted ALEN solutions were transferred into a series of 25-mL volumetric flasks to achieve an ALEN-Cu concentration range of 0.006-0.084 mg/mL. To each flask, 15 mL of 2.5 mM $CuSO_4$ solution and 5 mL of PBS was added, homogenized and completed to volume with nanopure water. The absorbance of the formed ALEN-Cu complex was measured at 225 nm against a reagent blank prepared by the addition of 3 mL FaSSGF, 5 mL of PBS buffer and 15 mL of the $CuSO_4$ solution in a 25-mL volumetric flask and completed to volume with nanopore water.

Dissolution Profile:

Dissolution profiles were recorded for alendronate sodium reagent (ALEN), Alendronate Sodium Tablets-USP (generic form of Fosamax®), ALEN-Ca form I, ALEN-Ca form II, ALEN-Zn form I, ALEN-Zn form II and ALEN-Mg. Dissolution tests were performed in 100 mL of FaSSGF (pH=1.60), controlling temperature at 37° C. and stirring at 150 rpm. For the alendronate-based coordination complexes, reagent and tablets, 70 mg of the solid were grinded using a mortar and pestle. The powder was added to the FaSSGF solution at the beginning of the dissolution under stirring. Samples of 1.2 mL were collected after 0, 5, 10, 15, 20 and 25 s to record the early-state dissolution profile. For the complete dissolution profile, samples of the exact volume amount were collected from 1-6 min, in one-minute intervals. After the six-minute period, samples for 10, 15 and 20 min were collected. After collection, the samples were filtrated using a PTFE filter. The filtered solutions were placed in 10 mL volumetric flasks. To produce the ALEN-Cu complex, 2 mL of PBS and 6 mL of the 2.5 mM $CuSO_4$ solution was added and completed to volume with nanopure water. The absorbance of the formed ALEN-Cu complex was measured at 225 nm against a reagent blank prepared by the addition of filtered 1.2 mL FaSSGF solution in a 10-mL volumetric flask, with 2 mL PBS buffer and 6 mL of the 2.5 mM copper (II) sulfate solution and completed to volume with nanopure water. Absorbance measurements were performed on an Agilent Technologies Cary Series UV-Vis Spectrophotometer, Cary 100 UV-Vis model; using the UV Cary Scan software version v.20.0.470. All measurements were performed with a 400-200 nm scan.

Results and Discussion.

Figure 2:
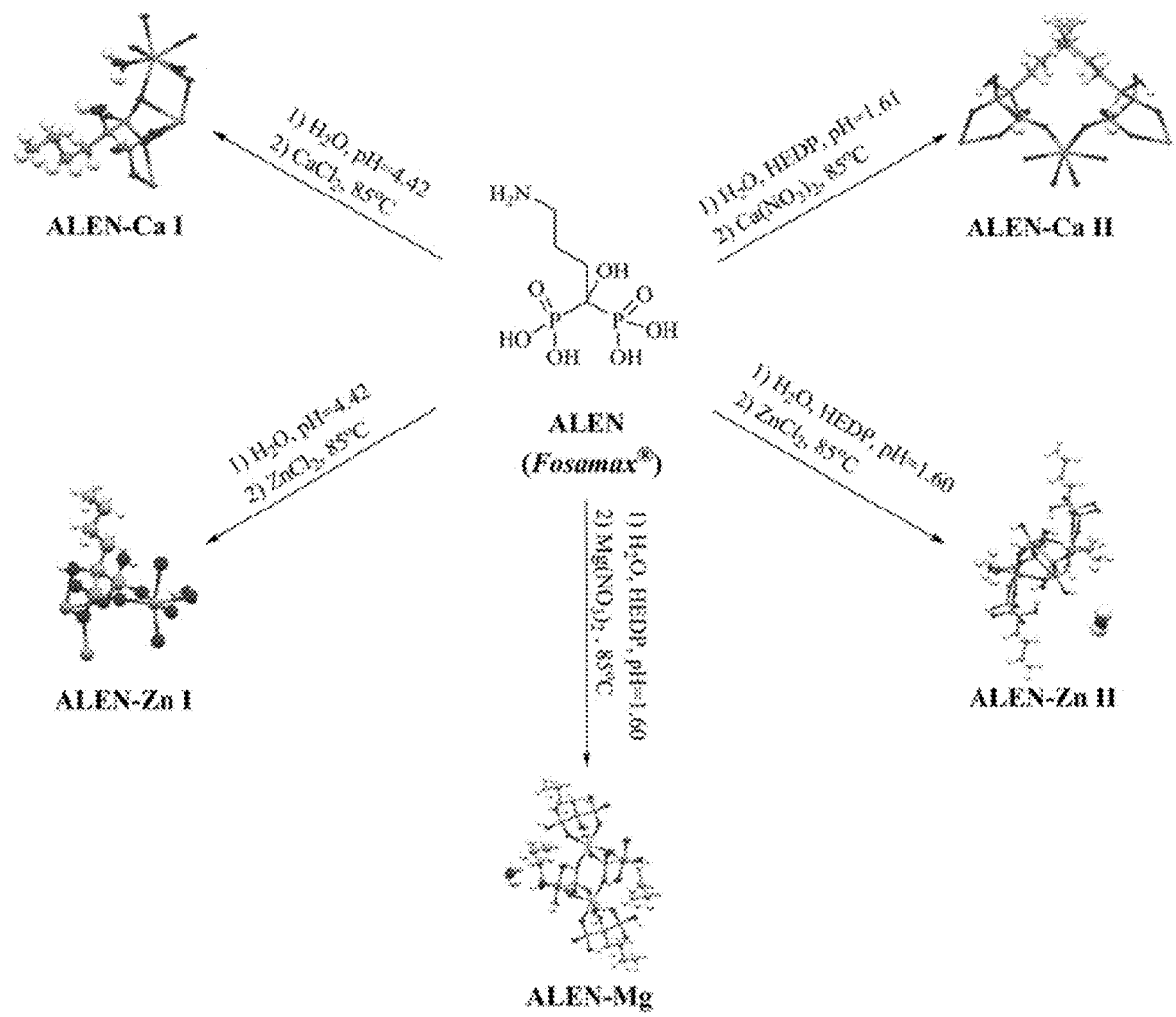
FIG. 2 shows a schematic diagram of the design space explored leading to crystalline phases when ALEN was reacted with the three bioactive metals ($Ca^{2+}$, $Zn^{2+}$, and $Mg^{2+}$), according to the present invention.
Figure 3:
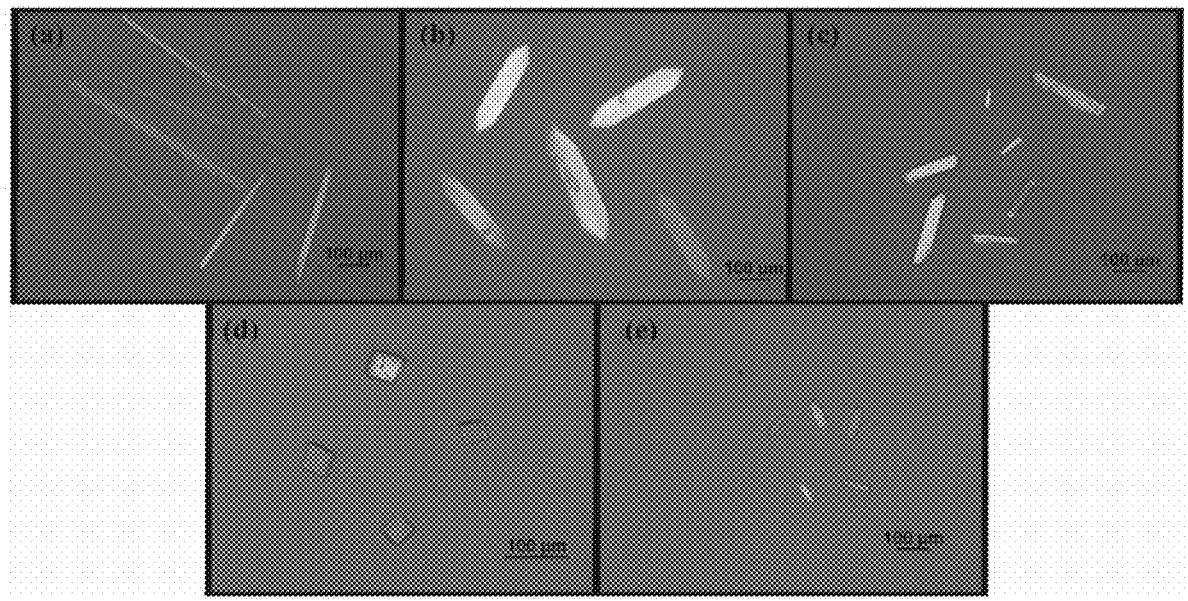
FIG. 3 shows polarized optical micrographs of isolated crystalline materials from the hydrothermal syntheses between alendronate (ALEN) and bioactive metals ($Ca^{2+}$, $Zn^{2+}$ and $Mg^{2+}$) presenting the highest quality single crystals as observed under polarized light.

In the present invention, the reaction between the selected BP (ALEN) and different bioactive metal salts formed several crystalline phases with rich variety of structural motifs, depending on the synthesis conditions. Three variables were analyzed according to the invention: $M^{2+}$/BP molar ratios (1:1, 1:2, 2:1, 2:3, 3:2), reaction temperatures (65° C., 85° C., and 100° C.), and pH, while the reaction pressure, oxidation state, coordination number, and radius of the metal were kept almost constant. With regards to pH, various factors were considered: (1) that the pH of the ligand solution was above several of the $pK_a$'s of the BP ligand, where a partially deprotonated phosphonate is the main species present in solution, and (2) that the pH of the resulting solution (when the metal and the ligand solutions are mixed) lies below the pH leading to the formation of the metal hydroxide. FIG. 2 highlights the design space explored according to the invention. The majority of the successful bisphosphonate-metal complexes formed while employing a 1:1 $M^{2+}$/BP molar ratio at 85° C., and in acidic media (pH<7.0). Many of the hydrothermal synthesis spontaneously formed microcrystalline powders, interestingly; in most of these cases $Mg^{2+}$ was employed as the bioactive metal. Five pBioCCs were produced as single crystals with enough quality for structural elucidation by single X-ray diffraction, as shown in FIG. 3. Here, the synthesis, solid-state characterization and structural elucidation of the phases presenting the highest quality single crystals are discussed. Additional experimental details for the conditions that yielded microcrystalline powders are explained throughout the specification.

Raman Spectroscopy Analysis of the ALEN-Based Metal Complexes.

Figure 4:
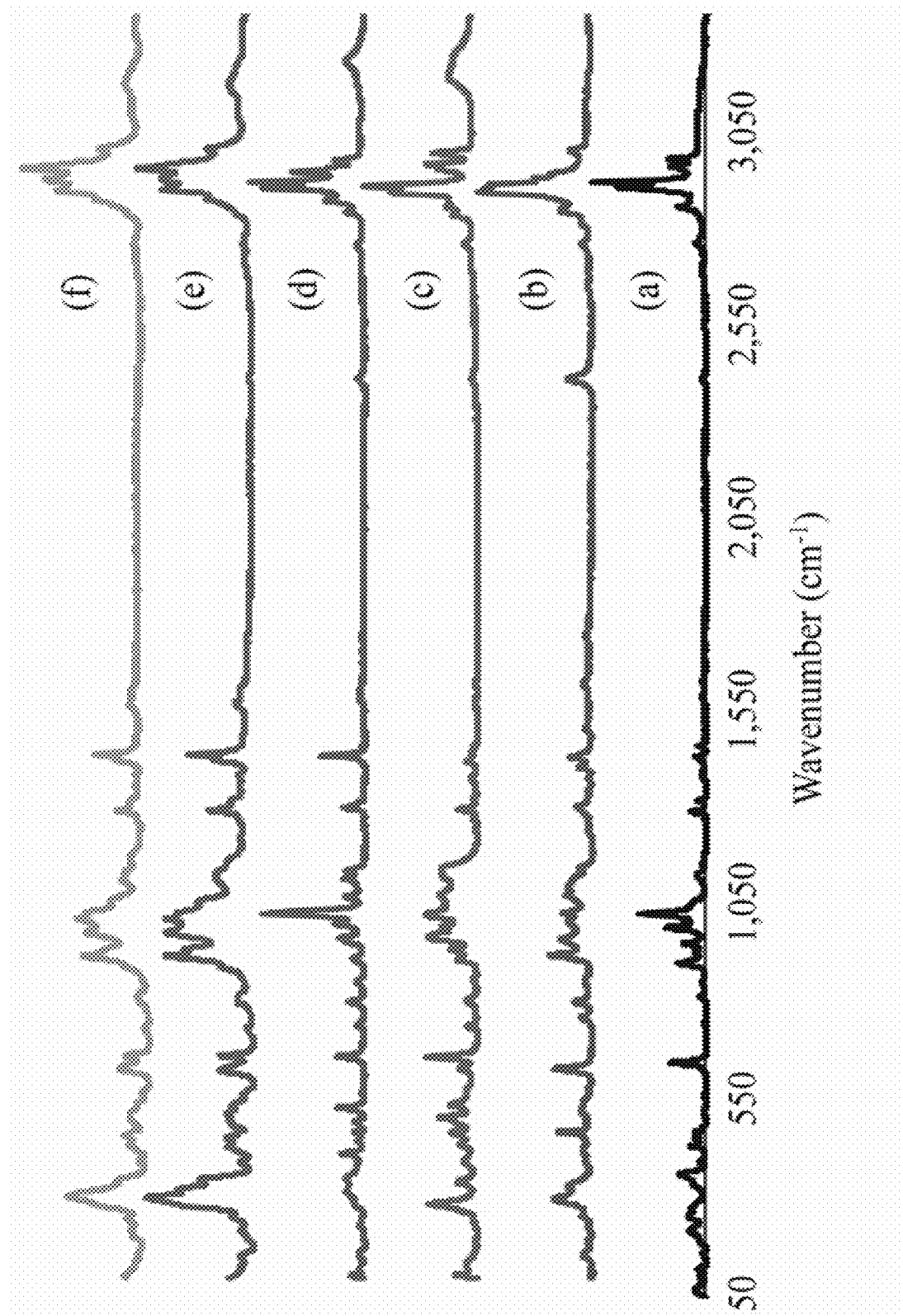
FIG. 4 shows Raman spectra overlay of the isolated products of the hydrothermal syntheses between (a) alendronate (ALEN) and bioactive metals ($Ca^{2+}$, $Zn^{2+}$ and $Mg^{2+}$); (b) ALEN-Ca form I, (c) ALEN-Ca form II, (d) ALEN-Zn form I, (e) ALEN-Zn form II, and (f) ALEN-Mg.
Figure 5A:
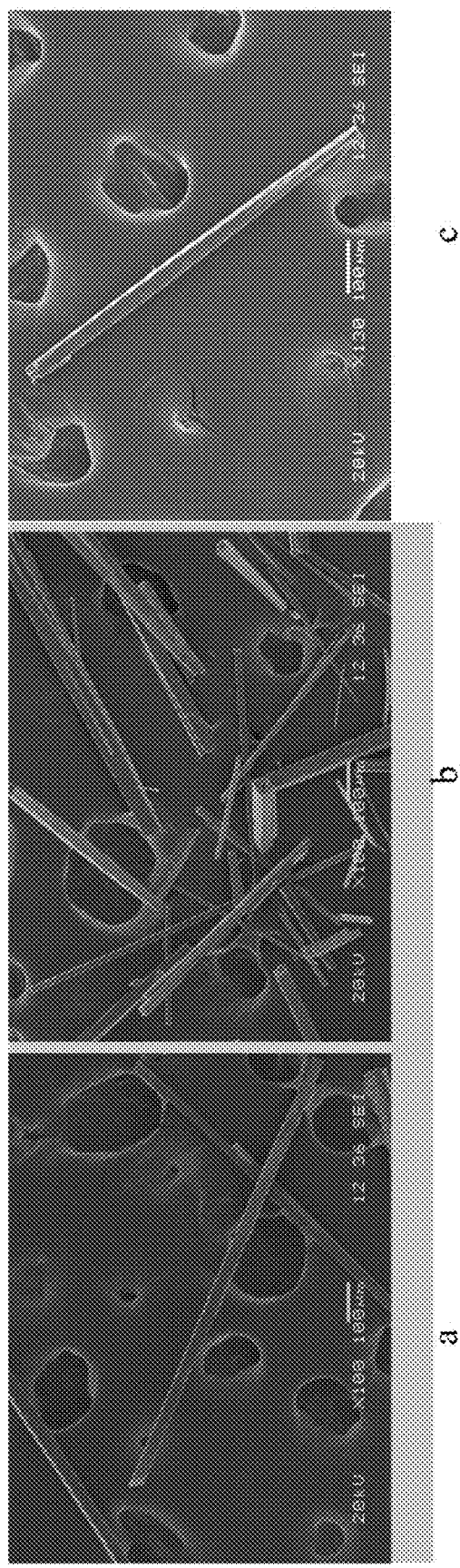
FIG. 5A shows scanning electron micrographs of (a) ALEN-Ca form I pBioCC single crystal at a ×100 magnification, (b) crystals of ALEN-Ca form I pBioCC at a ×100 magnification, and (c) a single crystal of ALEN-Ca form I pBioCC at a ×130 magnification.
Figure 5B:
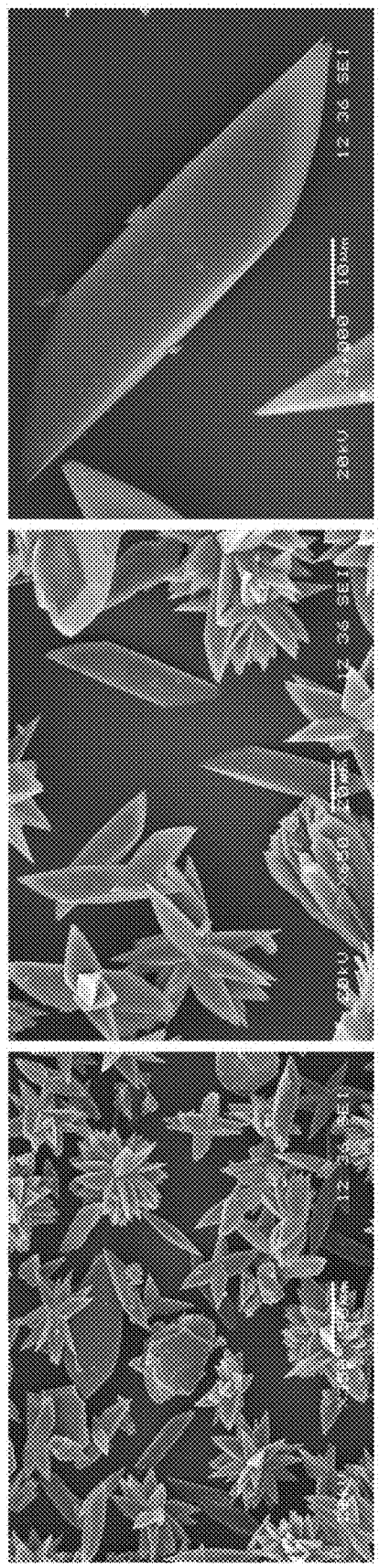
FIG. 5B shows scanning electron micrographs of (a), ALEN-Ca form II crystal clusters at a ×350 magnification, (b) ALEN-Ca form II pBioCC single crystals and clusters at a ×650 and (c) a single crystal of ALEN-Ca form II pBioCC at a ×2,000 magnification.
Figure 5C:
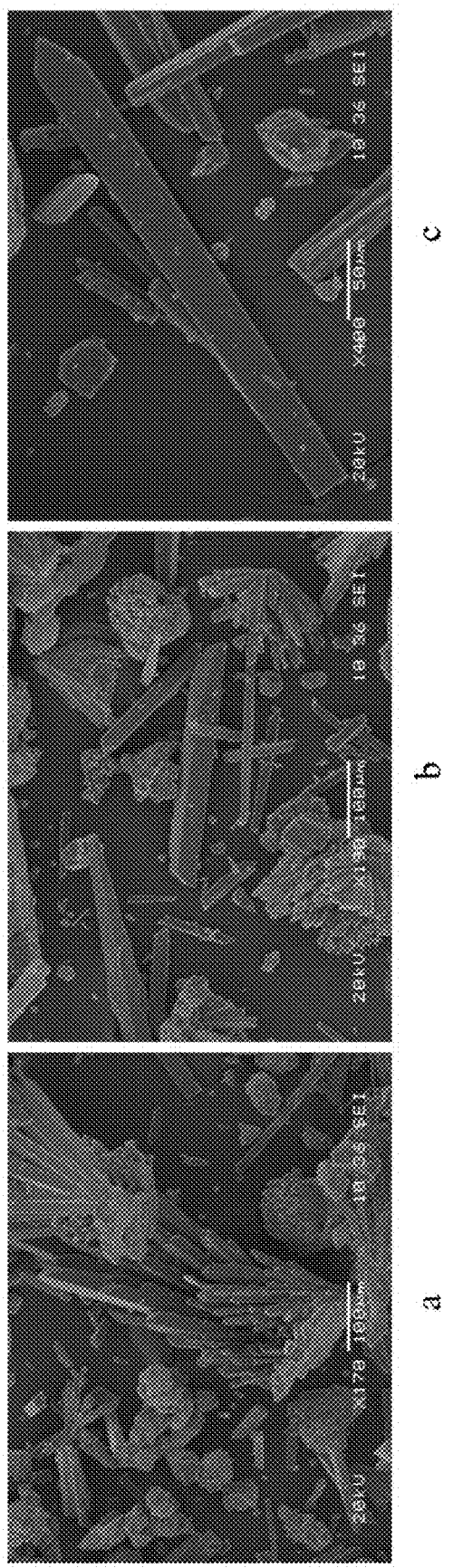
FIG. 5C shows scanning electron micrographs of (a) ALEN-Zn form I pBioCC clusters at a ×170 magnification, (b) crystals and clusters of ALEN-Zn form I pBioCC at a ×190 magnification, and (c) a single crystal of ALEN-Zn form I pBioCC at a ×400 magnification.
Figure 5D:
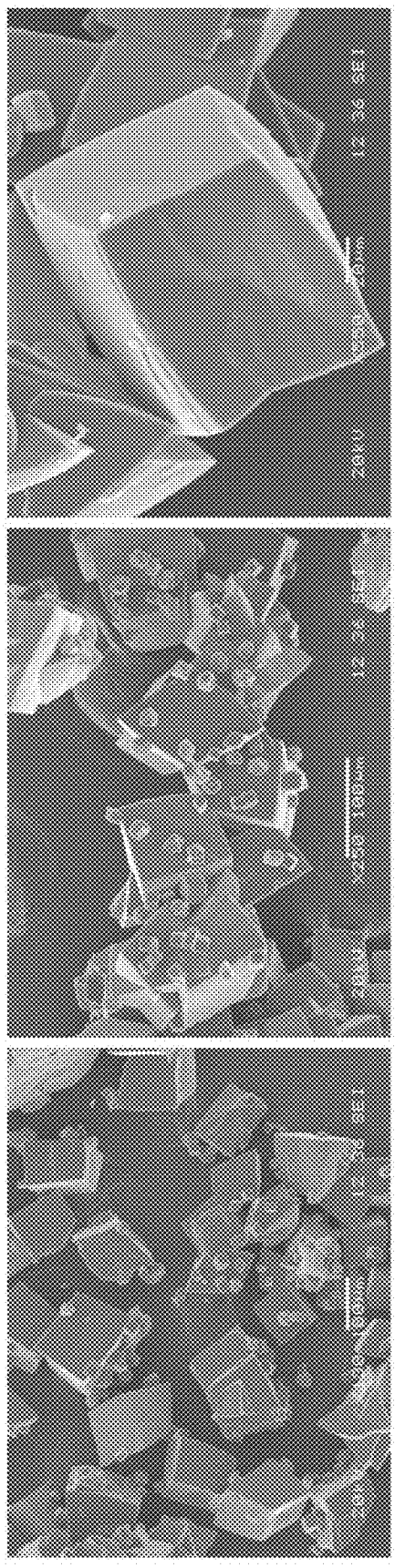
FIG. 5D shows scanning electron micrographs of (a) ALEN-Zn form II pBioCC clusters and single crystals at a ×130 magnification, (b) single crystals of ALEN-Zn form II pBioCC at a ×250 magnification, and (c) an isolated single crystal of ALEN-Zn form II pBioCC at a ×550 magnification.
Figure 5E:
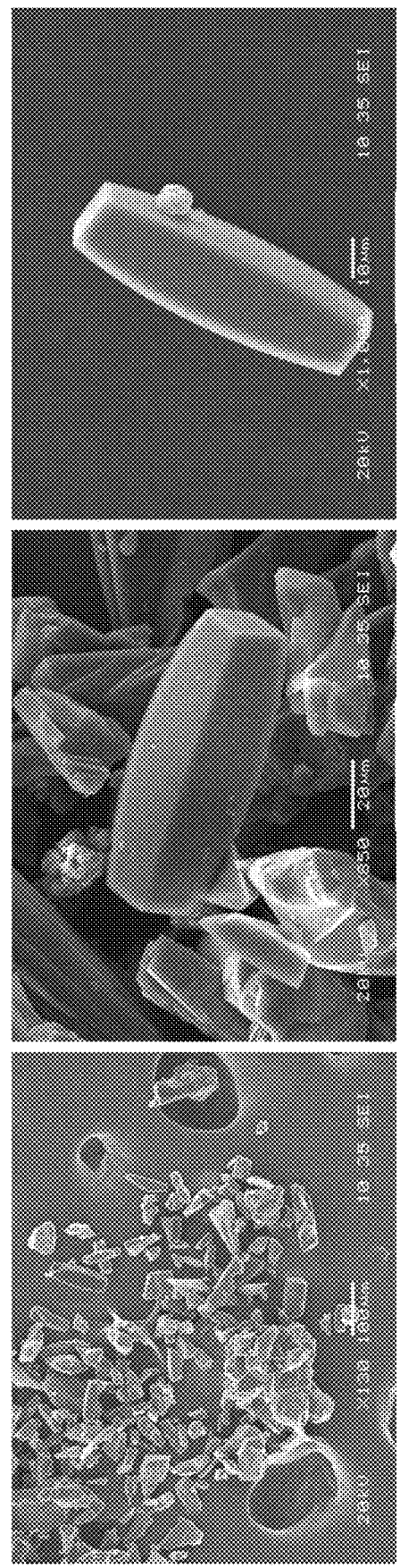
FIG. 5E shows scanning electron micrographs of (a) ALEN-Mg clusters and single crystals at a ×130 magnification, (b) single crystal view of ALEN-Mg over clusters at a ×850 magnification, and (c) an isolated single crystal of ALEN-Mg at a ×1,000 magnification.
Figure 6B:
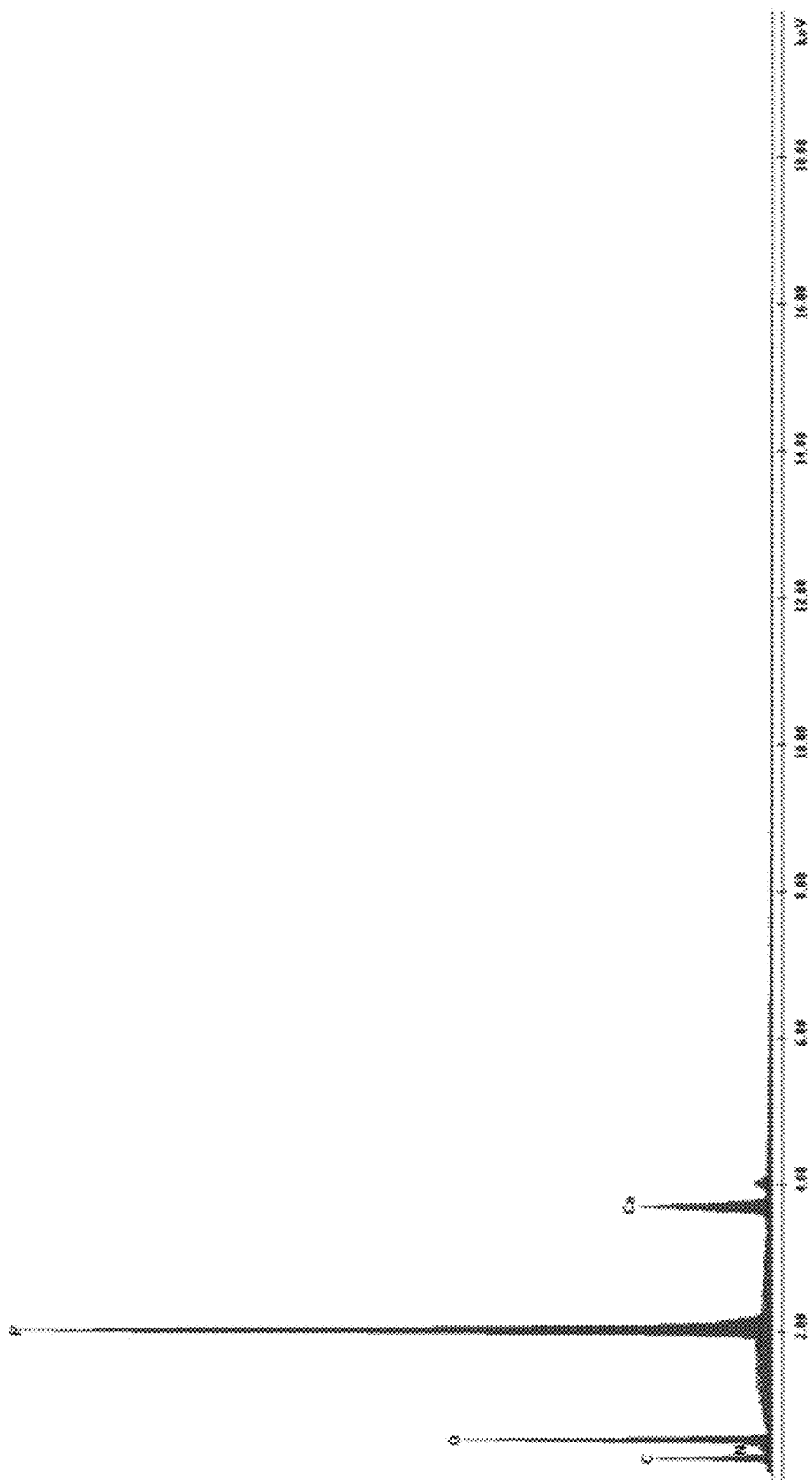
FIG. 6B shows energy dispersive spectra of ALEN-Ca form II complex displaying the presence of atoms (carbon, nitrogen, oxygen and phosphorous) present in the ligand and the metal (calcium).
Figure 6D:
FIG. 6D shows energy dispersive spectra of ALEN-Zn form II complex displaying the presence of atoms (carbon, nitrogen, oxygen and phosphorous) present in the ligand and the metal (zinc).
Figure 7B:
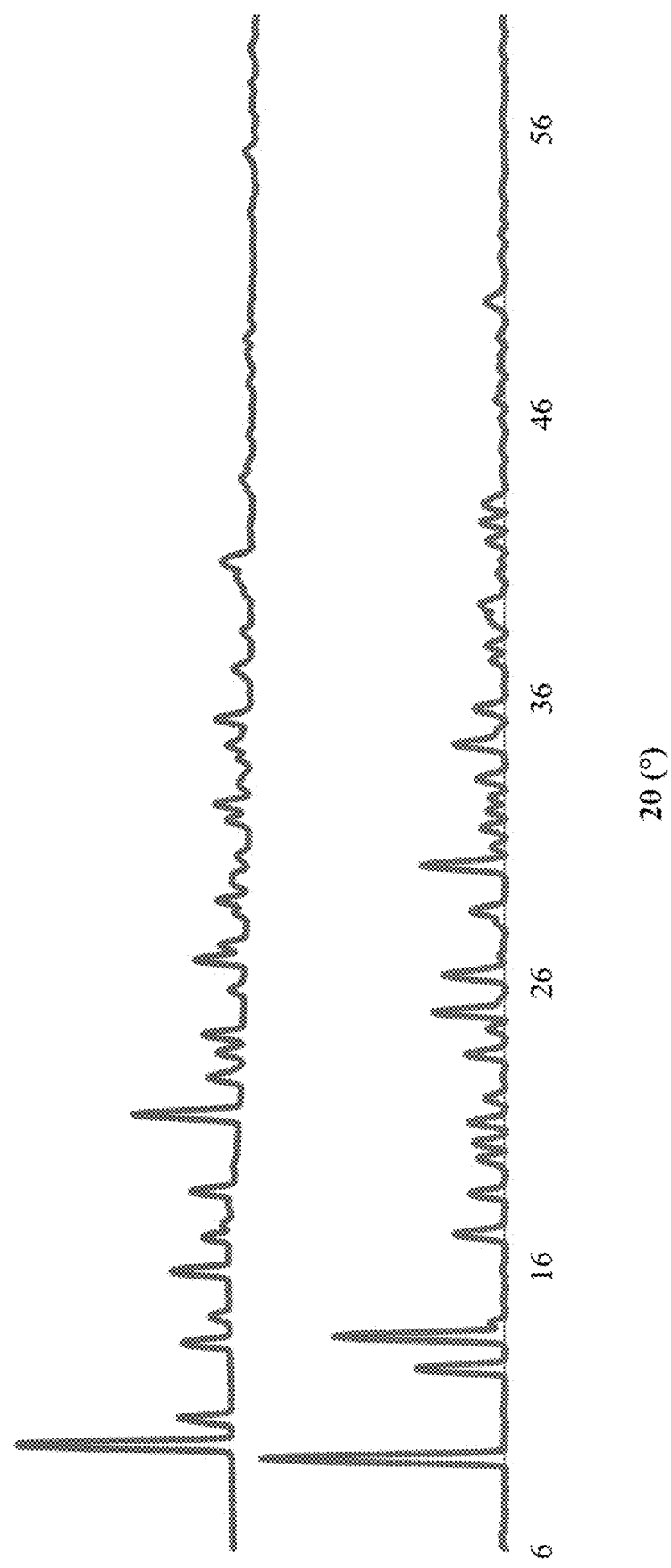
FIG. 7B shows powder X-ray diffractogram overlay of "as received" ALEN (bottom) and synthetized ALEN-Ca form II complex (top).
Figure 7C:
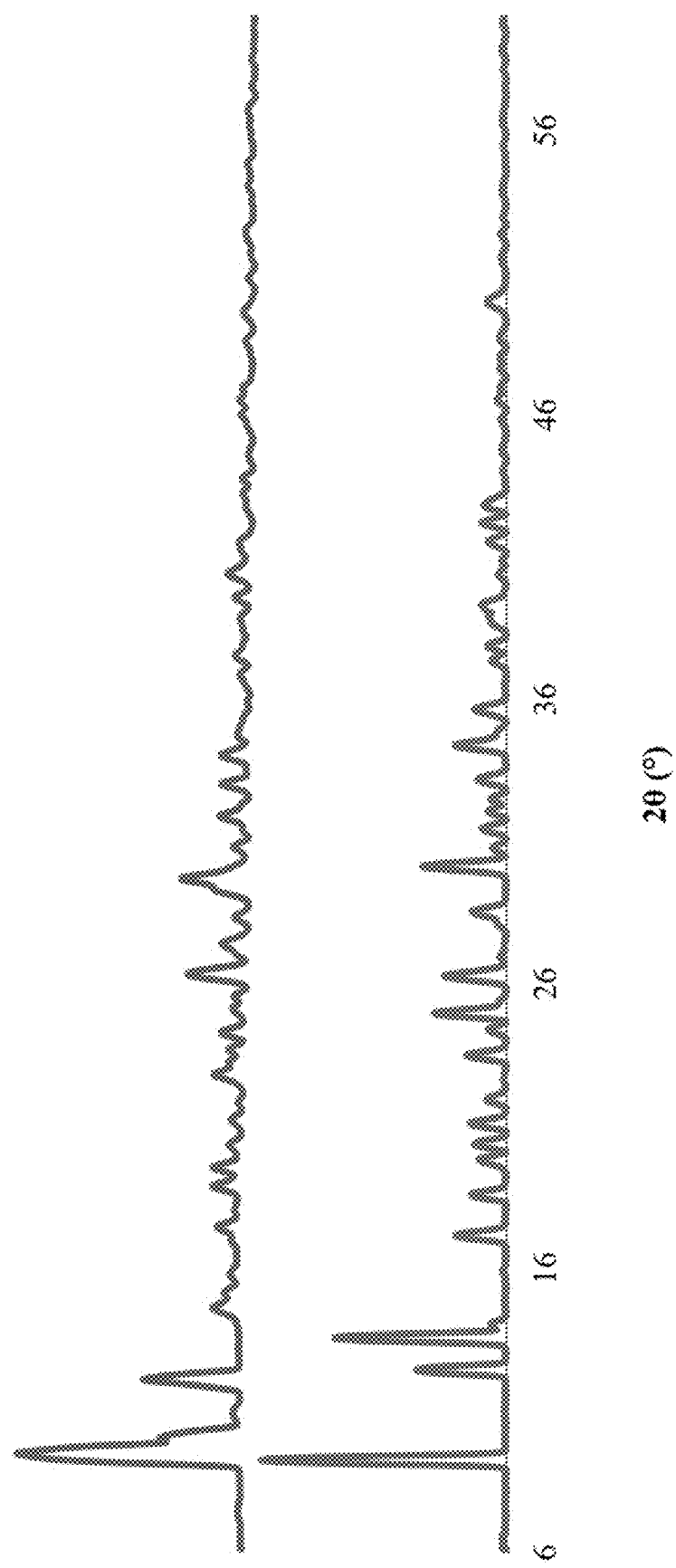
FIG. 7C shows powder X-ray diffractogram overlay of "as received" ALEN (bottom) and synthetized ALEN-Zn form I complex (top).
Figure 7D:
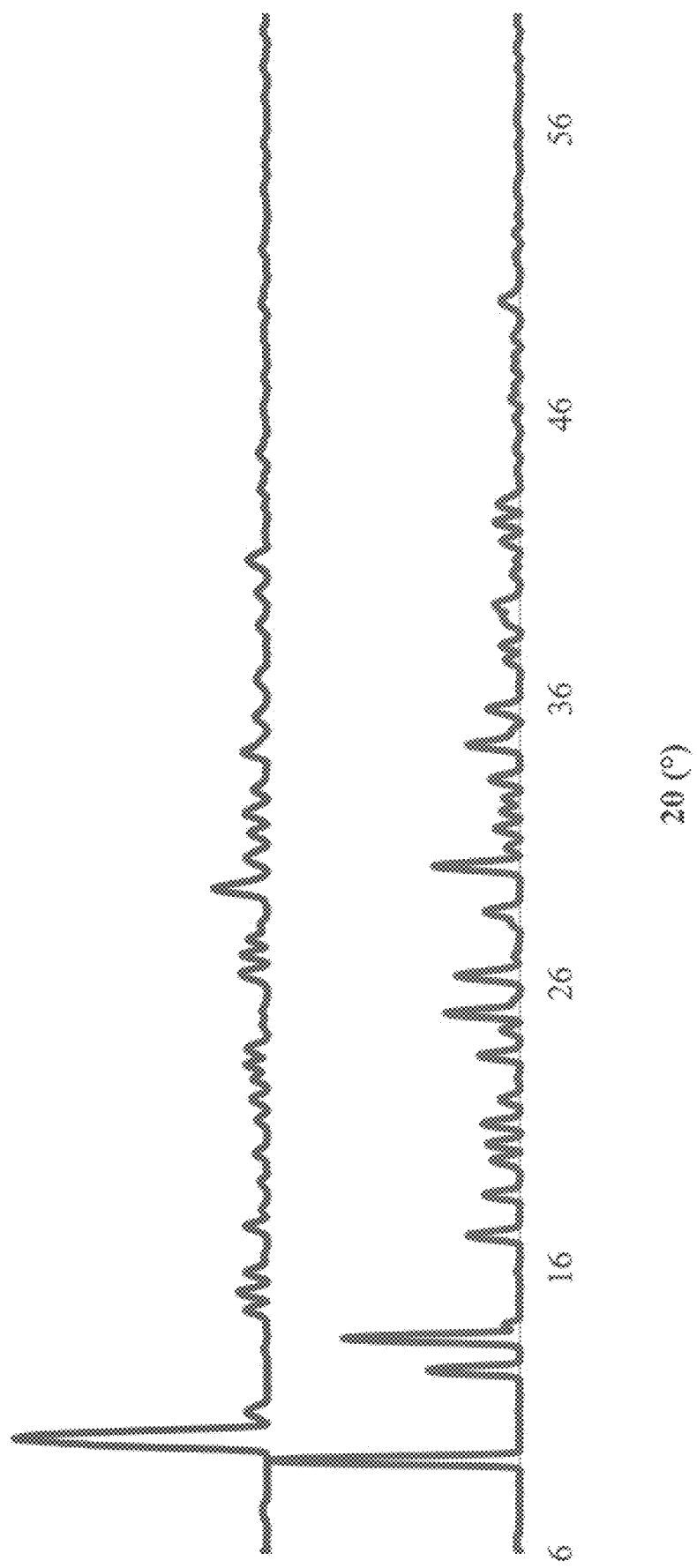
FIG. 7D shows powder X-ray diffractogram overlay of "as received" ALEN (bottom) and synthetized ALEN-Zn form II complex (top).
Figure 7E:
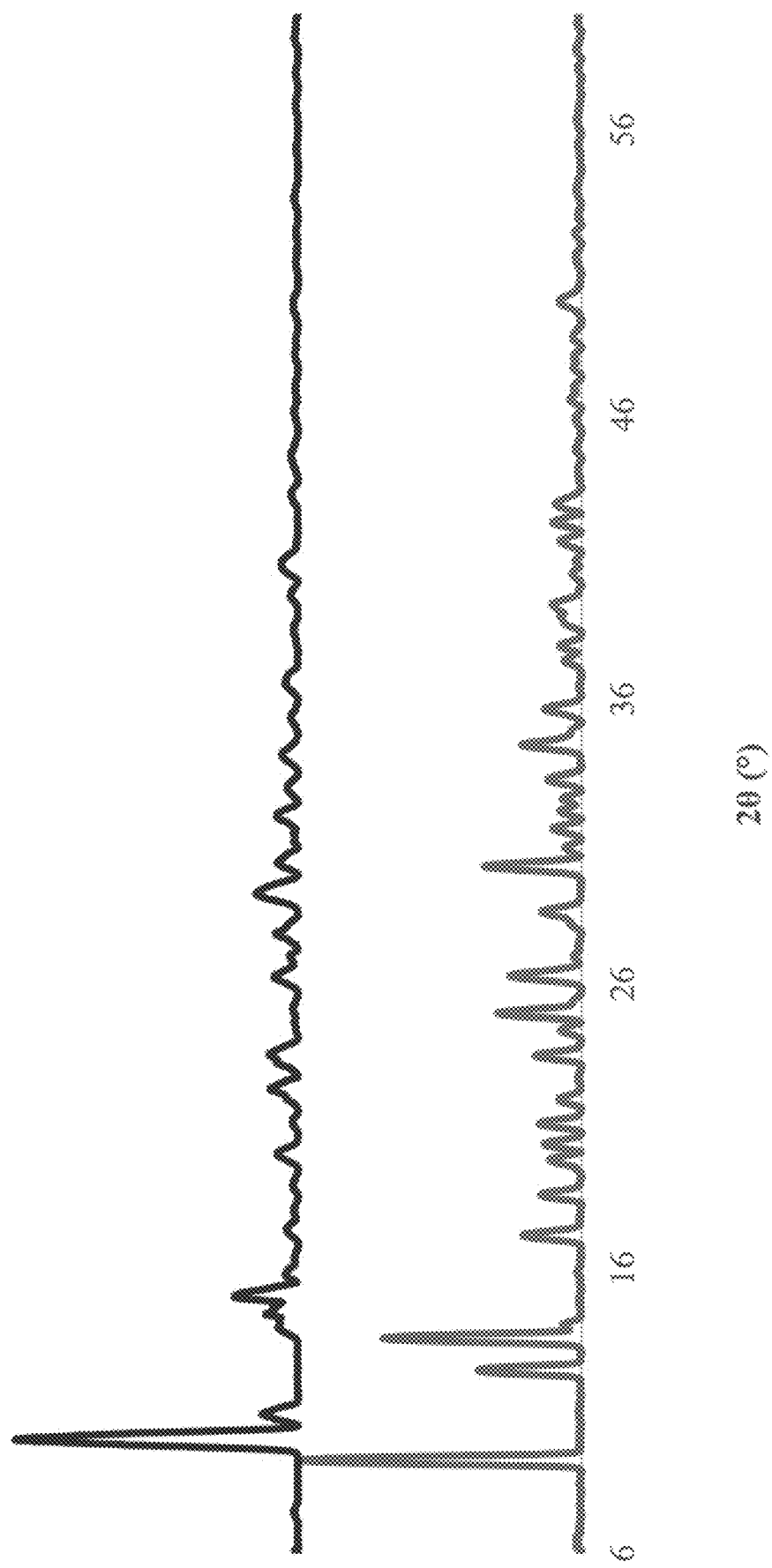
FIG. 7E shows powder X-ray diffractogram overlay of "as received" ALEN (bottom) and synthetized ALEN-Mg complex (top).
Figure 8A:
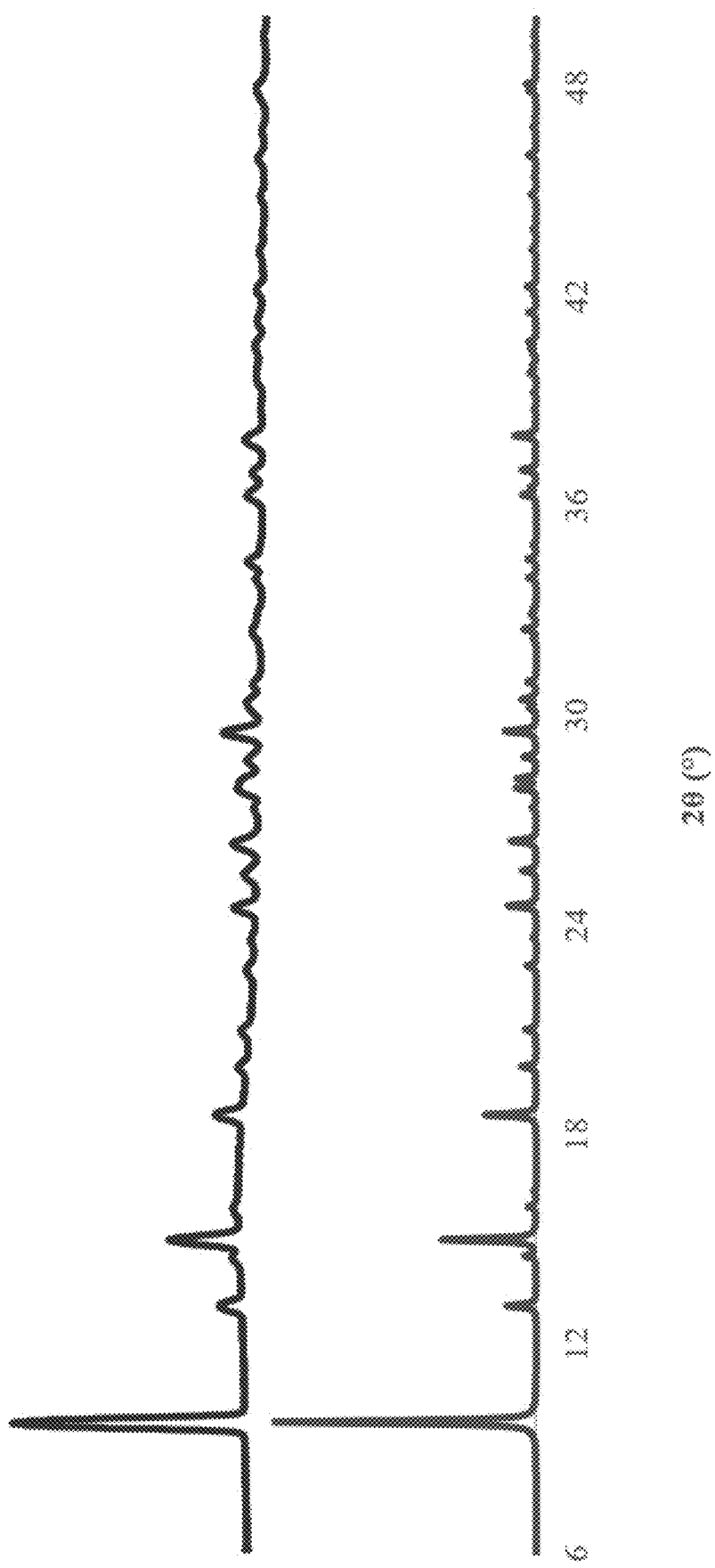
FIG. 8A shows simulated (bottom) and experimental (top) powder pattern overlay of ALEN-Ca form I complex.
Figure 8B:
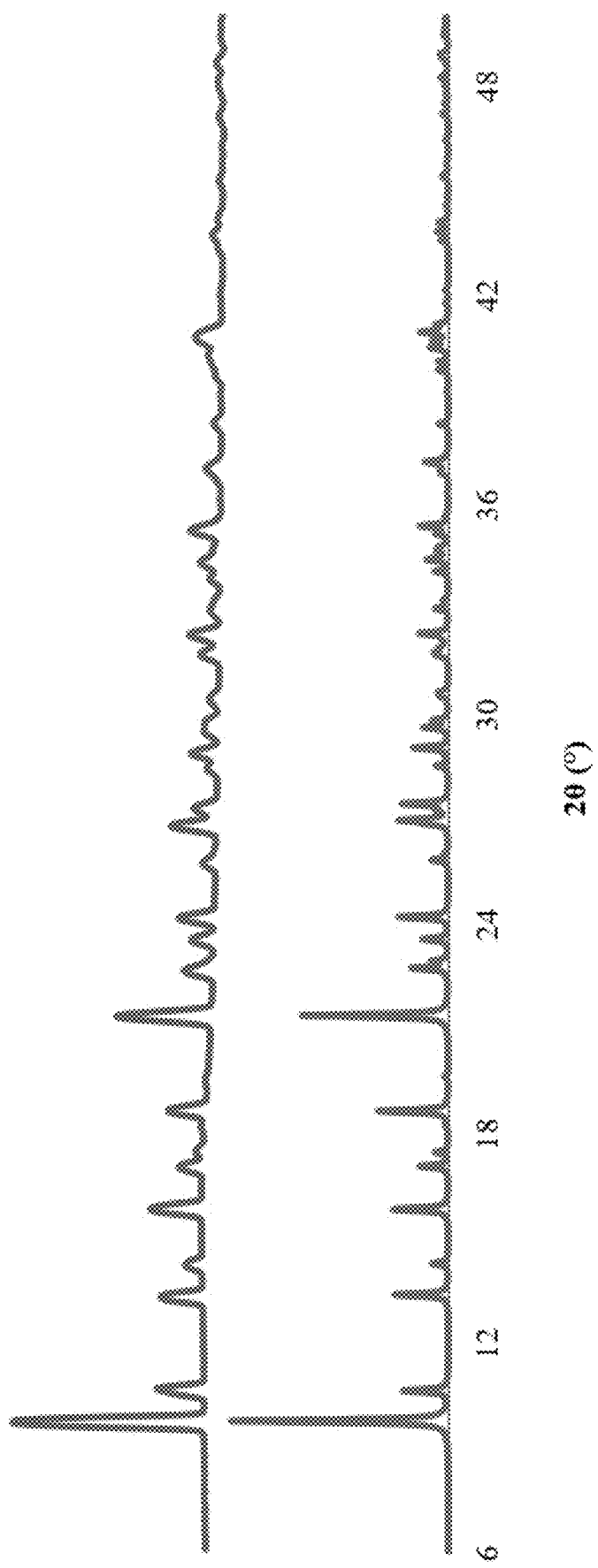
FIG. 8B shows simulated (bottom) and experimental (top) powder pattern overlay of ALEN-Ca form II complex.
Figure 8C:
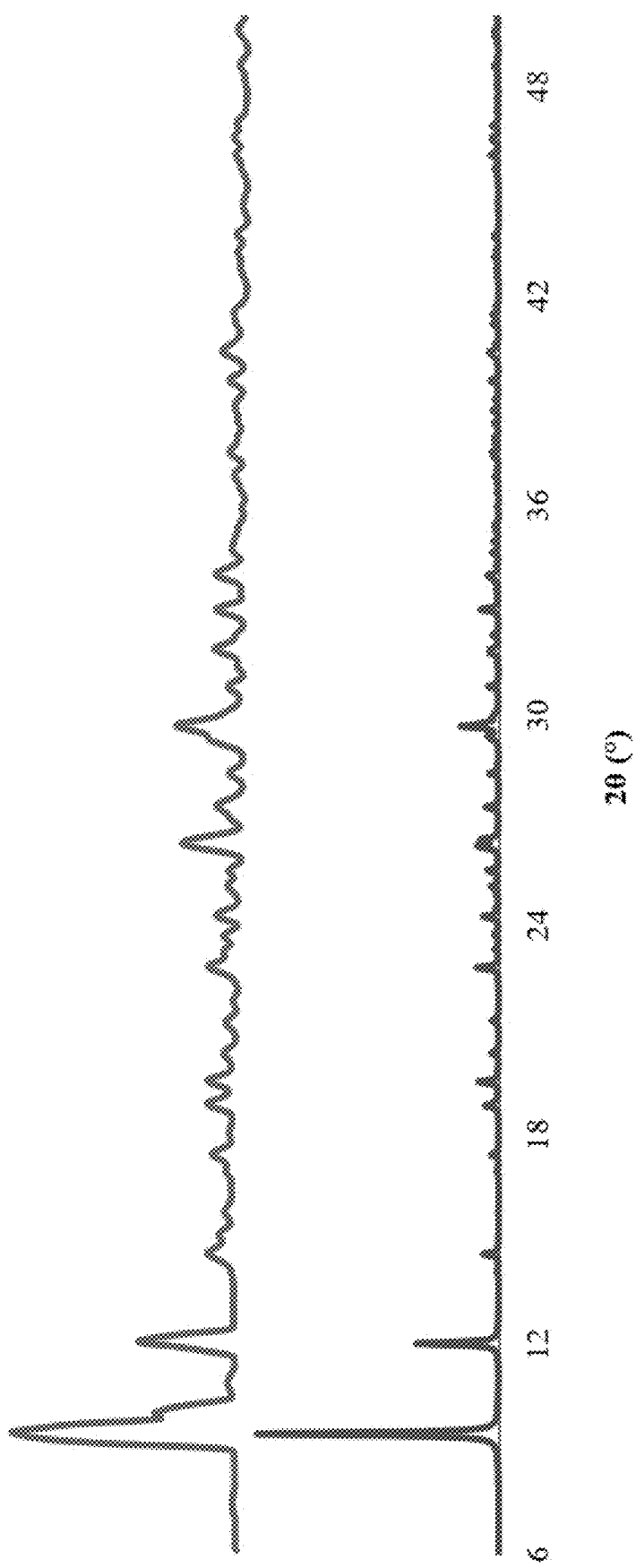
FIG. 8C shows simulated (bottom) and experimental (top) powder pattern overlay of ALEN-Zn form I complex.
Figure 8D:
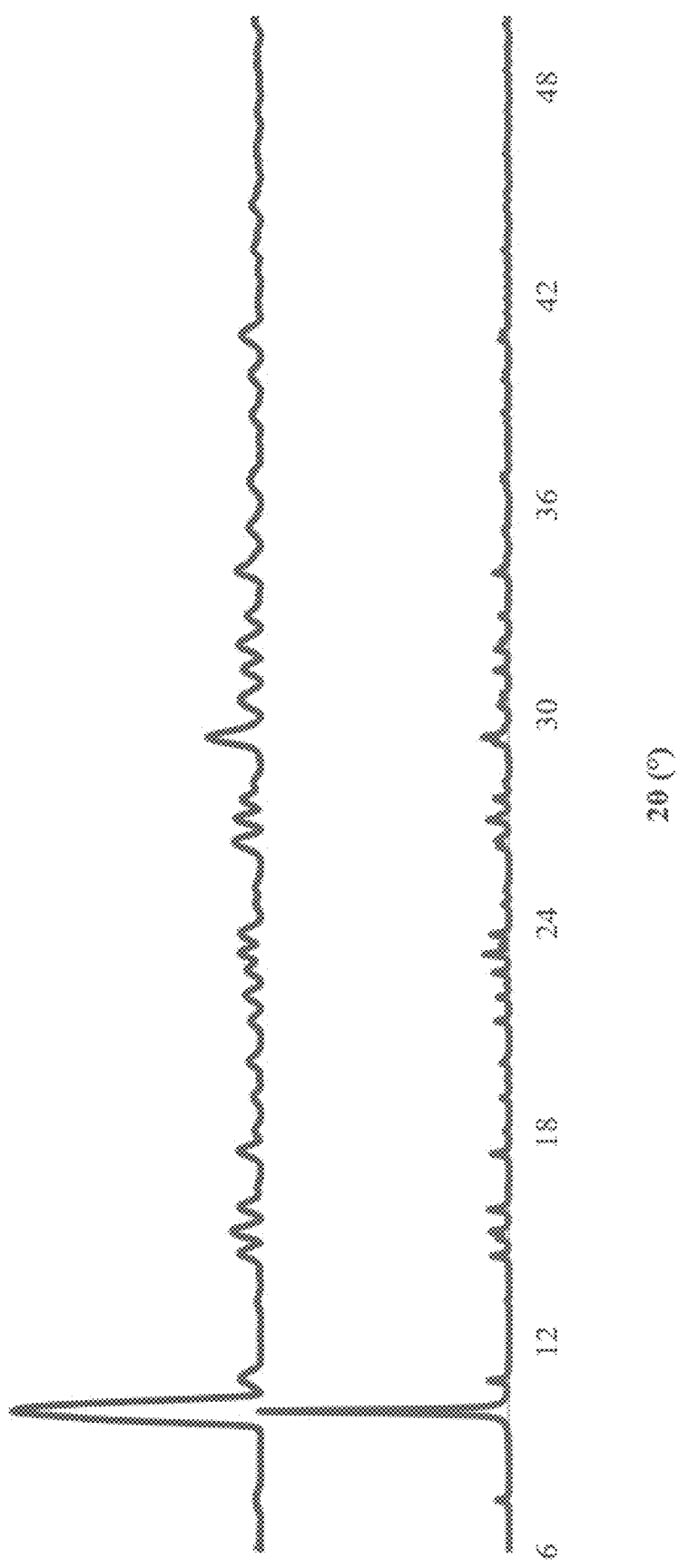
FIG. 8D shows simulated (bottom) and experimental (top) powder pattern overlay of ALEN-Zn form II complex.
Figure 8E:
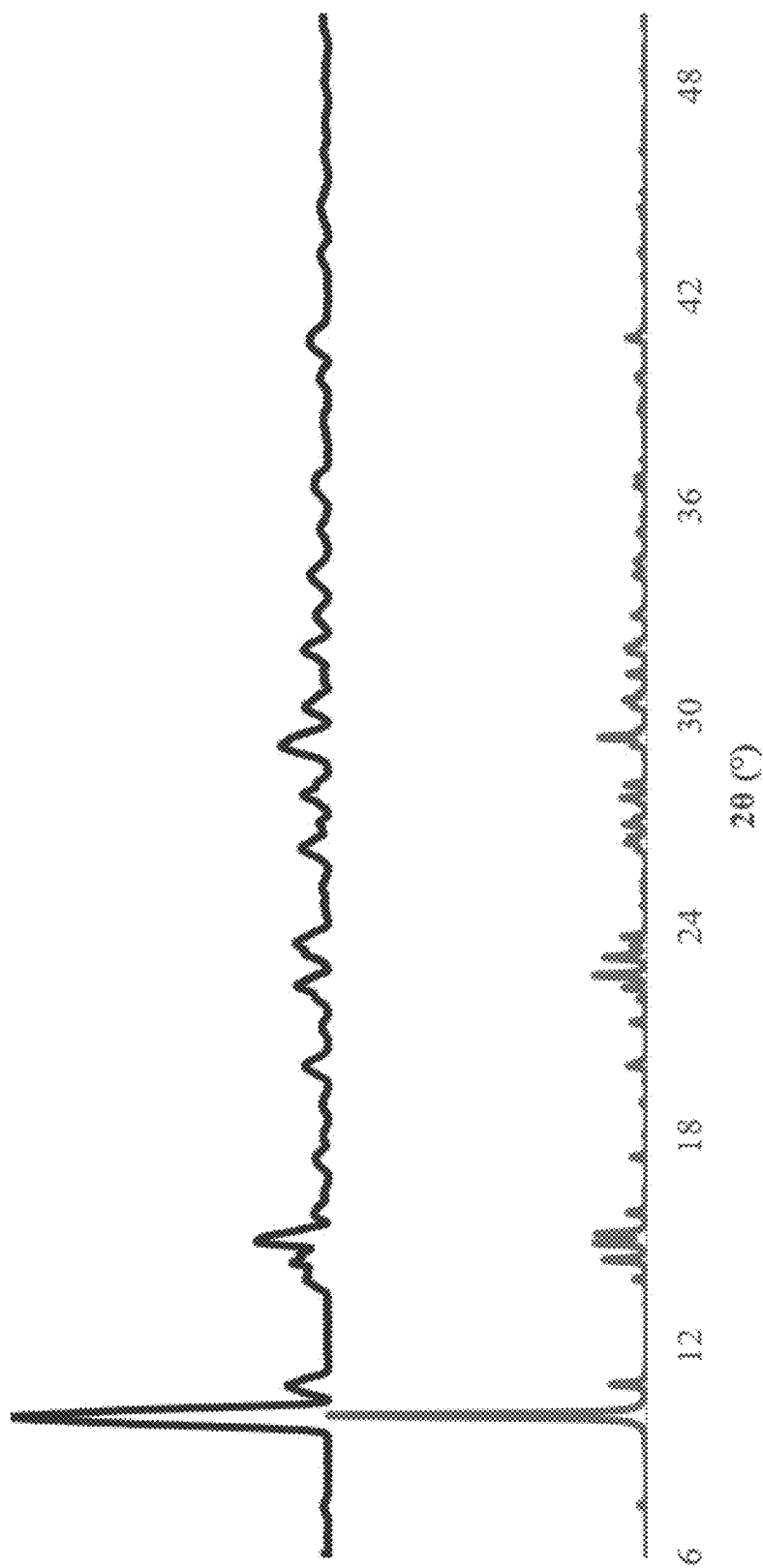
FIG. 8E shows simulated (bottom) and experimental (top) powder pattern overlay of ALEN-Mg complex.

Representative Raman spectra for the isolated products of the hydrothermal synthesis between ALEN and bioactive metals ($Ca^{2+}$, $Zn^{2+}$ and $Mg^{2+}$) presetting the highest quality single crystals, between 3,600 and 100 $cm^{-1}$, were collected and are shown in FIG. 4. Raman spectra of the BP ligand, metal salts, as well as the corresponding product for the hydrothermal syntheses were analyzed in order to assign specific Raman active vibrational modes useful for the determination of the BP ligand mode of coordination. When compared, the Raman spectra of the metal and BP ligand employed in the hydrothermal synthesis and the product, the presence and absence of characteristic Raman shifts were observed indicating a distinctive solid-form had been produced. Among the five phases, significant differences are observed in the Raman spectra. These differences occurred particularly in the 2,800-2,650 $cm^{-1}$ region, where characteristic bands can be assigned to the presence of hydrogen phosphate, H—$OPO_2$C moieties. Raman shifts between 3,600-3,200 $cm^{-1}$ are assigned to the vO—H/$H_2O$ stretching vibrations of different moieties: hydroxyl groups of the BP ligand, coordinated, and lattice water molecules (FIG. 4). These suggest that extensive hydrogen bonding might be present in these pBioCCs. The broadening and splitting of these bands indicate the presence of several types of strong hydrogen bonds (~3200 $cm^{-1}$) within each lattice. The presence of the BP ligand in the molecular structure of the product in the hydrothermal synthesis is confirmed by two bands at 1,100 $cm^{-1}$ (medium) and 1,046 $cm^{-1}$ (strong), respectively, which are characteristic bands for both the $v^{as}$P—O(H) asymmetric stretching vibrations and the δPO—H bending of the phosphonate P—$O_3$ groups. The band at around 1,140-1,160 $cm^{-1}$ is characteristic of vP=O/δ"POH stretching vibrations. The band at 1,260 $cm^{-1}$ may be attributed to the P=O deformation vibration. Similarly, to the asymmetric stretching vibration of the P—O bonds, Raman shifts between 930-1,000 cm$^{-1}$ correspond to the symmetric v$^s$P—O(H) stretching vibrations. Different vibrational modes of coordination of the divalent metal ions (M$^{2+}$) with phosphorous bonded oxygen atoms, induce changes in the P—O bond order, generating the differences observed in the symmetric and asymmetric P—O(H) stretching vibrations among the pBioCCs and the ligand. Other bands located at lower wavenumbers (<1,000 cm$^{-1}$) correspond to vibrational modes characteristics of the CH$_2$, C—C, C—P, C—OH and M-O groups and are also present in the Raman spectra of the isolated ALEN-based metal complexes.

Morphological and Elemental Analysis of the ALEN-Based Metal Complexes

To assess the morphology and basic composition of the yielded crystalline materials, analysis with a scanning electron microscope coupled with energy dispersive X-ray spectroscopy (SEM-EDS) was performed. Representative SEM images (FIGS. 5A-5E) collected for the isolated crystalline phases show crystals with well-defined morphologies. SEM images indicate that the diameter of the resulting crystals range between 10-100 μm. The EDS spectra of these materials exhibit the characteristic signals of the metal and other elements, which are present in the molecular structure of the BP (carbon, nitrogen, phosphorous, and oxygen atoms), and had been employed in the hydrothermal reactions (FIGS. 6A-6E). Micrographs and X-ray microanalysis (SEM-EDS) were recorded with a JEOL JSM-6480LV scanning electron microscope with an Evenhart Thomley secondary electron imagining (SEI) detector. Images were taken with an acceleration voltage of 20 kV, an electron beam of 11 mm width, with a spot size value of 36, SEI signal and HV vacuum mode. These results along with the Raman spectra analysis support, thus far, that the hydrothermal reactions have produced four crystalline phases that are distinct from the starting materials employed in the hydrothermal reactions.

Powder X-Ray Diffraction Analysis of the ALEN-Based Metal Complexes

Powder X-ray diffraction (PXRD) was employed to assess the crystallinity of the products for the hydrothermal syntheses between ALEN (as shown in FIG. 1) and bioactive metals (Ca$^{2+}$, Zn$^{2+}$, and Mg$^{2+}$). Many of the hydrothermal synthesis spontaneously formed microcrystalline powders, interestingly; in most of these cases Mg$^{2+}$ was employed as the bioactive metal. Accordingly, we focus on the powder micro-diffraction analysis of four phases that presented the highest crystal quality as suggested by polarized optical microscopy (FIG. 3). The observation of low amorphous background in each of the diffractograms of the isolated phases confirms a high degree of crystallinity (FIGS. 7A-7E) for the isolated products of the hydrothermal synthesis. Moreover, PXRD analysis was utilized to confirm that these phases were not produced by the concomitant recrystallization of the metal salt or the BP ligand employed in each of the hydrothermal reactions. Based on the differences in the powder X-ray diffractograms when the starting materials and the products of the hydrothermal syntheses were compared, the formation of distinctive crystalline phases can be sustained. Additionally, the isolated products of the hydrothermal synthesis were compared to the previously reported structures as demonstrated herein. The absence of low angle peaks (<5° in 2θ) suggests that these are dense or 2D layered materials and not 3D porous networks. Table 1 below lists the Powder X-ray Diffraction (PXRD) prominent 2θ peaks of the coordination complexes as shown in FIGS. 7A-7E. Prominent 2θ peaks from the diffractograms where selected qualitatively based on their intensities. Peaks between 6°-24° where took in consideration as the most important and characteristics ones that describe the crystal structure on the complexes. High intensity peaks are described qualitatively as twice or more the size or intensity when compared to the others. Low intensity peaks were selected as prominent if they were isolated through the spectra in the range mentioned before. It is to be understood that a specified 2θ angle means the specified value ±0.1°.

TABLE 1

| Coordination Complex | Prominent 2θ peaks (°) | | | | | |
|---|---|---|---|---|---|---|
| | Peak 1 | Peak 2 | Peak 3 | Peak 4 | Peak 5 | Peak 6 |
| ALEN-Ca I | 9.76 | 13.10 | 14.98 | 18.54 | 19.92 | 20.94 |
| ALEN-Ca II | 9.78 | 10.64 | 13.38 | 15.82 | 18.64 | 21.40 |
| ALEN-Mg | 10.46 | 10.88 | 14.46 | 19.96 | 22.60 | 23.08 |
| ALEN-Zn I | 9.44 | 12.04 | 14.64 | 17.42 | 18.89 | 19.54 |
| ALEN-Zn II | 10.02 | 10.86 | 14.46 | 15.14 | 15.78 | 17.38 |

Structural Description of the ALEN-Based Metal Complexes

To provide unambiguous evidence for the formation of the five pBioCCs according to the invention, elucidation of their crystal structure was performed using single crystal X-ray diffraction. The crystal structures were collected at low temperature (100 K) and solved using direct methods. Summary of the crystallographic parameters of the structure refinements of each crystalline phase analyzed are summarized in Table 2 below for the isolated pBioCCs; (a) ALEN-Ca form I, (b) ALEN-Ca form II, (c) ALEN-Zn form I, (d) ALEN-Zn form II, and (e) ALEN-Mg. PXRD overlays of the calculated powder patterns against the experimental powder patterns for each crystalline phase (FIGS. 8A-8E) corroborates that a representative solution has been found, and that these were obtained as pure phases.

TABLE 2

| Compound | ALEN-Ca form I | ALEN-Ca form II | ALEN-Zn form I | ALEN-Zn form II | ALEN-Mg |
|---|---|---|---|---|---|
| Empirical formula | Ca[C$_4$H$_{13}$NO$_8$P$_2$] | Ca[C$_8$H$_{24}$N$_2$O$_{14}$P$_4$] | Zn[(C$_4$H$_{11}$NO$_7$P$_2$)(H$_2$O)] | Zn$_2$[C$_{16}$H$_{12}$NO$_7$P$_2$(H$_2$O)$_2$]·2H$_2$O | Mg$_2$[C$_{16}$H$_{12}$N$_2$O$_7$P$_2$(H$_2$O)$_2$]·2H$_2$O |
| FW (g/mol) | 305.17 | 536.25 | 330.46 | 1183.73 | 1079.2 |
| Space group | Pna2$_1$ | I 2/a | P 2$_1$/n | P 2$_1$/c | P 2$_1$/c |
| Temperature (K) | 100.00 | 100.01 | 100.00 | 100.00 | 100.00 |
| λ (Å) | 1.54184 | 1.54184 | 0.71073 | 1.54184 | 1.54184 |
| a (Å) | 13.5226 | 11.40590 | 5.4734 | 12.5411 | 12.5466 |
| b (Å) | 12.1976 | 12.38480 | 14.7092 | 13.42828 | 13.3994 |
| c (Å) | 6.75490 | 13.46860 | 12.2579 | 12.4120 | 12.4156 |
| α(°) | 90 | 90 | 90 | 90 | 90 |

TABLE 2-continued

| Compound | ALEN-Ca form I | ALEN-Ca form II | ALEN-Zn form I | ALEN-Zn form II | ALEN-Mg |
|---|---|---|---|---|---|
| $\beta(°)$ | 90 | 101.3320 | 98.003 | 109.437 | 109.243 |
| $\gamma(°)$ | 90 | 90 | 90 | 90 | 90 |
| V (Å$^3$) | 1114.18 | 1865.48 | 977.264 | 1971.13 | 1970.65 |
| Z | 4 | 4 | 4 | 2 | 2 |
| $\rho_{calc}$ (g/cm$^3$) | 1.819 | 1.909 | 2.246 | 1.455 | 1.876 |
| Rwp | 0.1156 | 0.0901 | 0.0839 | 0.0461 | 0.1916 |
| Rp | 0.0416 | 0.0345 | 0.0381 | 0.0453 | 0.0660 |

Structural Description

Figure 9A:
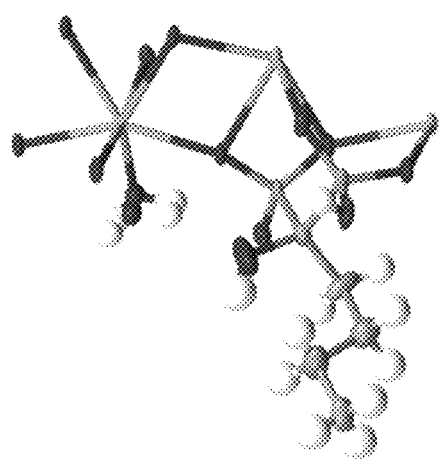
FIG. 9A shows the molecular structure of (a) the asymmetric unit and (b) crystalline packing of ALEN-Ca form I complex along a-axis.
Figure 9A:
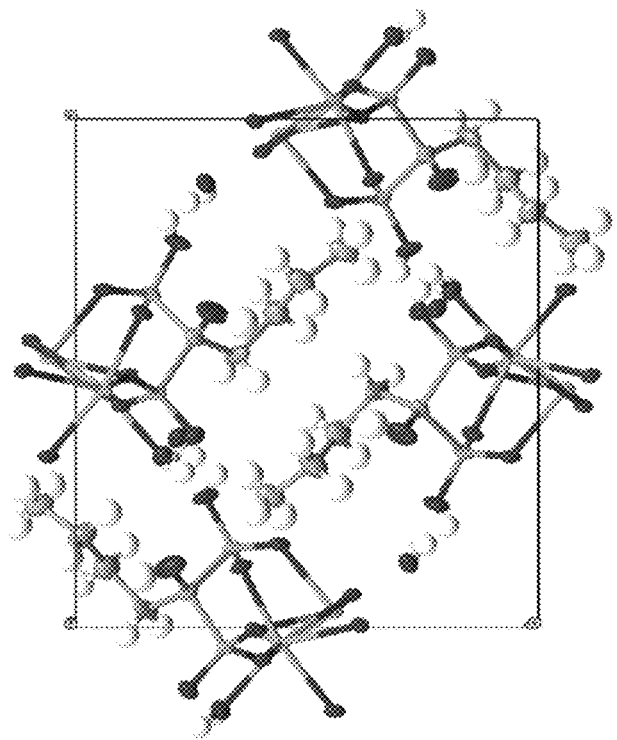
Figure 9B:
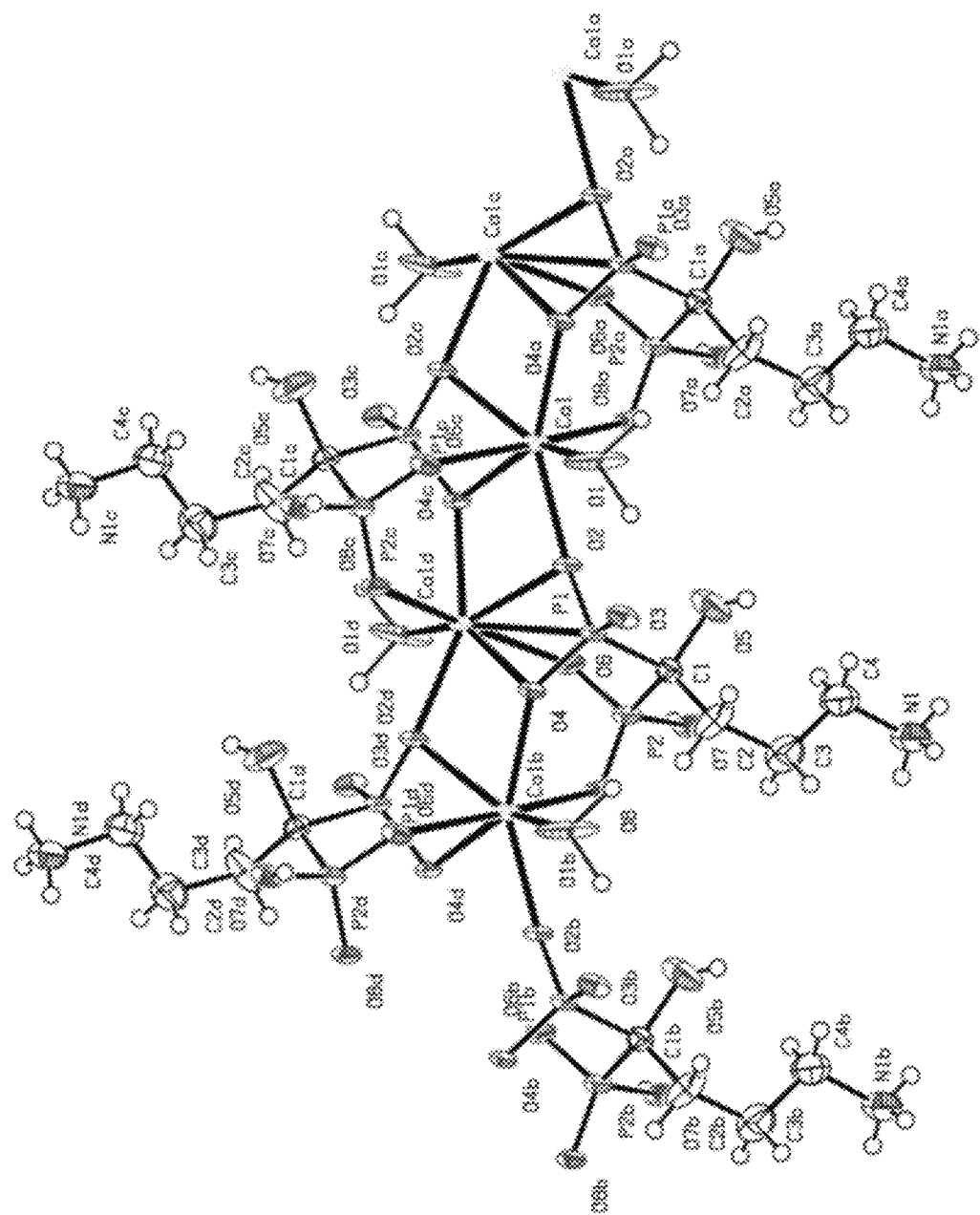
FIG. 9B shows a ball-stick representation (atoms labeled) showing the connectivity between Ca and ALEN ligands to form the ALEN-Ca form I coordination complex.

ALEN-Ca Form I:

The compound [Ca(C$_4$H$_{11}$NO$_7$P$_2$)(H$_2$O)] crystallizes in the orthorhombic space group Pna2$_1$, with the asymmetric unit containing a single independent calcium atom. The ligands coordinate to three calcium atoms. The seven-fold calcium atoms are coordinated by six oxygen atoms from six symmetry-related alendronate ligands and a water molecule. Even though the water molecule acts as a terminal ligand, the alendronate ligands act as pillars linking neighboring calcium atoms forming a 3D framework containing 1D inorganic chains that stacked tilted along the c-axis. A single intramolecular hydrogen bond between oxygen of the ligand and the terminal water molecule (O2 . . . O8=2.891 Å) reinforces the propagation of the 1D chains motif. Adjacent chains are bound by a series of intermolecular hydrogen bonds, on one side between the amine nitrogen and the oxygen atom of the alendronate ligand (O2 . . . N1=3.020 Å) and by several intermolecular hydrogen bonds on the other side. (O5 . . . N1=2.839 Å and O6 . . . N1=2.848 Å, O2 . . . O7=2.464 Å, O7 . . . O8=2.670 Å). The hydrogen bond network helps to expend the 3D framework along the ab-plane. FIGS. 9A and 9B show the molecular structure and a ball-stick representation of the structure, respectively.

Figure 10A:
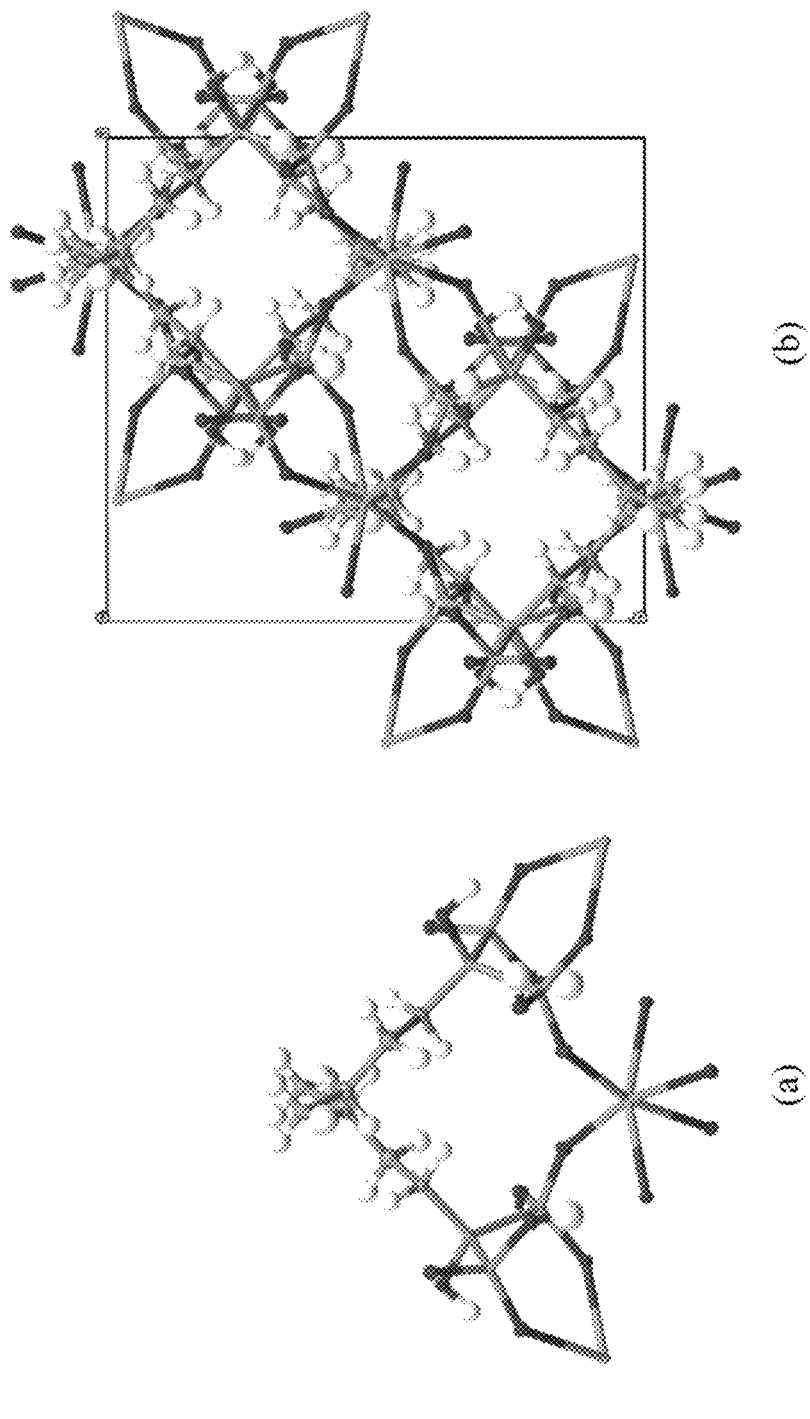
FIG. 10A shows the molecular structure of (a) the asymmetric unit and (b) crystalline packing of ALEN-Ca form II complex along a-axis.
Figure 10B:
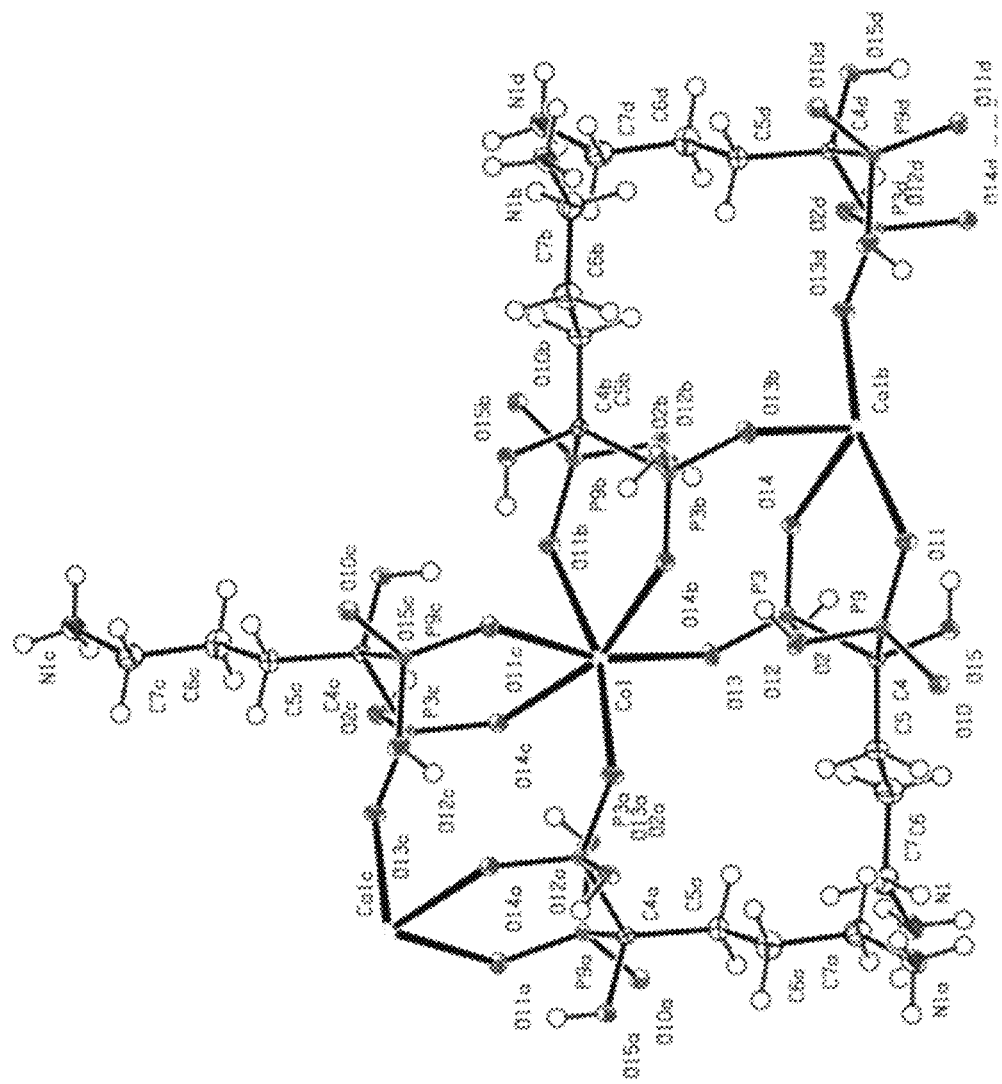
FIG. 10B shows a ball-stick representation (atoms labeled) showing the connectivity between Ca and ALEN ligands to form the ALEN-Ca form II coordination complex.

ALEN-Ca form II:

The compound [Ca(C$_4$H$_{12}$NO$_7$P$_2$)] crystallizes in the I2/a space group with the asymmetric unit containing a single independent calcium atom. The calcium atom has a strongly distorted octahedral environment with the O—Ca—O bond angles ranging from 82.32° to 105.28°. The Ca—O bond distances range between 2.288 Å and 2.343 Å. The six-fold calcium atoms are coordinated by six oxygen atoms from six symmetry-related alendronate ligands. No coordinated water or lattice waters are present in this structure unlike the structure found for ALEN-Ca form I. The alendronate ligands act in the structure as pillars linking neighboring calcium atoms forming a 3D framework containing 1D inorganic chains that stacked tilted along the a-axis. An intramolecular hydrogen bond between one of the coordinated phosphonate oxygen atom and hydroxyl group of the ligand (O11 . . . O15=2.837 Å), stabilizes the metal cluster and helps propagates the 1D chains. Adjacent chains are reinforced by two district intermolecular hydrogen bonds one between the amine nitrogen and hydroxyl group of the ligand (N1 . . . O15=3.006 Å), and the other between the amine nitrogen and one of the coordinated phosphonate oxygen atom (N1 . . . O10=2.687 Å) on either one side of the 1D chains which propagate into a 3D framework along the bc-plane. FIGS. 10A and 10B show the molecular structure and a ball-stick representation of the structure, respectively.

Figure 11A:
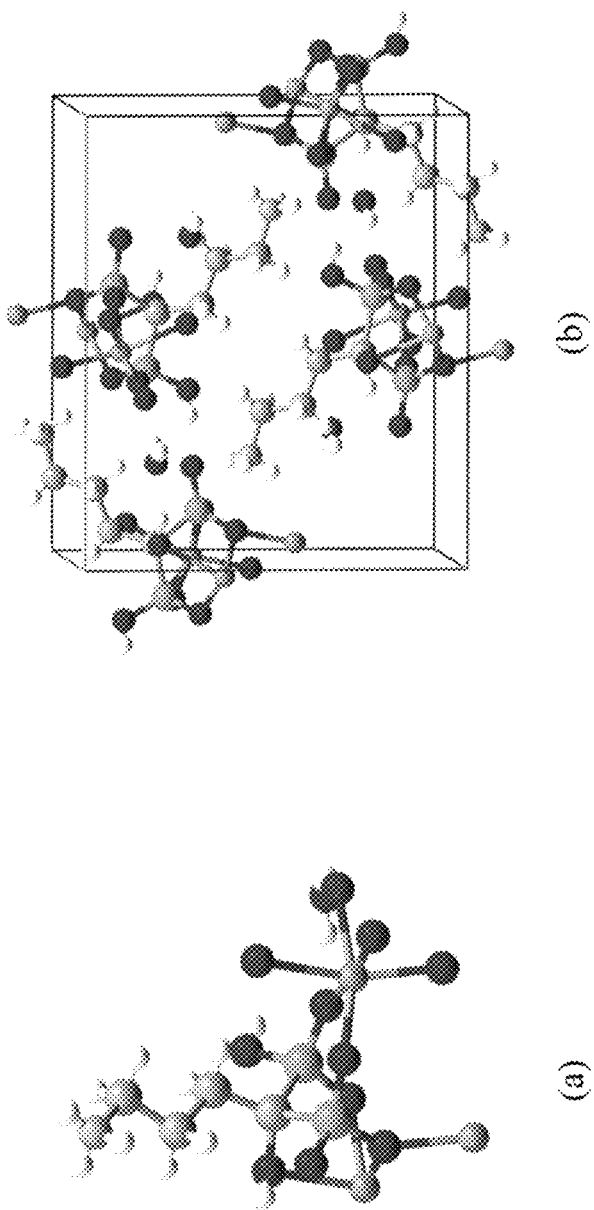
FIG. 11A shows the molecular structure of (a) the asymmetric unit and (b) crystalline packing of ALEN-Zn form I complex along a-axis.
Figure 11B:
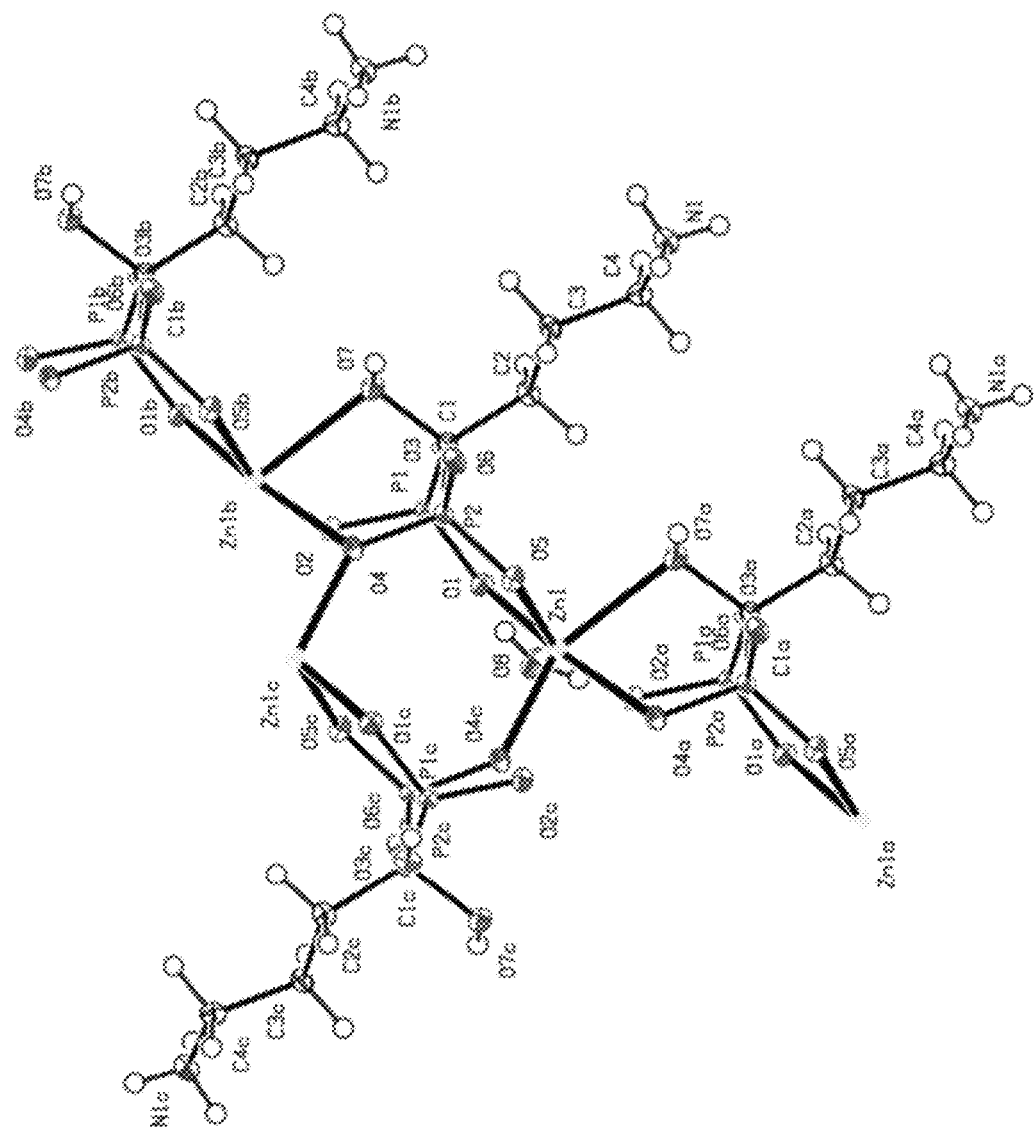
FIG. 11B shows a ball-stick representation (atoms labeled) showing the connectivity between Zn and ALEN ligands to form the ALEN-Zn form I coordination complex.

ALEN-Zn Form I:

The compound [Zn(C$_4$H$_{11}$NO$_7$P$_2$)(H$_2$O)] represents an additional crystalline phase to that originally published for the ALEN-Zn complex. The present structure for ALEN-Zn is isostructural to a recently published metal-phosphonate complex displaying manganese metal center and alendronate as ligand. The ALEN-Zn complex is defined by the P2$_1$/n space group and has one molecule in the asymmetric unit. The zinc atom has a strongly distorted octahedral environment with the O—Zn—O bond angles ranging from 74.74° to 107.24°. The Zn—O bond distances are between 1.972 and 2.353 Å. The ligand, ALEN, bridges the Zn(II) ions into an infinite single chain through four phosphonate oxygens and the hydroxyl oxygen. Inter-chain hydrogen bonds help form a 3D network structure with channels generated along the a-axis. The protonated amine tails and the lattice water reside in the channels and are held in position by intricate systems of hydrogen bonds. FIGS. 11A and 11B show the molecular structure and a ball-stick representation of the structure, respectively.

Figure 12A:
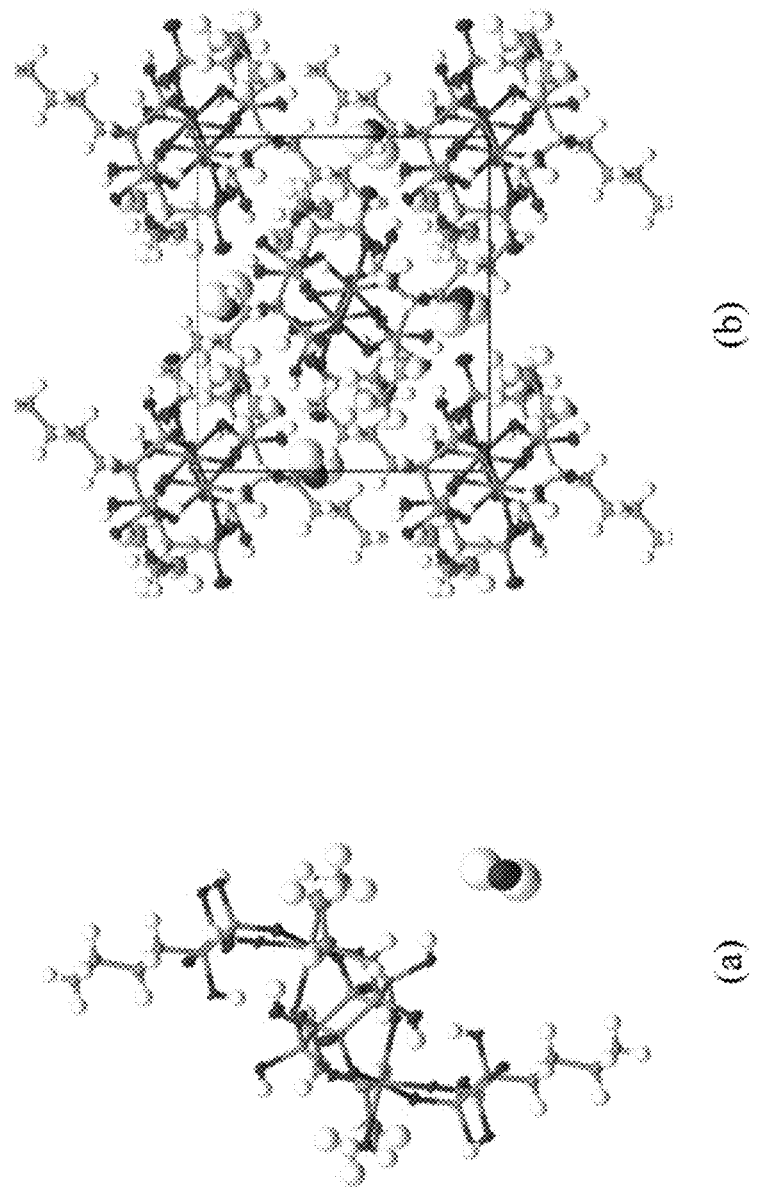
FIG. 12A shows the molecular structure of (a) the asymmetric unit and (b) crystalline packing of ALEN-Zn form II complex along a-axis.
Figure 12B:
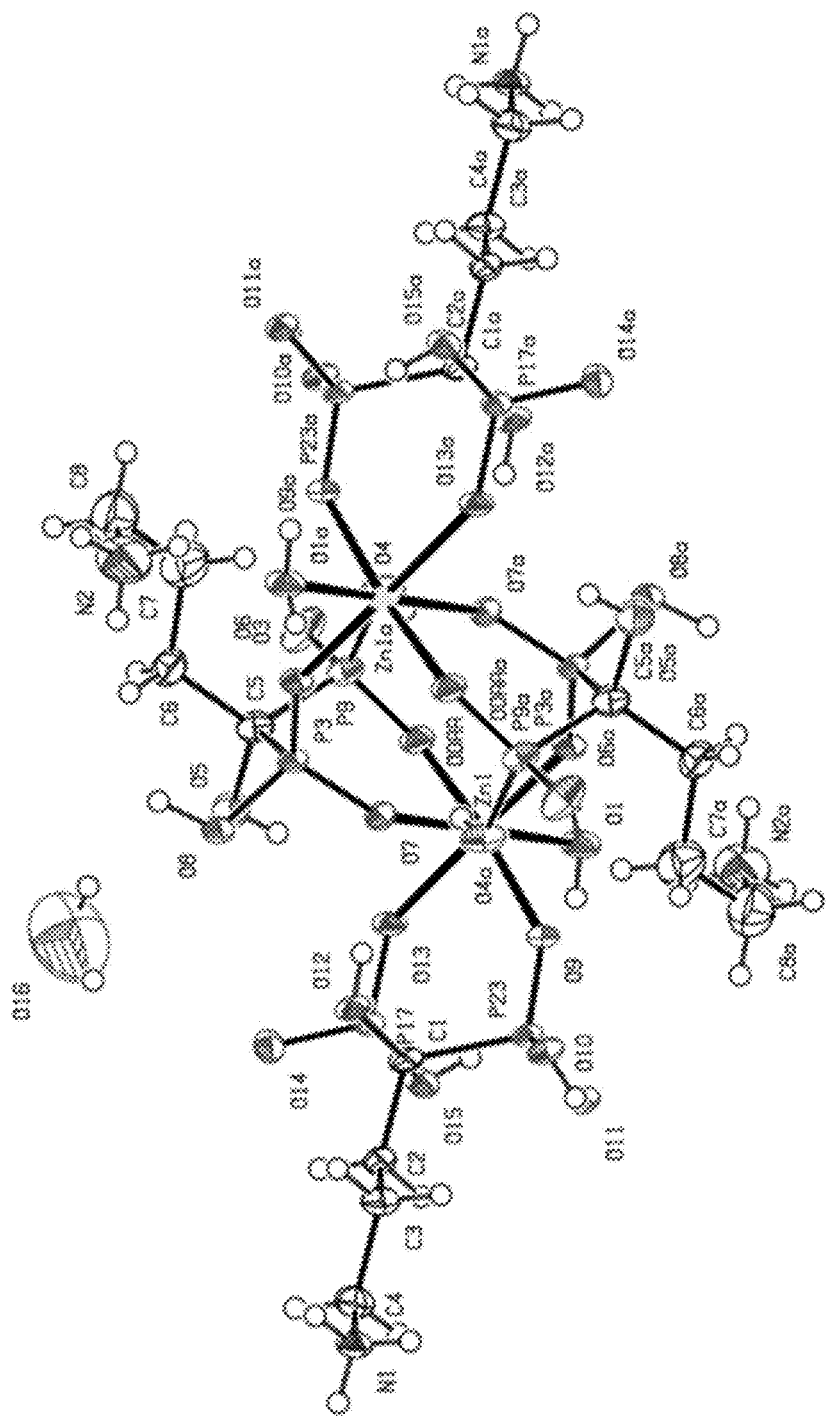
FIG. 12B shows a ball-stick representation (atoms labeled) showing the connectivity between Zn and ALEN ligands to form the ALEN-Zn form II coordination complex.

ALEN-Zn Form II:

The compound Zn$_2$[C$_{16}$H$_{52}$N$_4$O$_{30}$P$_{82}$(H$_2$O)] represents an additional crystalline phase from the previously discussed phase ALEN-Zn form I. ALEN-Zn form II is a redetermination of a published structure at lower temperature and present a lower error in the refinement. ALEN-Zn form II is defined by the P2$_1$/c space group and has one molecule in the asymmetric unit. The zinc atom has a strongly distorted octahedral environment with the O—Zn—O bond angles ranging from 82.38° to 178.59°. The Zn—O bond distances are between 2.013 and 2.156 Å. The ligand, ALEN, bridges the Zn(II) ions into an infinite single chain through four phosphonate oxygens and the hydroxyl oxygen. Inter-chain hydrogen bonds help form a 3D network structure with channels generated along the a-axis. The protonated amine tails and the lattice water reside in the channels and are held in position by intricate systems of hydrogen bonds. FIGS. 12A and 12B show the molecular structure and a ball-stick representation of the structure, respectively.

Figure 13A:
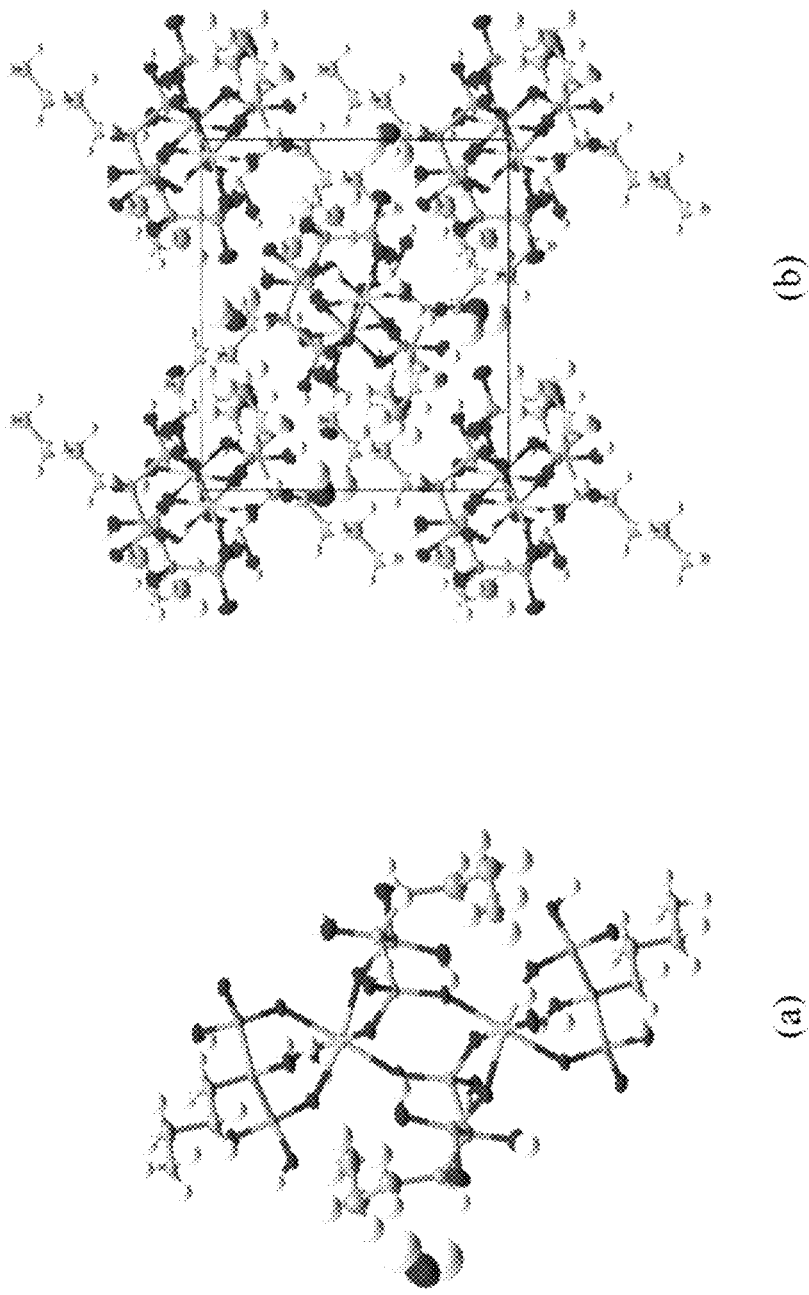
FIG. 13A shows the molecular structure of (a) the asymmetric unit and (b) crystalline packing of ALEN-Mg complex along a-axis.
Figure 13B:
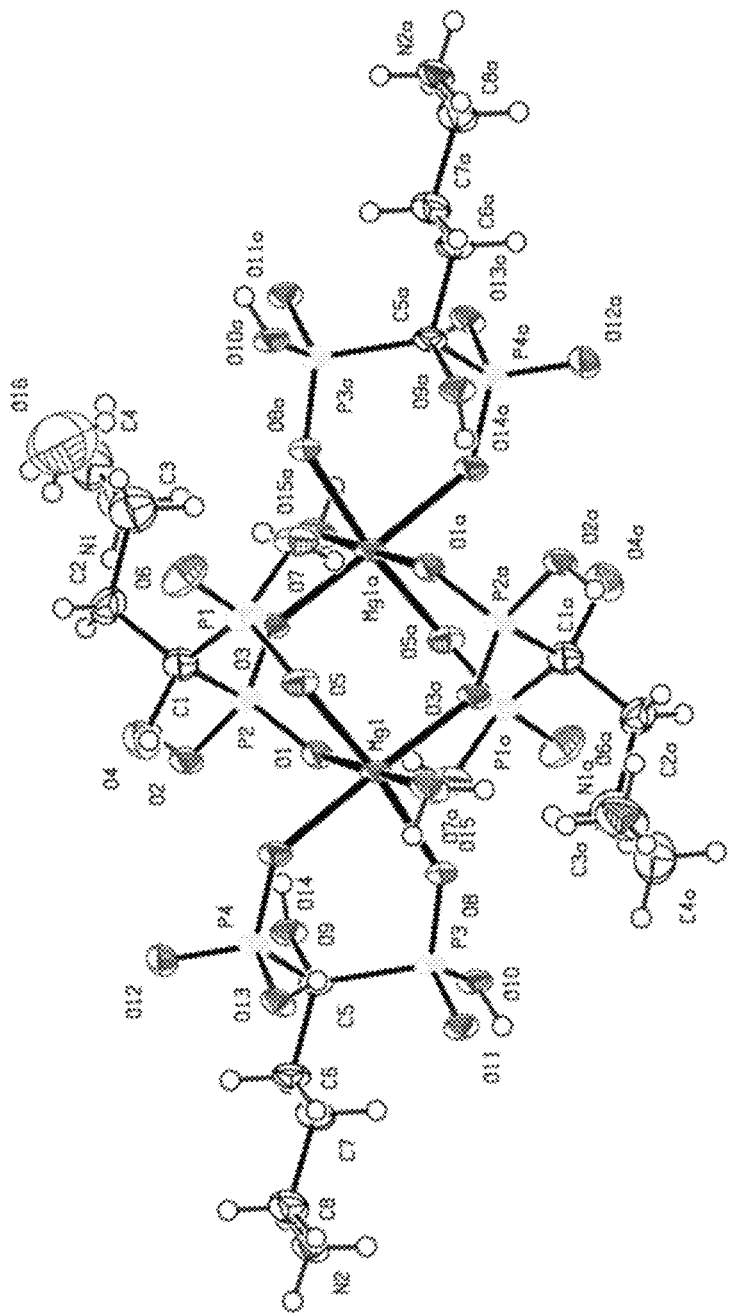
FIG. 13B shows a ball-stick representation (atoms labeled) showing the connectivity between Mg and ALEN ligands to form the ALEN-Mg coordination complex.
Figure 14A:
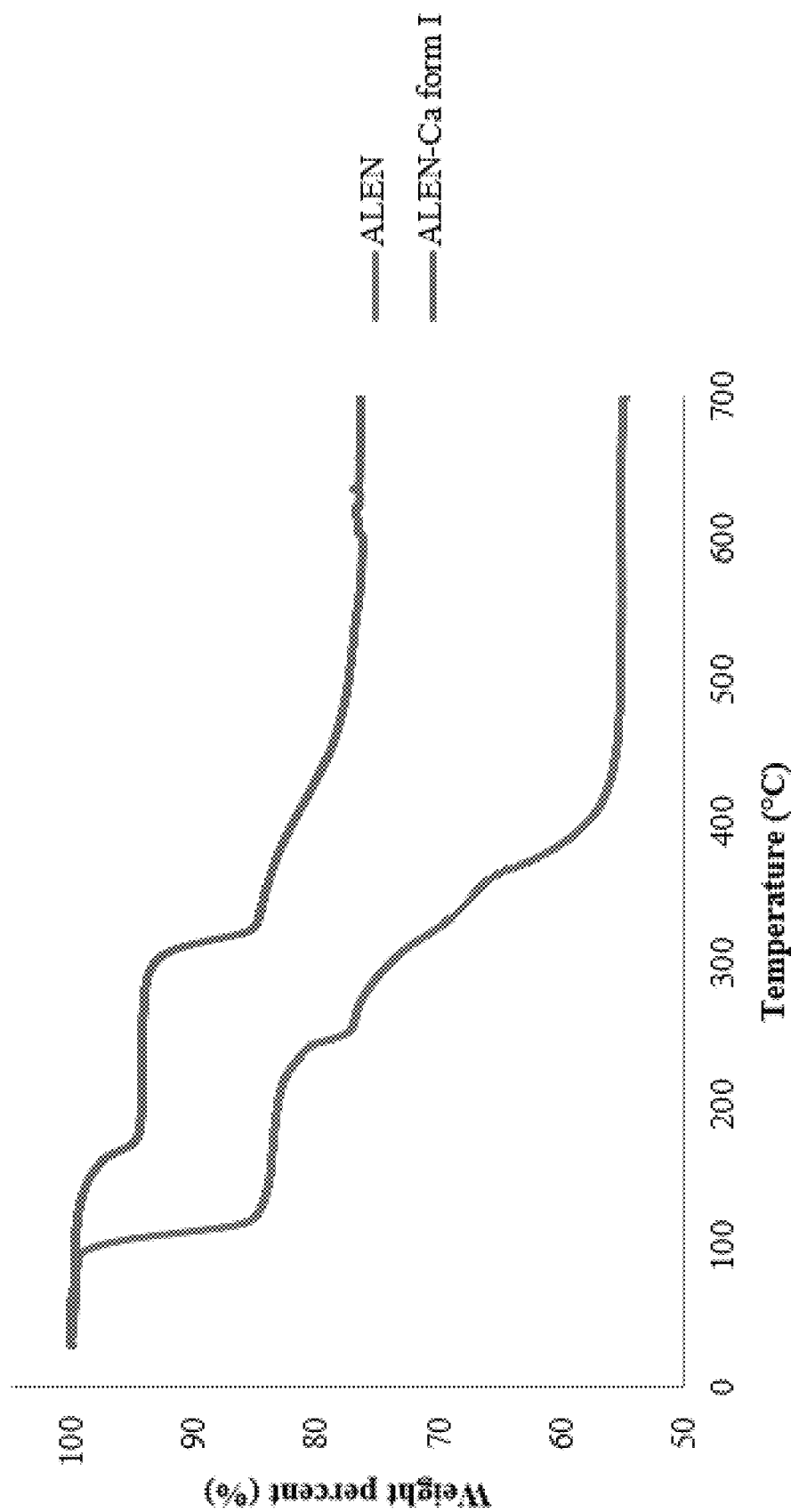
FIG. 14A shows a TGA analysis of ALEN-Ca form I complex shows a low temperature (140-190° C.) weight lost (5.29% w/w), which was attributed to the decomposition of the ligand, subsequently at higher temperature (290-700° C.) weight lost (17.77% w/w) occurred, which was attributed to the degradation of calcium.
Figure 14B:
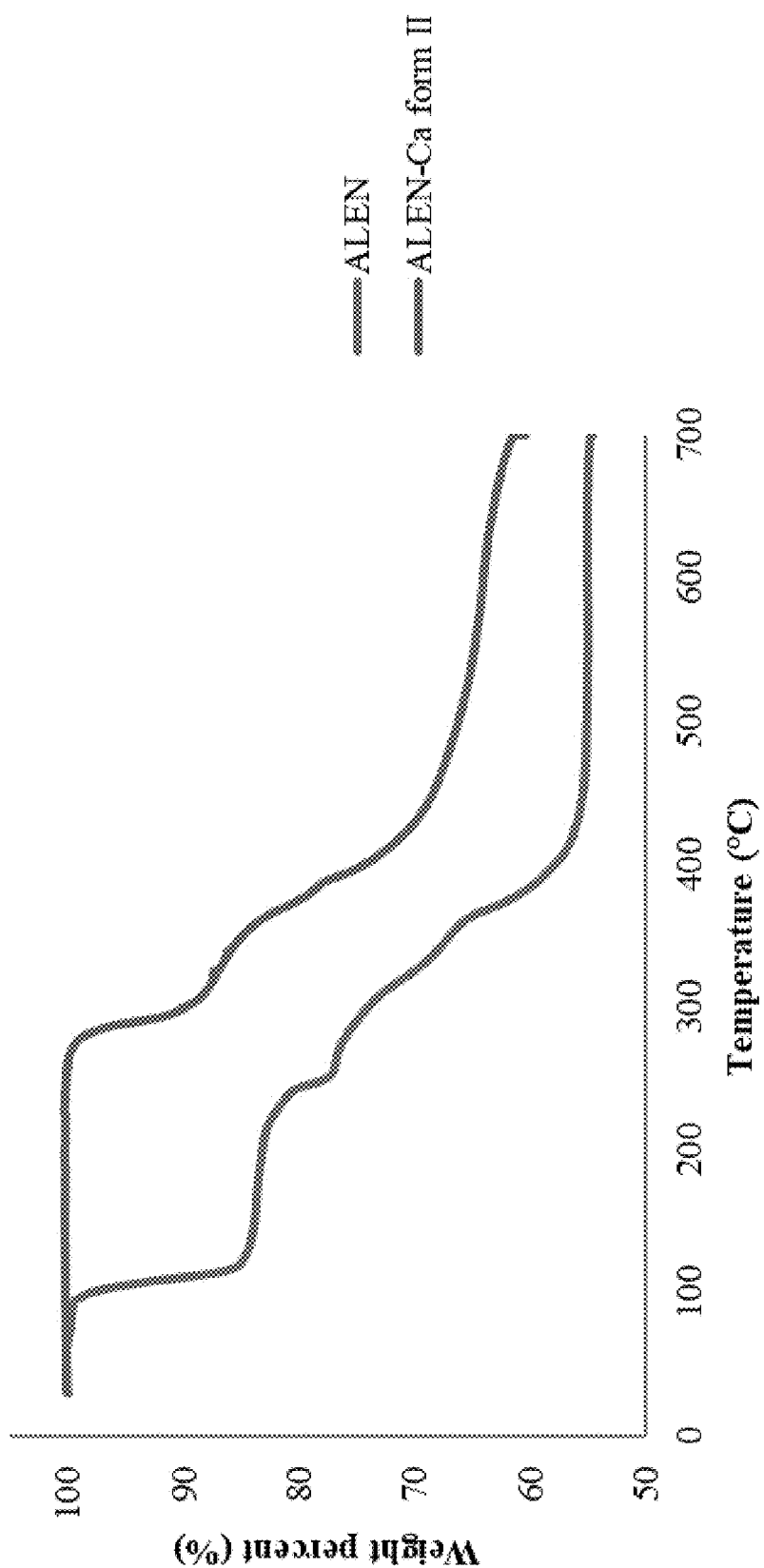
FIG. 14B shows a TGA analysis of ALEN-Ca form II complex shows a low temperature (260-300° C.) weight lost (12.14% w/w), which was attributed to the decomposition of the ligand, subsequently at higher temperature (300-700° C.) weight lost (26.39% w/w) occurred, which was attributed to the degradation of calcium.
Figure 14C:
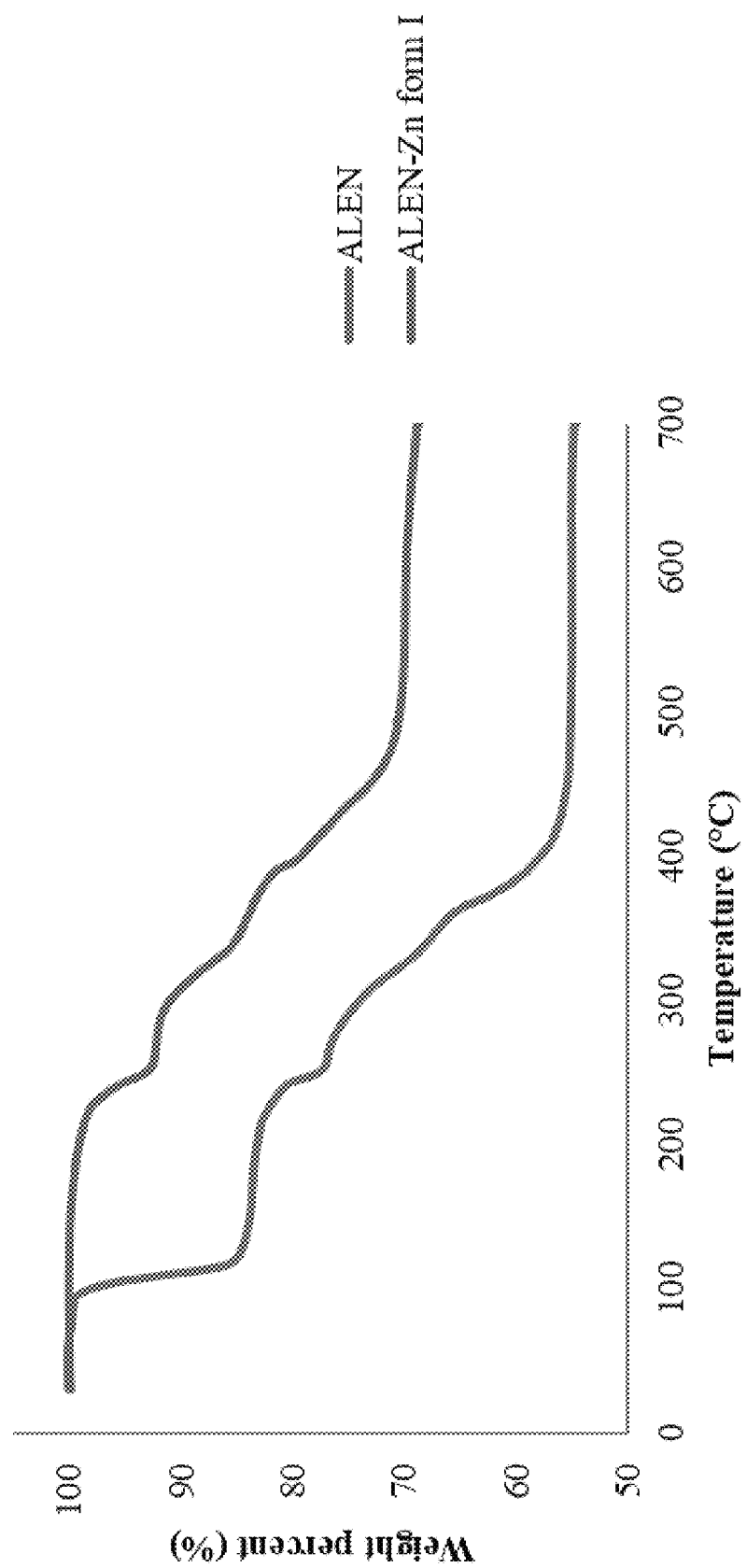
FIG. 14C shows a TGA analysis for the ALEN-Zn form I complex, a low temperature (200-250° C.) weight lost (5.09% w/w), was observed, which is attributed to the decomposition of the BP ligand, subsequently, at higher temperature (300-700° C.), the degradation of zinc occurs as accounted by a weight loss of 16.34% w/w.
Figure 14D:
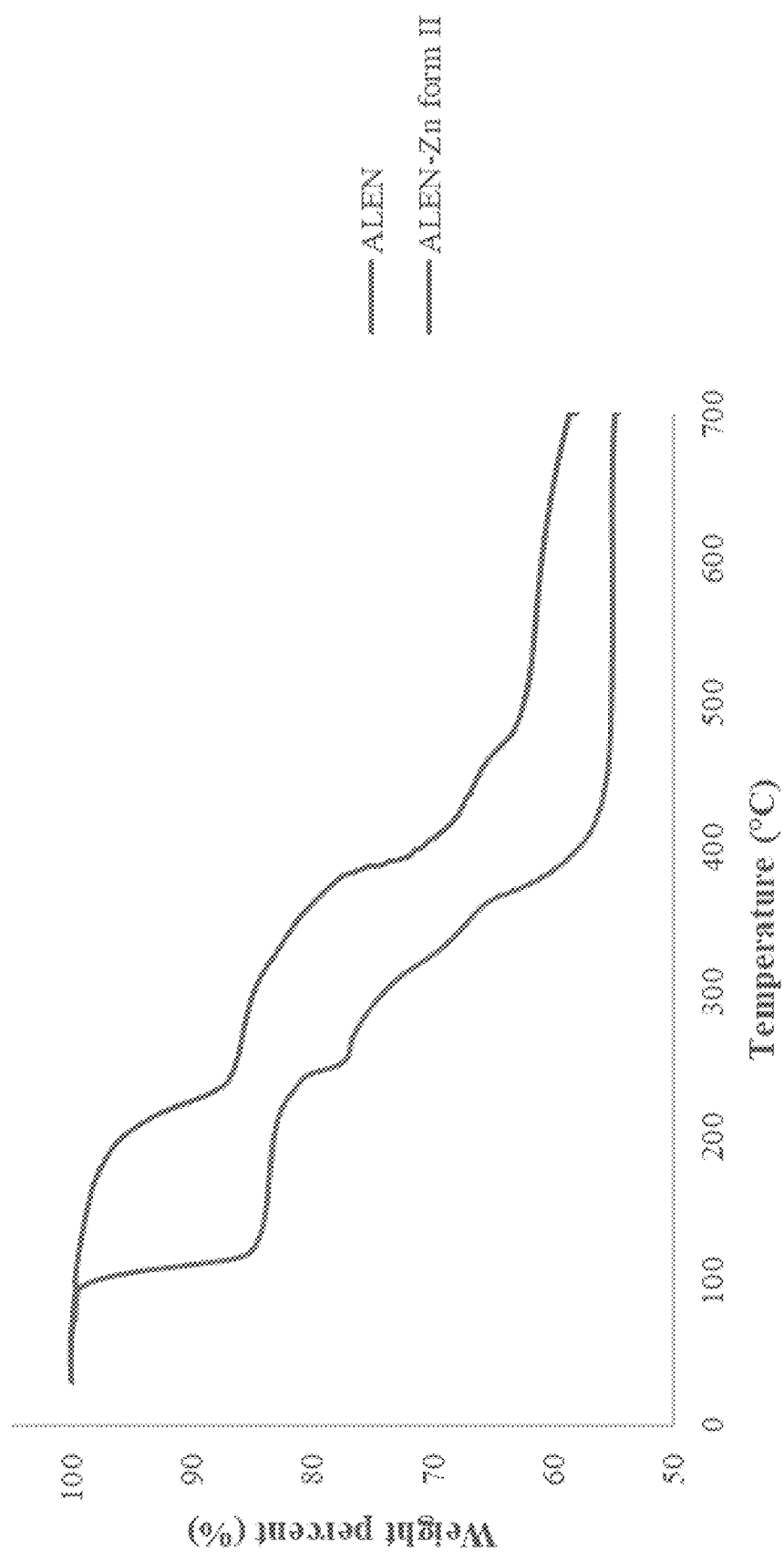
FIG. 14D shows a TGA analysis for the ALEN-Zn form II complex, a low temperature (150-300° C.) weight lost (12.30% w/w), was observed, which is attributed to the decomposition of the BP ligand, subsequently, at higher temperature (300-700° C.), the degradation of zinc occurs as accounted by a weight loss of 25.56% w/w.
Figure 14E:
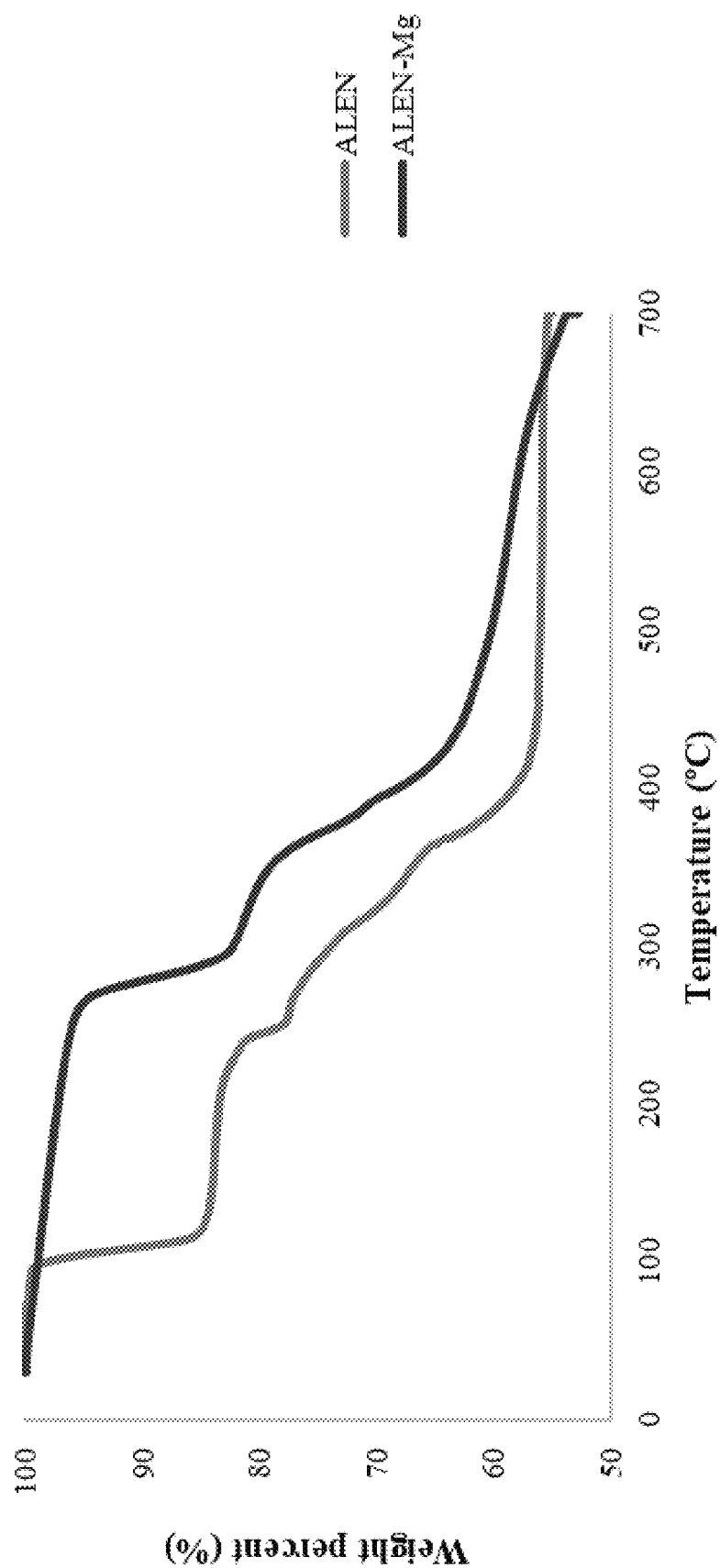
FIG. 14E shows a TGA analysis of ALEN-Mg complex shows a low temperature (260-300° C.) weight lost (12.51% wt.), which was attributed to the decomposition of the ligand, subsequently at higher temperature (360-700° C.) weight lost (23.48% wt.) occurred, which was attributed to the degradation of magnesium.

ALEN-Mg:

The compound Mg$_2$[C$_{16}$H$_{12}$N$_2$O$_7$P$_2$(H$_2$O)$_2$]·2H$_2$O is isostructural to ALEN-Zn form II described above. ALEN-Mg is defined by the P2$_1$/c space group and has one molecule in the asymmetric unit. The magnesium atom has a strongly distorted octahedral environment with the O—Zn—O bond angles ranging from 87.33° to 99.26°. The Mg—O bond distances are between 2.007 and 2.162 Å. The ligand, ALEN, bridges the Mg(II) ions into an infinite single chain through four phosphonate oxygens and the hydroxyl oxygen in a similar fashion as that displayed in the structure of ALEN-Zn form II. Inter-chain hydrogen bonds help form a 3D network structure with channels generated along the a-axis. The protonated amine tails and the lattice water reside in the channels and are held in position by intricate systems of hydrogen bonds. FIGS. 13A and 13B show the molecular structure and a ball-stick representation of the structure, respectively.

Thermal Analysis of the ALEN-Based Metal Complexes

Thermal stability under nitrogen of the isolated pBioCCs was investigated through thermal gravimetric analysis (TGA) and the resulting thermographs for these materials are displayed in FIGS. 14A-14E (ALEN-based metal complexes overlayed on top of ALEN as received on the graphs). It was expected that the thermograph of each pBioCCs consists of at least two mayor decomposition profiles one at lower temperature representing the loss of coordinated or lattice water molecules, and another at higher temperature which accounts for the thermal combustion of the organic moiety, the BP ligand, in this case ALEN. A third decomposition event might be observed above 350° C., due to the thermal degradation of the metal/metal oxide.

For the thermal decomposition of ALEN as received, a low temperature (100° C.) weight loss (14.67%) was observed, which correspond to the evaporation of water due to the hydration of the ligand molecules (trihydrate). Subsequently, at higher temperature (225-400° C.) weight loss (27.33%) was observed, which correspond to the degradation of the ligand molecules. In the TGA of the ALEN-Ca form I (FIG. 14A), a low temperature (140-190° C.) weight lost (5.29%), was observed, which was attributed to the decomposition of the BP ligand. Subsequently, at higher temperature (290-700° C.), the degradation of the metal occurs which accounts for a weight loss of about 17.77%. The pBioCCs composed of ALEN and Ca that formed in the presence of an auxiliary ligand, HEDP, ALEN-Ca form II (FIG. 14B), displays considerable weight lost (12.14%) at about 260-300° C. This weight loss was attributed to the decomposition of ALEN and HEDP. A second thermal event was observed at higher temperatures (300-700° C.), which as accounts for the degradation of metal (26.39%). The TGA of the ALEN-Zn form I complex (FIG. 14C) show a low temperature (200-250° C.) weight lost (5.09%), which was attributed to the decomposition of the ALEN. Subsequently, at higher temperature (300-700° C.), the degradation of the complex occurs (16.34%). The pBioCCs composed of ALEN and Zn that formed in the presence of an auxiliary ligand, HEDP, ALEN-Zn form II (FIG. 14D), displays considerable weight lost (12.30%) at about a low temperature (150-300° C.). This weight loss was attributed to the decomposition of both ALEN and HEDP. A second thermal event was observed at higher temperatures (300-700° C.), which as accounts for the degradation of metal (25.56%). The TGA of the ALEN-Mg complex (FIG. 14E) show a low temperature (260-300° C.) weight lost (12.51%), which was attributed to the decomposition of the ALEN. Subsequently, at higher temperature (360-700° C.), the degradation of the metal occurs (23.48%).

According to the above-mentioned thermal analysis, the five bisphosphonate-based metal complexes investigated (ALEN-Ca forms I and II, ALEN-Zn forms I and II, and ALEN-Mg) present high thermal stability under $N_2$. On the basis of the thermogravimetric study, all isolated alendronate-based metal complexes are stable to ~50° C. after which some of them quickly loose lattice water molecules up to 150° C., followed by the loss of coordinated water molecules, and the BP ligand and complex degradation at temperatures near 250° C. Moreover, the comparison of the thermograms for ALEN and the ALEN-based metal complexes demonstrates the formation of materials, which in general show higher thermal stability than the BP alone.

Dissolution Rate Measurements for Alendronate-Based Metal Complexes

ALEN is a polyvalent strong acid with a high solubility in water, commercially; alendronate monosodium salt (Fosamax®) is available in form of tablets. Once orally administered, the dissolution starts during deglutition. This rapid dissolution affects the intake of the drug during the absorption process, lowering the absorbed dose taken up by the skeleton (to only about 20-50% of the administered dosage) and causing adverse side effects to patients, such as esophagitis. In order to assess the dissolution properties of the synthesized complexes, dissolution profiles were obtained in two simulated body fluids, PBS and FaSSGF. ALEN lacks a detectable chromophore, therefore, the formation of an ALEN-Cu complex was employed as a suitable method of quantification for the released content from the pBioCCs by a conventional UV-Vis spectrophotometer, this method has previously been employed for Risedronic acid. Compared to the synthesized complexes employing calcium, magnesium and zinc ($Ca^{2+}$, $Mg^{2+}$ and $Zn^{2+}$), aside of having UV activity, the ALEN-Cu complex and other bisphosphonates-Cu salts tend to have high solubility at lower pH. As part of the invention, quantification of the drug release in acidic (FaSSGF) and neutral (PBS) media was conducted, permitting the optimum conditions for promoting the formation of the UV active ALEN-Cu complex and avoiding precipitation.

The administered dosage of Alendronate Sodium in tablets to patients is 70 mg, which correspond to the initial weight for the pBioCCs and the commercial ALEN for the dissolution testing. The dissolution procedure was conducted on two different buffers for which each one simulates different body conditions in terms of pH. Varying pH conditions lead to understand the structural stability of the metal complexes as well their dissolution behavior regarding different absorption pathways in the gastrointestinal tract.

Figure 15A:
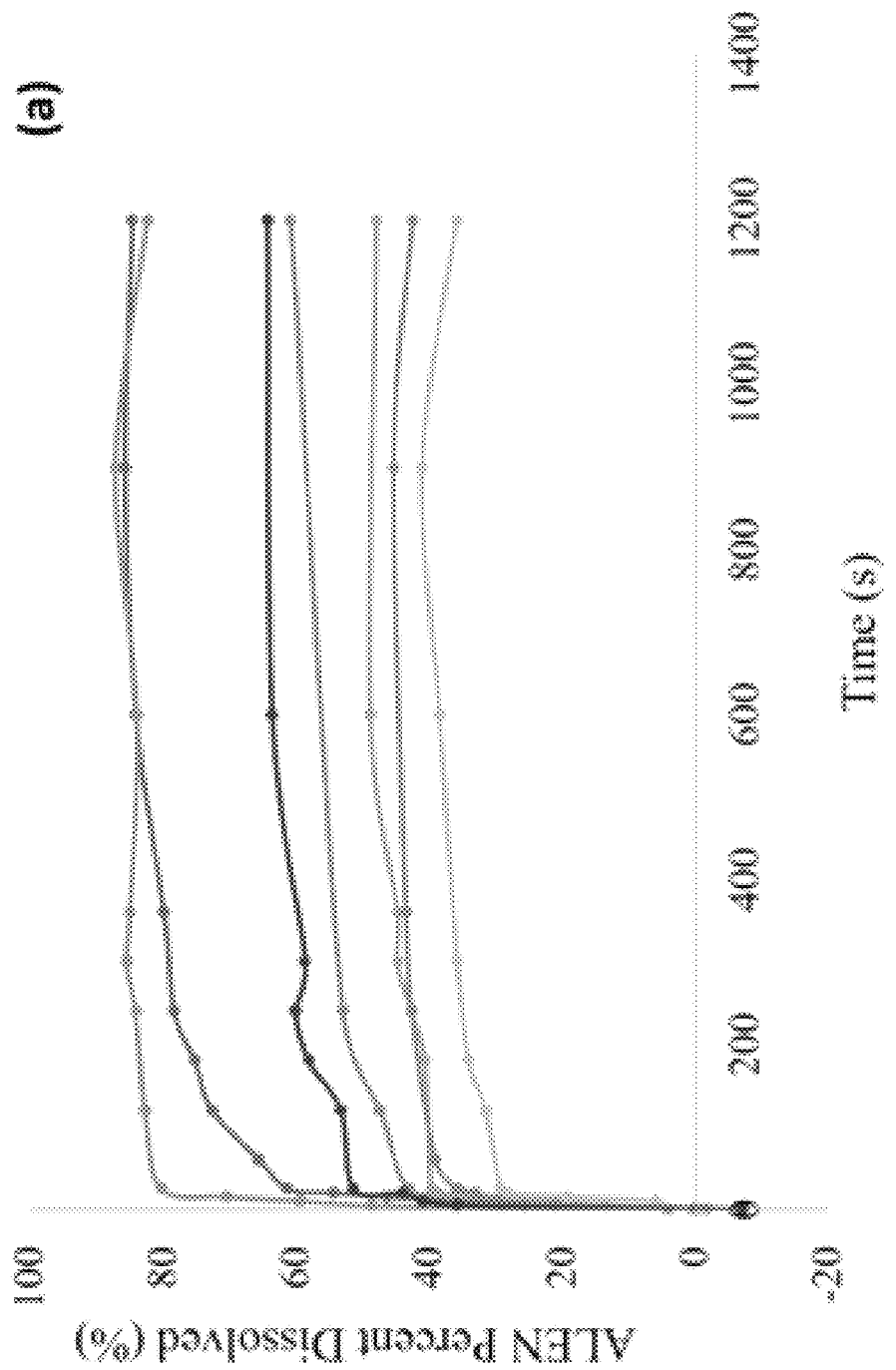
FIG. 15A shows a complete dissolution profile for ALEN reagent, Alendronate Sodium tablets, ALEN-Ca form I, ALEN-Ca form II, ALEN-Zn form I, ALEN-Zn form II and ALEN-Mg in FaSSGF.

For the simulated drug release in fasted sate gastric conditions, dissolution testing was conducted in FaSSGF (pH=1.60). The early-stage dissolution in the acidic media revealed a 97% of the drug dissolved for the commercial ALEN after 10 sec, presenting the most rapid release from all the compounds analyzed in this media. The alendronate sodium tablets showed a maximum release of the drug (100%) after 25 sec. The percent dissolved from the pBioCCs ranged between 12-65% after 25 sec, in which this early-stage dissolution profile was completed as will be explained in detail below. The complete dissolution profile in FaSSGF for all pBioCCs revealed a similar behavior as in PBS for ALEN and the alendronate sodium tablets, but an inverse relationship among the pBioCCs (FIG. 15A). This complete dissolution profile showed that ALEN as the reagent reaches the maximum release or dissolution of the drug (100%) in a shorter amount of time (10 sec) compared to the other compounds and kept stable for 20 min. The alendronate tablets achieved a 100% release in 25 sec. These results support the fact of the poor absorption of the BP (up to 10%) in the intestines reported in literature. It is poorly absorbed in this area because most of the ALEN content from the formulation is released from the tablet during deglutition and in the stomach. In the case of the pBioCCs, the metal complexes with calcium coordinates presented higher solubility and dissolution rate. The maximum release of the ALEN content from their structure was 100% for each one after 15 min. ALEN-Mg presented a moderate dissolution rate and solubility in this media, reaching an average of 45% as its maximum release of ALEN after 10 min. The moderate to lower dissolution rates correspond to the pBioCCs containing zinc, which reached a maximum release of 66% and 35% for ALEN-Zn forms I and II, respectively.

Figure 15B:
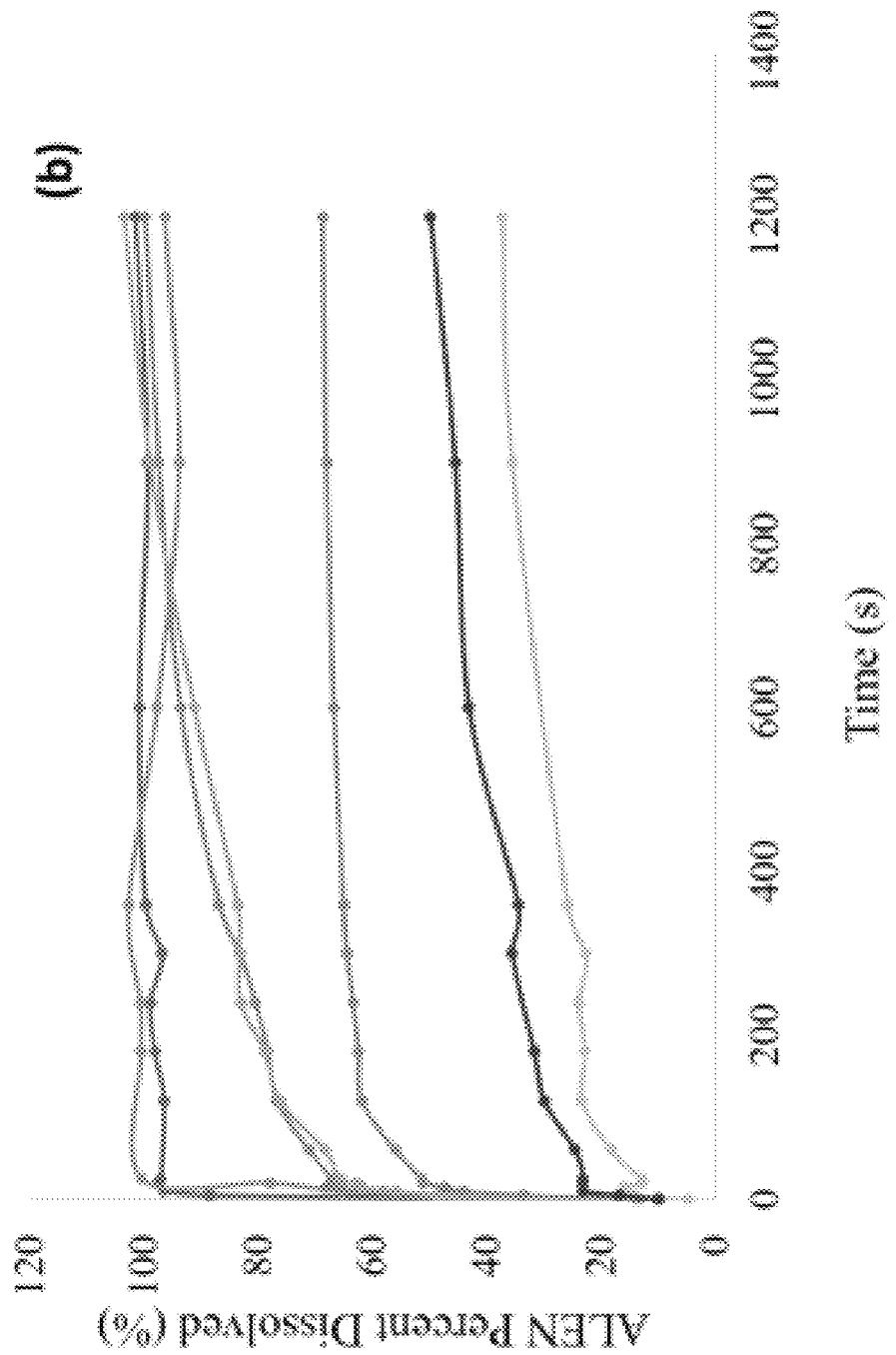
FIG. 15B shows a complete dissolution profile for ALEN reagent, Alendronate Sodium tablets, ALEN-Ca form I, ALEN-Ca form II, ALEN-Zn form I, ALEN-Zn form II and ALEN-Mg in PBS.
Figure 16:
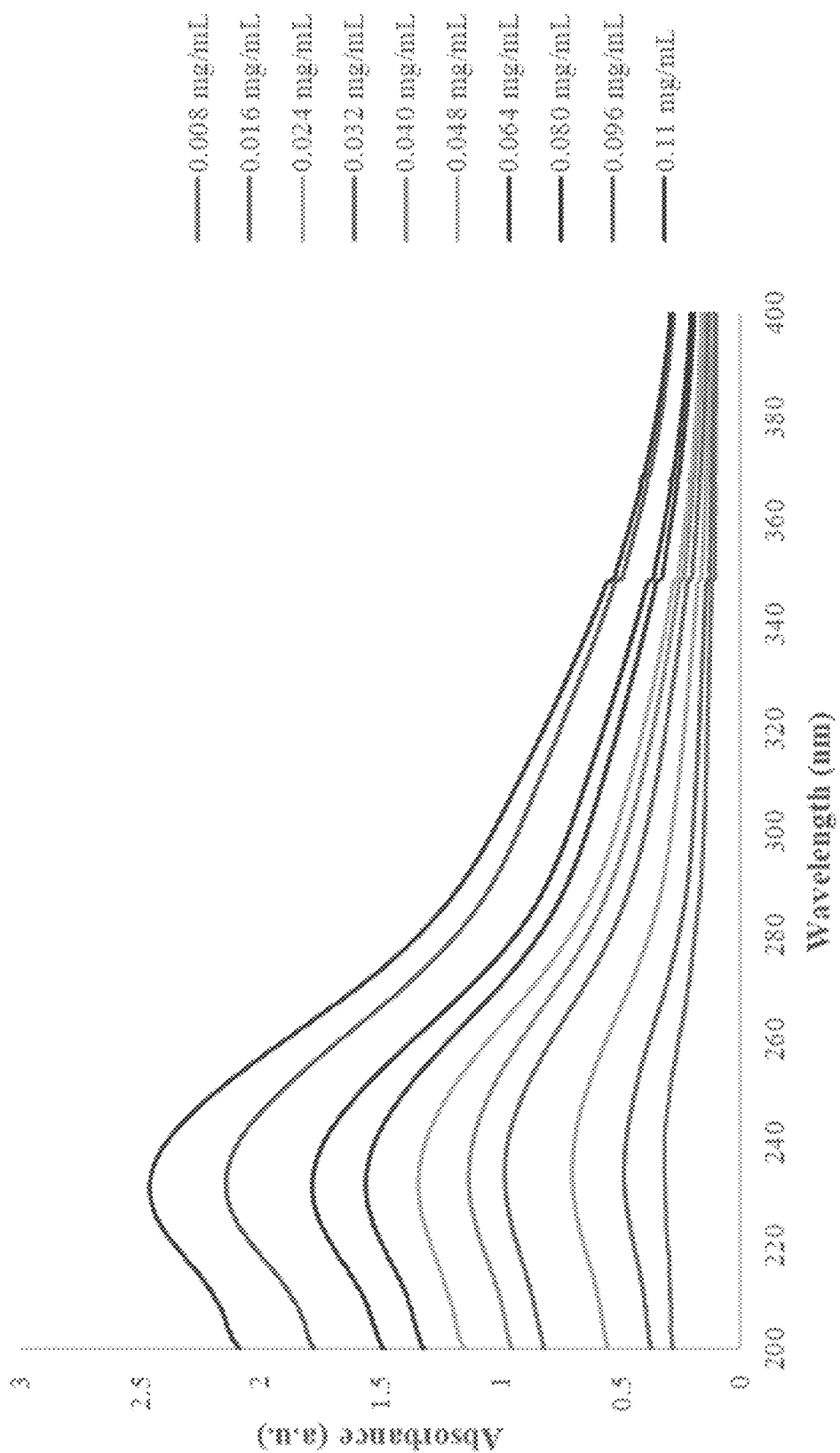
FIG. 16 shows absorbance spectra of ALEN-Cu complex presenting a $\Delta_{max}$ at 231 nm in PBS in the concentration range employed to provide the calibration curve.
Figure 17:
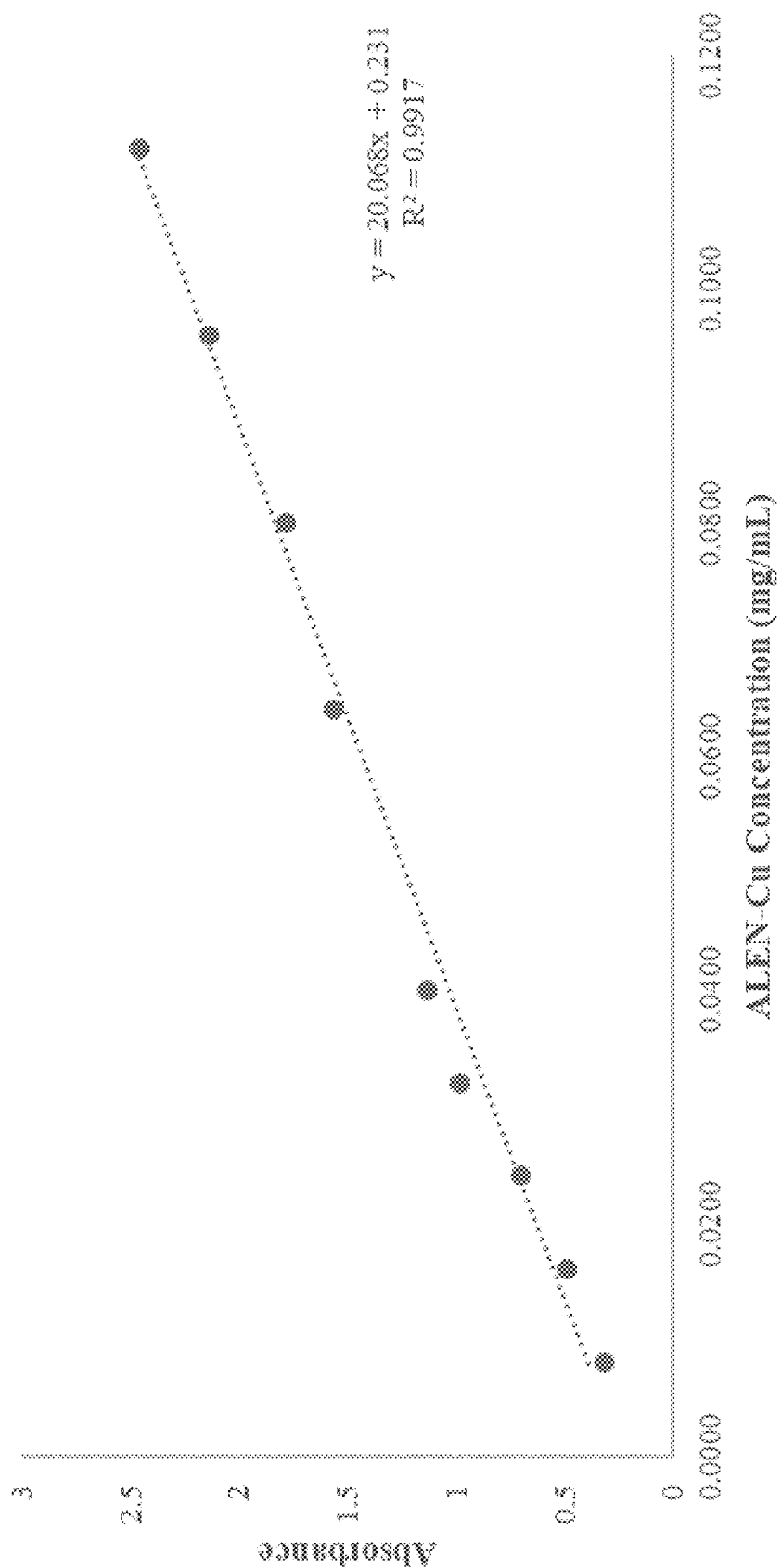
FIG. 17 shows a calibration curve of ALEN-Cu complex for alendronate (ALEN) quantification from pBioCPs in PBS.
Figure 18:
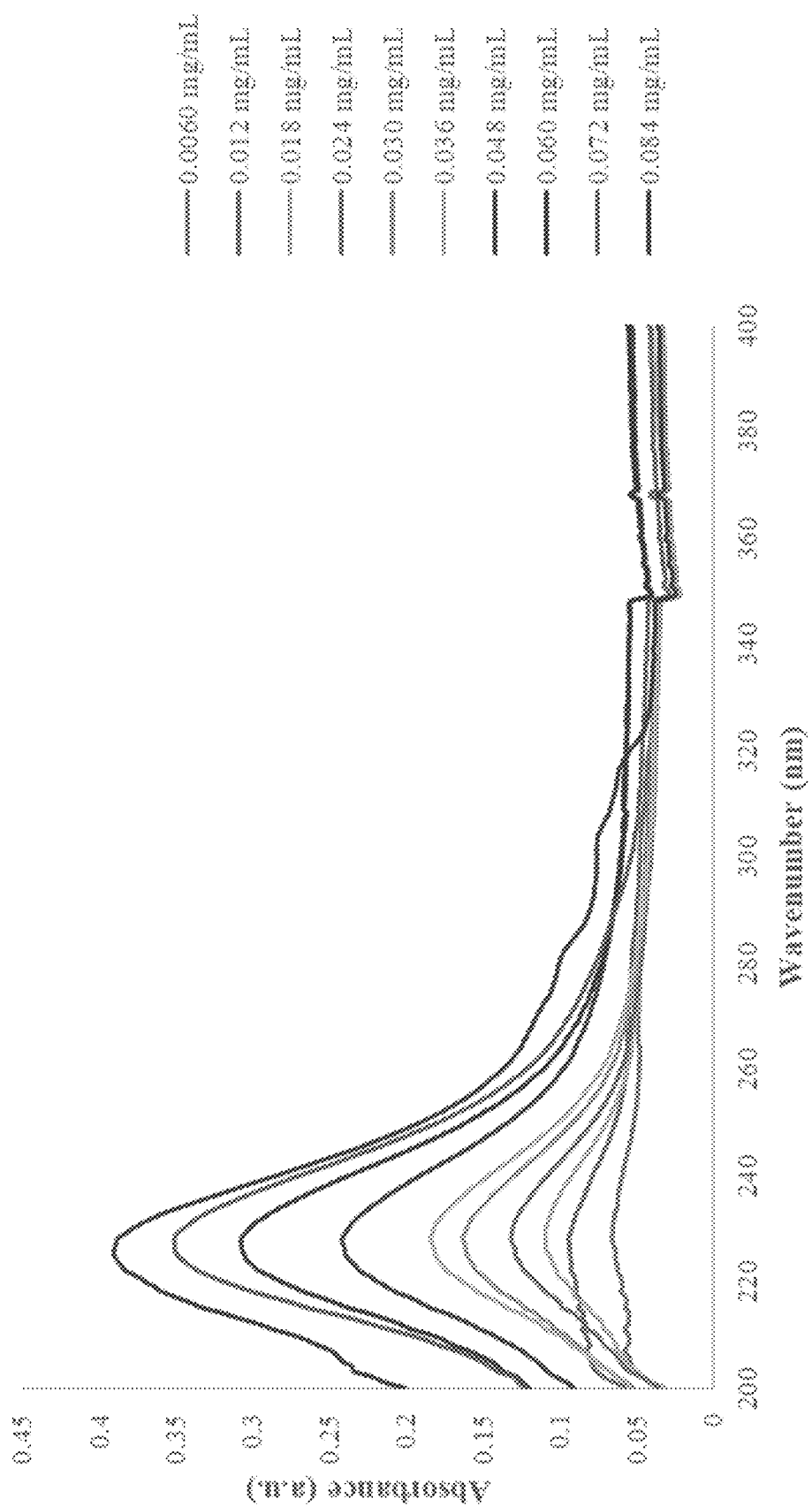
FIG. 18 shows absorbance spectra of ALEN-Cu complex presenting a $\Delta_{max}$ at 225 nm in FaSSGF.
Figure 19:
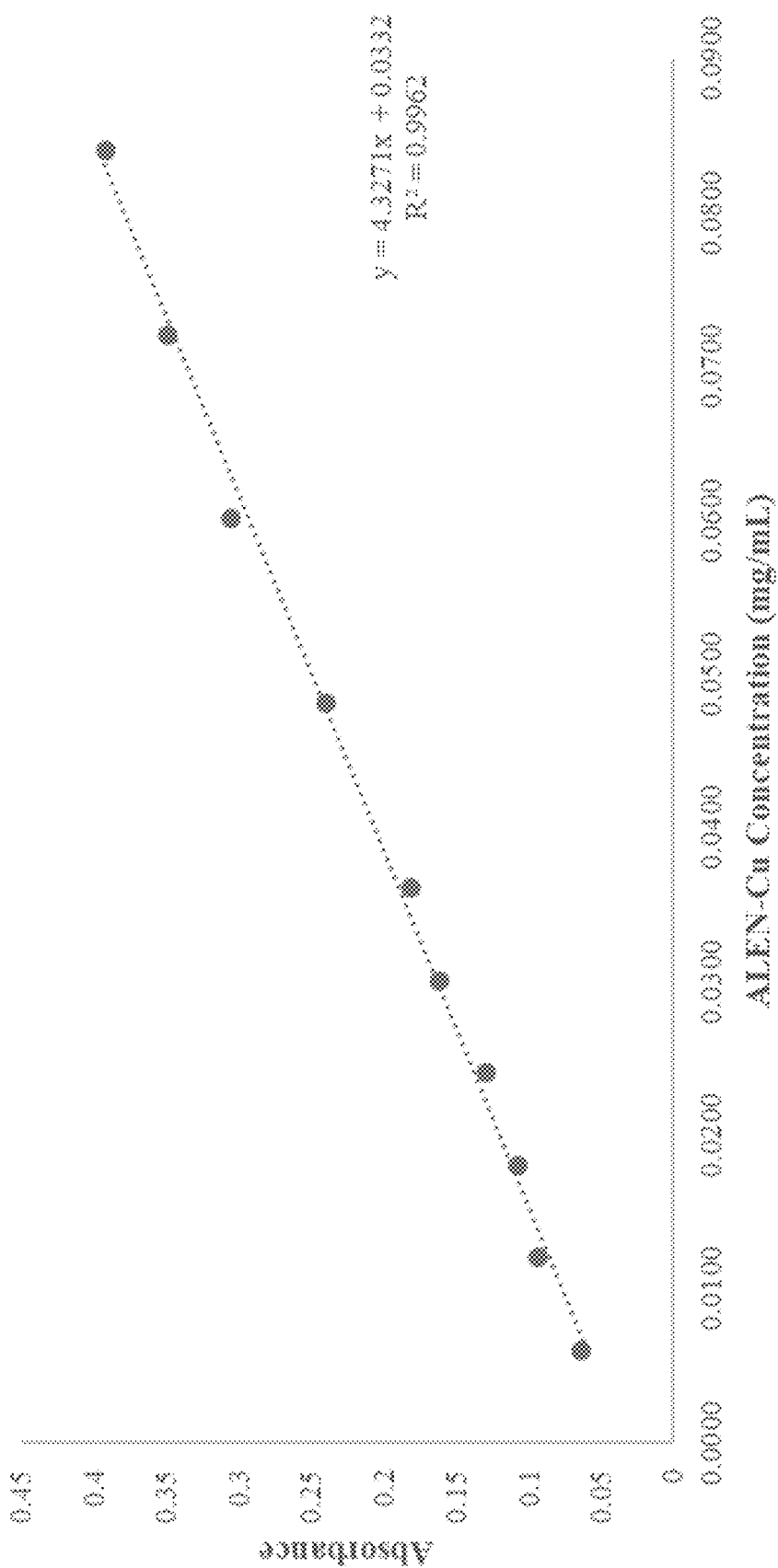
FIG. 19 shows a calibration curve of ALEN-Cu complex for alendronate (ALEN) quantification from pBioCPs in FaSSGF.
Figure 20:
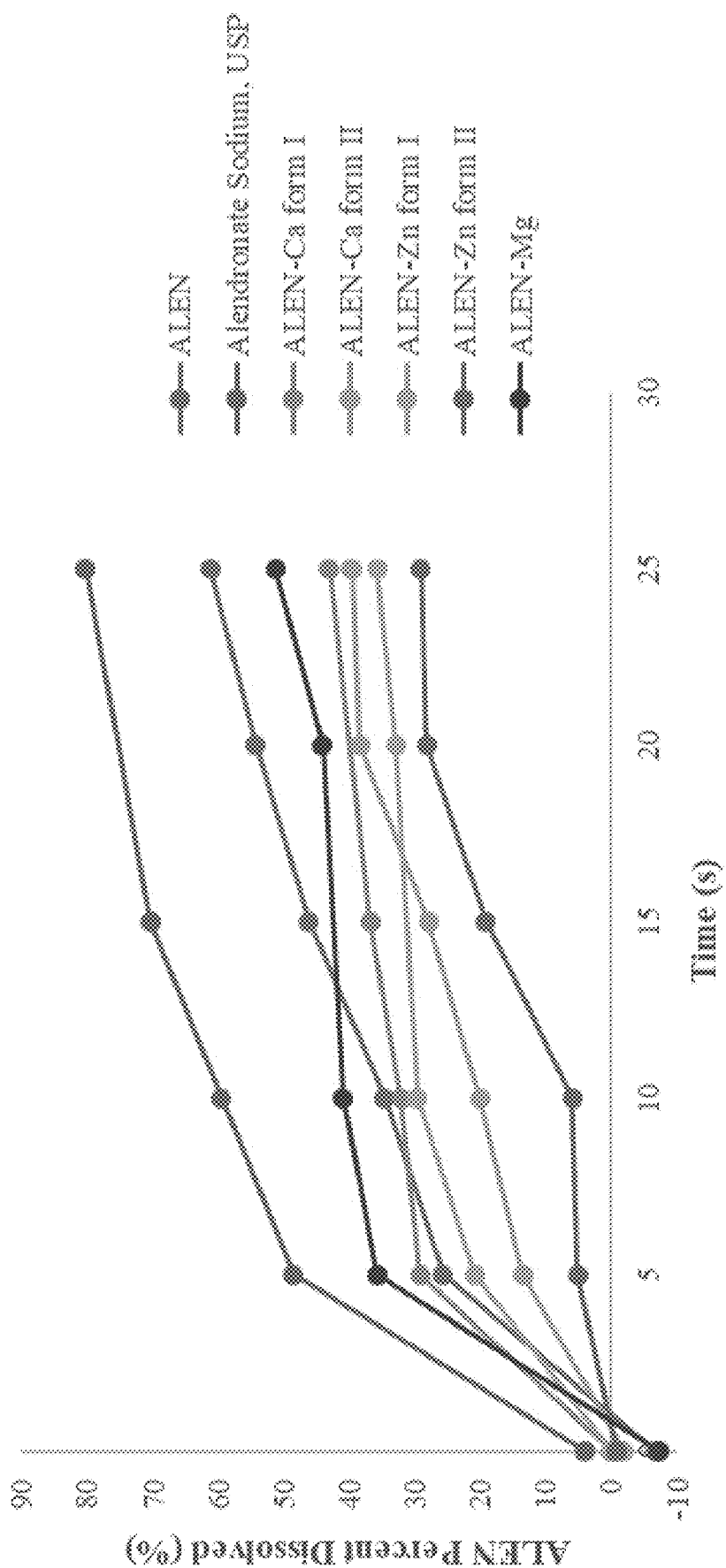
FIG. 20 shows an early stage dissolution profile (deglutition) in PBS for ALEN reagent, Alendronate Sodium tablets, ALEN-Ca form I, ALEN-Ca form II, ALEN-Zn form I, ALEN-Zn form II and ALEN-Mg as quantified by the ALEN-Cu complexation method.
Figure 21:
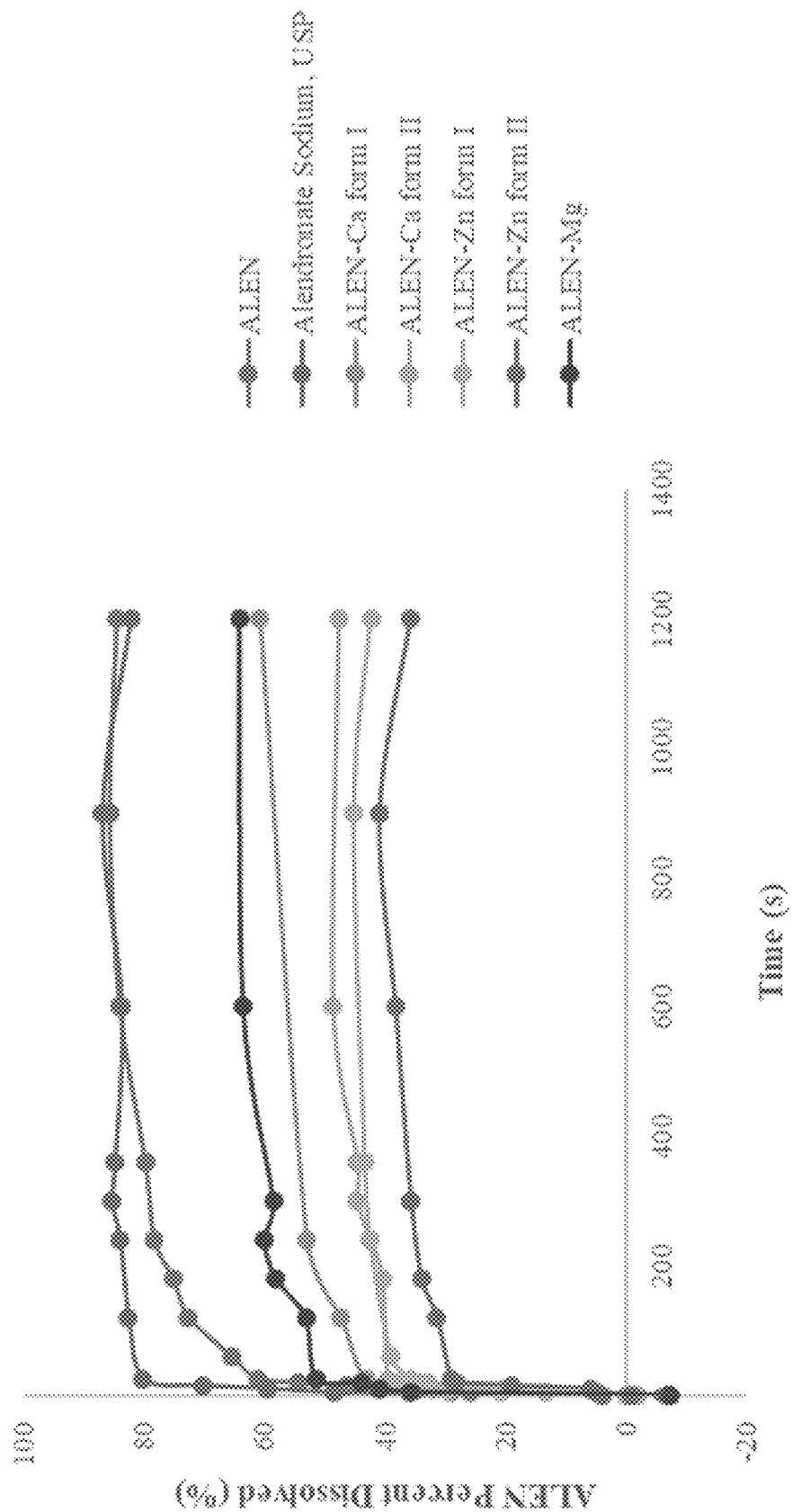
FIG. 21 shows a complete dissolution profile in PBS for ALEN reagent, Alendronate Sodium tablets, ALEN-Ca form I, ALEN-Ca form II, ALEN-Zn form I, ALEN-Zn form II and ALEN-Mg as quantified by the ALEN-Cu complexation method.
Figure 22:
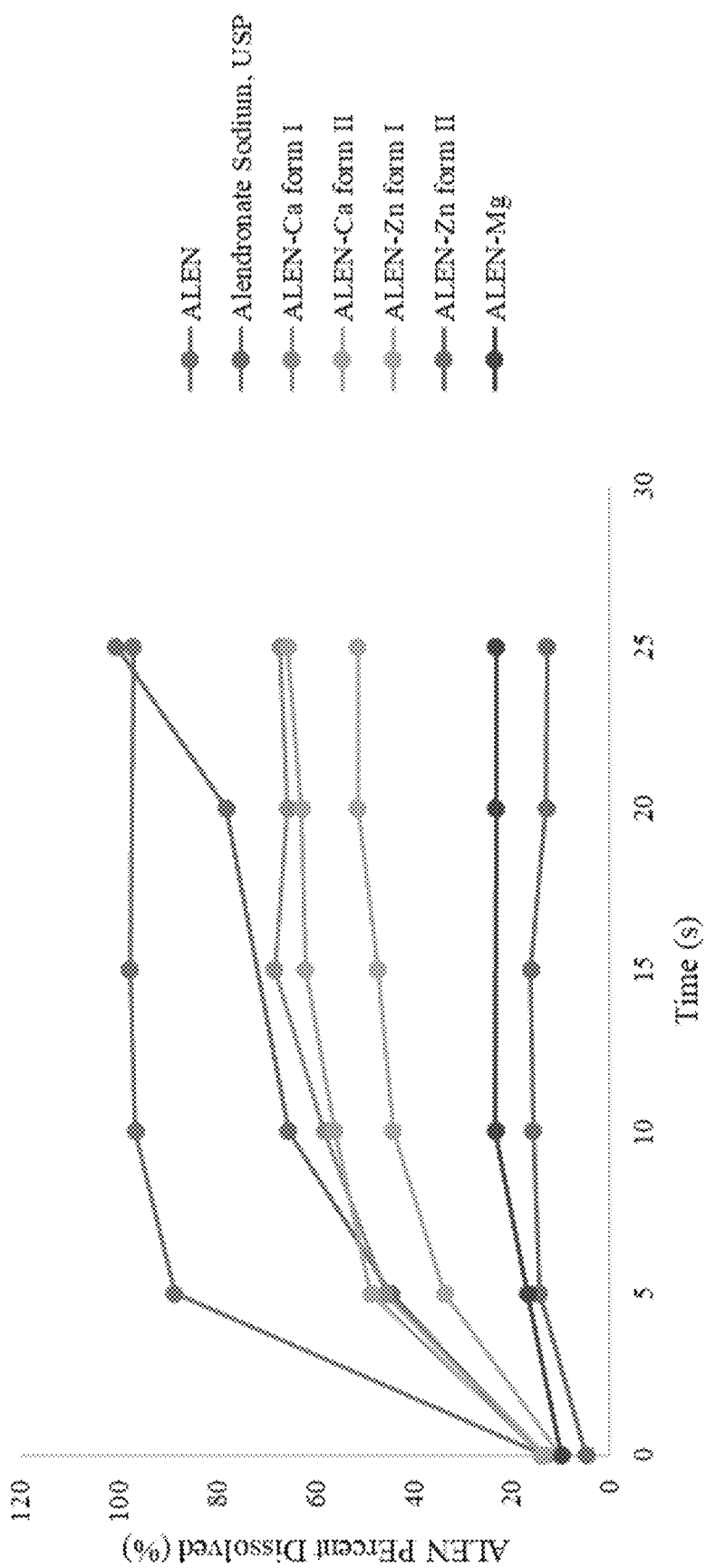
FIG. 22 shows an early stage dissolution profile in FaSSGF for ALEN reagent, Alendronate Sodium tablets, ALEN-Ca form I, ALEN-Ca form II, ALEN-Zn form I, ALEN-Zn form II and ALEN-Mg as quantified by the ALEN-Cu complexation method.
Figure 23:
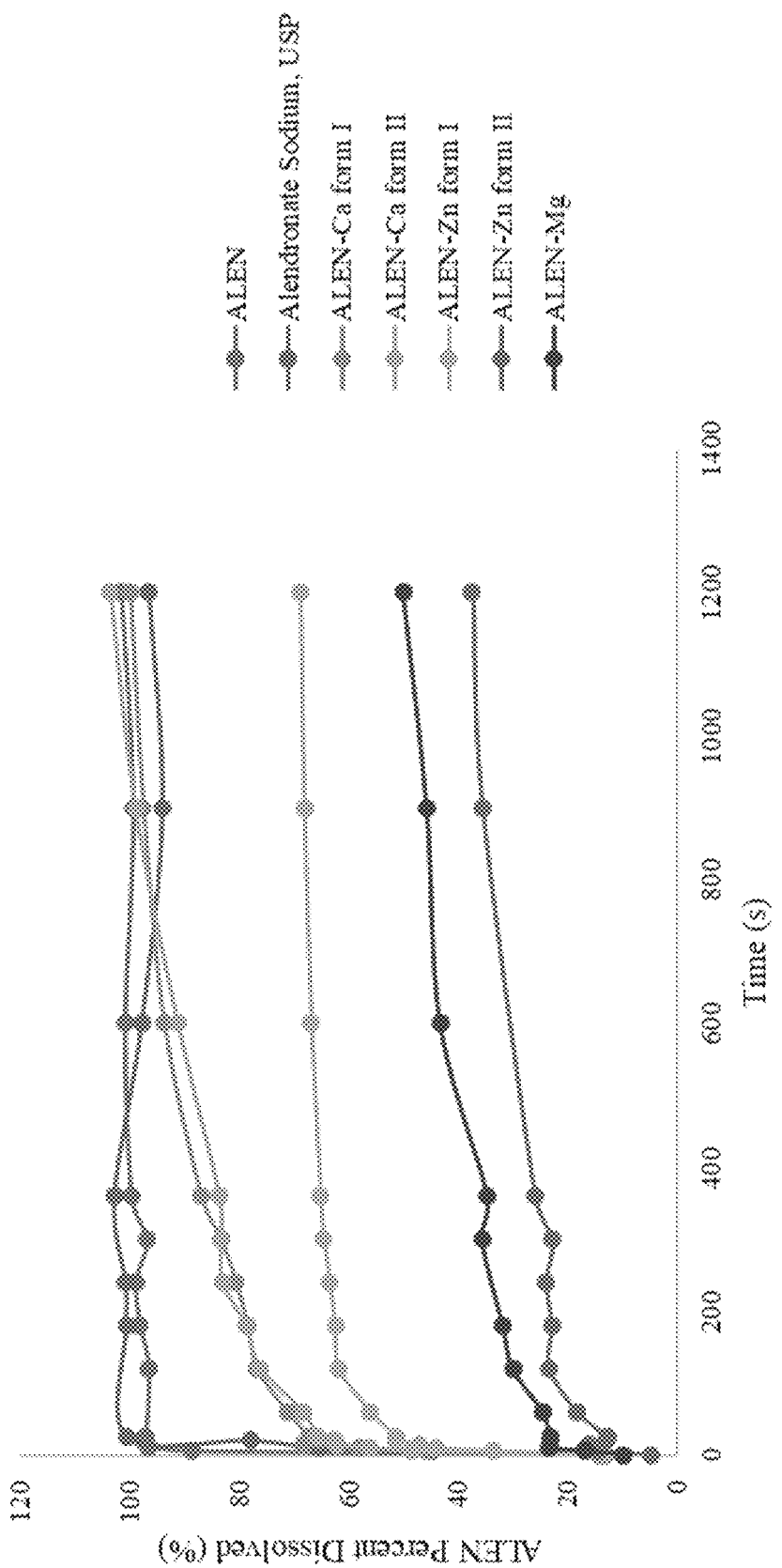
FIG. 23 shows a complete dissolution profile in FaSSGF for ALEN reagent, Alendronate Sodium tablets, ALEN-Ca form I, ALEN-Ca form II, ALEN-Zn form I, ALEN-Zn form II and ALEN-Mg as quantified by the ALEN-Cu complexation method.

In PBS media (pH=7.40), early-stage dissolution results revealed a 61% of ALEN dissolved from the reagent and an 80% of ALEN released from the commercial alendronate sodium, USP, after 25 sec. This corroborates the rapid release and high solubility of the bisphosphonate as reported previously in literature. In terms of the early-stage dissolution for the pBioCCs, the ALEN content released from the complexes varied between 29-51% after the same amount of time. After comparing the complete dissolution profile for each compound analyzed (FIG. 15B), results demonstrate that alendronate sodium tablets have the higher dissolution rate, reaching the maximum release of the ALEN content (80%) in 25 sec. Dissolution for commercial ALEN resulted in a slower release but reach the similar amount of dissolved drug as the tablets (~80%) in 10 min. The pBioCCs showed a lower solubility and dissolution rate compared to the tablets and the reagent in this media (PBS). The metal complexes reached a maximum release after 6-10 min and kept stable through 20 min. ALEN-Mg showed the higher dissolution rate between the metal complexes, releasing a maximum of 63% of the ALEN content from the structure. The crystal phases containing calcium, presented moderate dissolution rates and release of the drug, showing a 52% and 48% of ALEN dissolved for ALEN Ca forms I and II, respectively. Metal complexes with Zinc, revealed lower dissolution rates and drug release, which correspond to a percent of ALEN dissolved of 43% and 35% for ALEN-Zn forms I and II, respectively.

Dissolution Profiles for ALEN Metal Complexes

Dissolution profiles were performed via copper (II) complexation with alendronate content from the synthesized pBioCPs and quantified by measuring absorbance through UV-Vis spectroscopy. Two standard stock solution of ALEN were prepared by dissolving 100 mg of the drug in a 100-mL volumetric flask with PBS and the other one with FaSSGF. More dilute solutions were obtained by appropriate dilution from these stock solutions. Accurately measured aliquots of the ALEN stock solutions were transferred into a series of 25-mL volumetric flasks to achieve a concentration range of 0.05-0.7 mg/mL. Each solution was completed to the 25-mL mark with PBS and FaSSGF respectively. A calibration curve of ALEN-Cu complex with a concentration range of 0.008-0.11 mg/mL in PBS and 0.006-0.084 mg/mL in FaSSGF was used for indirect alendronate quantification. To generate the ALEN-Cu complex in PBS, 4 mL of the diluted ALEN solutions were transferred into a series of 25-mL volumetric flasks to achieve an ALEN-Cu concentration range of 0.008-0.11 mg/mL. To each flask, 20 mL of 2.5 mM $CuSO_4$ solution was added, homogenized and completed to volume with nanopure water. The absorbance of the formed ALEN-Cu complex was measured at 231 nm against a reagent blank prepared by the addition of 4 mL PBS buffer and 20 mL of the $CuSO_4$ solution in a 25-mL volumetric flask and completed to volume with nanopore water. To generate the ALEN-Cu complex in FaSSGF, 3 mL of the diluted ALEN solutions were transferred into a series of 25-mL volumetric flasks to achieve an ALEN-Cu concentration range of 0.006-0.084 mg/mL. To each flask, 15 mL of 2.5 mM $CuSO_4$ solution and 5 mL of PBS was added, homogenized and completed to volume with nanopure water. The absorbance of the formed ALEN-Cu complex was measured at 225 nm against a reagent blank prepared by the addition of 3 mL FaSSGF, 5 mL of PBS buffer and 15 mL of the $CuSO_4$ solution in a 25-mL volumetric flask and completed to volume with nanopore water. Dissolution profiles were recorded for ALEN sodium reagent, ALEN Sodium Tablets-USP (generic form of Fosamax®), ALEN-Ca forms I and II, and ALEN-Zn forms I and II, and ALEN-Mg. Dissolution tests were performed in 100 mL of PBS buffer (pH=7.40) and FaSSGF (pH=1.60), at 37° C. under constant stirring at 150 rpm. For the alendronate-based coordination complexes, reagent and tablets, 70 mg of the solid were grinded using a mortar and pestle. The powder was added to the buffer solution at the beginning of the dissolution under stirring. For dissolution in PBS, samples of 1.6 mL were collected after 0, 5, 10, 15, 20 and 25 s to record the dissolution for the deglutition profile. For the complete dissolution profile, samples of the exact volume amount were collected from 1-6 min, in one-minute intervals. After the six-minute period, samples for 10, 15 and 20 min were collected. For dissolution in FaSSGF, samples of 1.2 mL were collected at the same time intervals. After collection, the samples were filtrated using a PTFE filter. The filtered solutions were placed in 10 mL volumetric flasks. To produce the ALEN-Cu complex in PBS, 7.4 mL of the 2.5 mM $CuSO_4$ solution was added and completed to volume with nanopure water. The absorbance of the formed ALEN-Cu complex was measured at 231 nm against a reagent blank prepared by the addition of filtered 1.6 mL PBS buffer in a 10-mL volumetric flask, with 7.4 mL of the 2.5 mM copper (II) sulfate solution and completed to volume with nanopure water. To generate the ALEN-Cu complex in FaSSGF, 2 mL of PBS and 6 mL of the 2.5 mM $CuSO_4$ solution was added and completed to volume with nanopure water. The absorbance of the formed ALEN-Cu complex was measured at 225 nm against a reagent blank prepared by the addition of filtered 1.2 mL FaSSGF solution in a 10-mL volumetric flask, with 2 mL PBS buffer and 6 mL of the 2.5 mM copper (II) sulfate solution and completed to volume with nanopure water. Absorbance measurements were performed on an Agilent Technologies Cary Series UV-Vis Spectrophotometer, Cary 100 UV-Vis model; using the UV Cary Scan software version v.20.0.470. All measurements were performed with a 400-200 nm scan. FIGS. 16-23 show absorbance spectra, calibration curves and dissolution profiles according to the present invention.

With these results it can be observed that structural stability of the pBioCCs in different media varying pH, depends on the nature of the metal, their ionic radius and its coordinates with the ligand. Because the metals employed are isovalent, structure stability was not affected by change or modification in the valence charge distribution. Also, for all metal complexes synthesized, the coordination number is 6 for exception of ALEN-Ca form I which is 7 for the calcium ion.

In PBS, stability of the complexes increases as the atomic number (Z) increase based on these experimental results. The order of stability can be resumed as ($Mg^{2+}<Ca^{2+}<Zn^{2+}$), being the form II of the pBioCCs more stable than the form I (ALEN-Mg<ALEN-Ca form I<ALEN-Ca form II<ALEN-Zn form I<ALEN-Zn form II).

In FaSSGF, a different trend can be observed, where the stability is very low for the calcium coordinates and increases for magnesium and zinc ($Ca^{2+}<Mg^{2+} \leq Zn^{2+}$). Based on the ionic radius of these metals, being calcium the larger and magnesium the smaller one (zinc is marginally larger than magnesium), prediction of the strengths of the coordination bonds can be done. Smaller ions promote stronger bonds due to the shorter distance between atoms. These results are consistent with the reported trend of M-O bonds (M=$Ca^{2+}$, $Mg^{2+}$, $Zn^{2+}$), where the bond strength is given by Ca—O<Mg—O<Zn—O. As the size of the ionic radii of the metal decrease, the M-O bond strength increases, and therefore the structure stability will increase as observed for the dissolution of the metal complexes in FaSSGF. The relationship between the length of the M-O bond with its strength can be supported with data collected from the molecular simulation of the pBioCCs from the SCXRD. The M-O average bond length for structures containing calcium in its coordinates is 2.429 Å and 2.339 Å (ALEN-Ca form I and II respectively). For ALEN-Mg, an average of 2.085 Å was calculated for the M-O bonds. For the structures containing zinc, an average of 2.032 Å and 2.116 Å (ALEN-Zn form I and II respectively) was calculated. For the pBioCCs, the M-O bond length trend is as follows $Ca^{2+}>Mg^{2+}\geq Zn^{2+}$. The results from the dissolution profiles in FaSSGF correlates with this last trend because ALEN-Ca form I and II were the less stable complexes and ALEN-Zn form II the most stable one. As explained before, if the bond length between the oxygen and the metal is shorter, stronger it is, giving more stability to the structure itself. Also, these data for the dissolution profiles is consistent with the relationship of the Mullikan charges of the metal ion with the ionic radius of the metal ions. These charge values give insights of the nature of the cations, revealing that as the Mulliken charge increases, the cation becomes more ionic. Mulliken charges reported for calcium, magnesium and zinc present a trend as follow $Ca^{2+}>Mg^{2+}>Zn^{2+}$. Correlating the charge with the bond strength, if the Mulliken charge decrease, the ionic radii decreases, and therefore shorter the bond and stronger it becomes.

In PBS, form II of the pBioCCs are more stable than the form I when comparing polymorphs of the same metal. In FaSSGF, despite of ALEN-Mg being more stable than ALEN-Zn form I, ALEN-Zn form II presented the lowest dissolution rate and higher stability among all pBioCCs (ALEN-Ca form I<ALEN-Ca form II<ALEN-Zn form I<ALEN-Mg<ALEN-Zn form II). The similarity of the decomposition of the structure in acidic media for ALEN-Mg and ALEN-Zn form II can be attributed to the isostructural nature between these two metal complexes and the relatively small difference in the ionic properties of both cations ($Mg^{2+}$ and $Zn^{2+}$).

It has been described the hydrothermal reaction and the structural characterization of a series of pBioCCs constructed by employing clinically utilized BP (ALEN) as ligand and three biologically relevant metals ($Ca^{2+}$ $Mg^{2+}$ and $Zn^{2+}$). An unprecedented number of pBioCCs were obtained and structurally characterized by single crystal X-ray diffraction. The reaction pH was an important determinant in the protonation state of the pBioCPs obtained. There seems to be a direct relationship between the ligand's deprotonation state and the formation of denser 3D structures. Five pBioCCs were structurally characterized to provide further insights into the structural motifs observed in these types of materials. These compounds have been obtained as single phases and exhibit high to moderate thermal stability under an inert atmosphere.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

The invention claimed is:

1. A bisphosphonate-based coordination complex comprising: a mixture of alendronic acid, etidronic acid and a magnesium salt, wherein a single crystal form is characterized by major x-ray powder diffraction peaks at 2θ angles of 10.46, 10.88, 14.46, 19.96, 22.60, and 23.08.

2. The bisphosphonate-based coordination complex of claim 1, having an empirical formula of: $Mg_2[C_{16}H_{12}N_2O_7P_2(H_2O)_2]\cdot 2H_2O$.

3. The bisphosphonate-based coordination complex of claim 1, wherein said alendronic acid, etidronic acid and magnesium salt are mixed at a molar ratio of 1:1:1.

4. The bisphosphonate-based coordination complex of claim 1, wherein the single crystal form is characterized by X-ray powder diffraction pattern of FIG. 7E.

5. The bisphosphonate-based coordination complex of claim 1, wherein said magnesium salt is magnesium nitrate hexahydrate.

6. The bisphosphonate-based coordination complex of claim 1, wherein the single crystal form has a monoclinic unit cell with cell parameters: a=12.5466 Å, b=3.3994 Å, c=12.4156 Å and β=106.243°.

7. The bisphosphonate-based coordination complex of claim 1, wherein the single crystal form has monoclinic space group of $P2_1/c$.

* * * * *